(12) United States Patent
Boyce et al.

(10) Patent No.: US 10,906,884 B2
(45) Date of Patent: *Feb. 2, 2021

(54) BENZODIAZEPINE DERIVATIVES AS CCK2/GASTRIN RECEPTOR ANTAGONISTS

(71) Applicant: Trio Medicines Ltd, Brighton (GB)

(72) Inventors: Malcolm James Boyce, London (GB); Liv Thomsen, London (GB); Donald Alan Gilbert, Ipswich (GB); David Wood, Sudbury (GB)

(73) Assignee: TRIO MEDICINES LTD, Brighton (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/382,737

(22) Filed: Apr. 12, 2019

(65) Prior Publication Data

US 2019/0233391 A1     Aug. 1, 2019

Related U.S. Application Data

(63) Continuation of application No. 15/502,490, filed as application No. PCT/GB2015/052291 on Aug. 7, 2015, now Pat. No. 10,308,627.

(30) Foreign Application Priority Data

Aug. 8, 2014 (GB) .................... 1414116.2

(51) Int. Cl.
C07D 401/04 (2006.01)
A61P 1/14 (2006.01)

(52) U.S. Cl.
CPC .............. *C07D 401/04* (2013.01); *A61P 1/14* (2018.01)

(58) Field of Classification Search
None
See application file for complete search history.

(56) References Cited

U.S. PATENT DOCUMENTS

| | | | |
|---|---|---|---|
| 4,820,834 A | 4/1989 | Evans et al. | |
| 5,218,114 A | 6/1993 | Bock et al. | |
| 5,563,136 A | 10/1996 | Capet et al. | |
| 10,308,627 B2 * | 6/2019 | Boyce | A61P 1/14 |

FOREIGN PATENT DOCUMENTS

| | | |
|---|---|---|
| CN | 1074216 A | 7/1993 |
| EP | 0167919 A2 | 1/1986 |
| EP | 0 434 369 A1 | 6/1991 |
| EP | 0445976 B1 | 9/1991 |
| EP | 0 490 590 A1 | 6/1992 |
| EP | 0 628 033 B1 | 7/2003 |
| EP | 1 342 719 A1 | 9/2003 |
| WO | 1993/008175 A1 | 4/1993 |
| WO | 1993/016999 A1 | 9/1993 |
| WO | 199319063 A1 | 9/1993 |
| WO | 9506040 A1 | 3/1995 |
| WO | 9506041 A1 | 3/1995 |
| WO | 1994/024151 A1 | 10/1997 |
| WO | 1998/015535 A1 | 4/1998 |
| WO | 2003041714 A1 | 5/2003 |
| WO | 2004101533 A1 | 11/2004 |
| WO | WO 2005/090319 | 9/2005 |

OTHER PUBLICATIONS

Spencer, "Bioorganic and Medicinal Chemistry", 208, 16, 2974-83 (Year: 2008).
Berna, M.J. et al. (2007) "Role of CCK/gastrin receptors in gastrointestinal/metabolic diseases and results of human studies using gastrin/CCK receptor antagonists in these diseases," Curr Top Med Chem. 7(12):1211-1231.
Boyce, M. et al. (2013) "Netazepide, a gastrin/CCK2 receptor antagonist, causes dose-dependent, persistent inhibition of the responses to pentagastrin in healthy," Br J Clin Pharmacol, 76(5): 689-698.
Fossmark, R. et al. (2012) Treatment of gastric carcinoid type 1 with the gastrin receptor antagonist netazepide , (YF476) results in regression of tumors and normalisation of serum chromogranin A, Alimentary Pharmacology & Therapeutics, 36:1067-1075.
Kramer et al. (1995) "A placebo-controlled trial of L-365,260, a CCKB antagonist, in panic disorder," Biol. Psychiatry. 37:462-466.
Murphy et al. (1993) "The gastrin-receptor antagonist L-365,260 inhibits stimulated acid secretion in humans," Clin. Pharmacol. Ther. 54:533-539.
Semple et al. (1997) "(3R)-N-(1-(tert-butylcarbonylmethyl)-2,3-dihydro-2-oxo-5-(2-pyridyl)-1H-1,4-benzodiazepin-3-/1)-N'-(3-(methylamino)phenyOurea (YF476): a potent and orally active gastrin/CCK-B antagonist," J. Med. Chem. 10:331-341.
Yano et al. (1996) "In vitro stability and in vivo absorption studies of colloidal particles formed from a solid dispersion system," Chem. Pharm. Bull. (Tokyo). 44:2309-2313.
International Search Report with Written Opinion corresponding to International Patent Application No. PCT/3B2015/052291, dated Oct. 15, 2015.

(Continued)

*Primary Examiner* — Noble E Jarrell
(74) *Attorney, Agent, or Firm* — Brian C. Trinque; Lathrop GPM LLP

(57) ABSTRACT

The invention relates to benzodiazepine derivatives of formula (A) useful as $CCK_2$/gastrin receptor antagonists, their preparation and their use in the treatment or prevention of disorders associated with $CCK_2$/gastrin receptors, disorders caused by or associated with hypergastrinaemia, and gastric acid-related disorders.

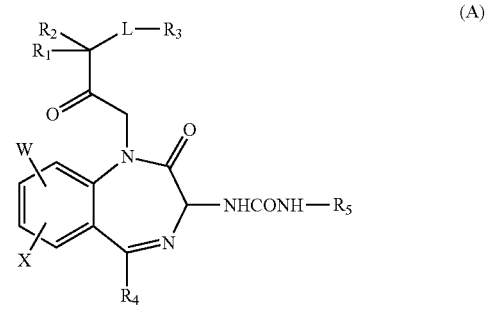

(A)

25 Claims, 1 Drawing Sheet

(56) References Cited

OTHER PUBLICATIONS

Bock et al. (1993) "Development of 1,4-benzodiazepine cholecystokinin type B antagonists," J. Med. Chem. 36(26):4276-4292.
U.S. Appl. No. 15/750,339 / 2018/0237400 / U.S. Pat. No. 10,570,102, filed Feb. 5, 2018 / Aug. 23, 2018 / Feb. 25, 2020, Malcolm James Boyoce.
U.S. Appl. No. 16/741,064, filed Jan. 13, 2020, Malcolm James Boyce.
U.S. Appl. No. 15/502,490 / 2018/0215728/ U.S. Pat. No. 10,380,627, filed Feb. 7, 2017 / Aug. 2, 2018 / Jun. 4, 2019, Malcolm James Boyce.
U.S. Appl. No. 16/382,737 / 2019/0233391, filed Apr. 12, 2019 / Aug. 1, 2019, Malcolm James Boyce.

* cited by examiner

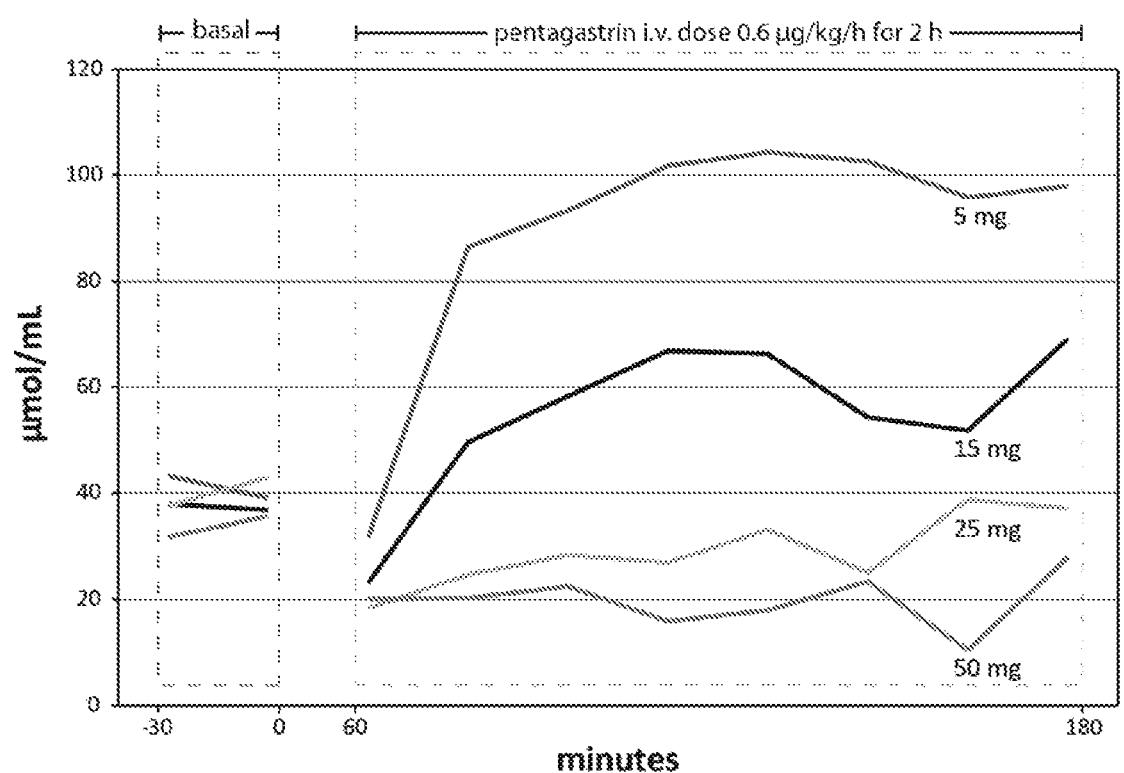

BENZODIAZEPINE DERIVATIVES AS CCK2/GASTRIN RECEPTOR ANTAGONISTS

RELATED APPLICATIONS

This application is a continuation of U.S. patent application Ser. No. 15/502,490, filed Feb. 7, 2017, which application is a National Entry Application of PCT application No. PCT/GB2015/052291, filed on Aug. 7, 2015, which claims priority to Great Britain Patent Application No. 1414116.2, filed Aug. 8, 2014. The contents of each of these applications are incorporated herein by reference in their entireties.

FIELD OF THE INVENTION

The invention relates to novel benzodiazepine derivatives useful as $CCK_2$/gastrin receptor antagonists, their preparation and their use in the treatment or prevention of disorders associated with $CCK_2$/gastrin receptors, disorders caused by or associated with hypergastrinaemia, and gastric acid-related disorders.

BACKGROUND

Gastrin is a peptide hormone produced by a single gene and synthesised from a precursor peptide preprogastrin, which is processed into progastrin and gastrin peptide fragments of various sizes by sequential enzymatic cleavage. There are 3 main forms of gastrin: gastrin-34 (G34 or 'big gastrin'), gastrin-17 (G17 or 'little gastrin'), and gastrin-14 (G14 or 'minigastrin'). All gastrins have a C-terminal amidated tetrapeptide (Trp-Met-Asp-Phe-$NH_2$), which acts at a specific G protein-coupled gastrin receptor (also called $CCK_2$ receptor; formerly known as $CCK_B$ receptor) in the stomach and in the central and peripheral nervous systems.

Gastrin is structurally and functionally related to another peptide hormone, cholecystokinin (CCK), which is also produced by a single gene and processed into several molecular forms by sequential enzymatic cleavage. The main forms in blood and tissue are CCK-58, CCK-33 and CCK-8. All fragments have at their carboxyl terminus the octapeptide Asp-Tyr($SO_3H$)-Met-Gly-Trp-Met-Asp-Phe-$NH_2$, which stimulates specific G protein-coupled $CCK_1$ receptors on pancreatic acinar cells, gall bladder smooth muscle, vagal afferent neurons in the small intestine, and cells in the central nervous system. The C-terminal tetrapeptide (Trp-Met-Asp-Phe-$NH_2$) is identical to that of gastrin. As a result, CCK has weak gastrin-like activity and gastrin has weak CCK-like activity. The common C-terminal tetrapeptide has hindered the development of selective antagonists for the $CCK_1$ or $CCK_2$ receptor, and has confounded assays for CCK, because antibodies to CCK may crossreact with gastrin.

Gastrin stimulates gastric acid secretion via a mechanism involving activation of gastrin ($CCK_2$) receptors.

Gastrin also causes proliferation, migration and differentiation of gastric epithelial cells, and up-regulates various genes, such as chromogranin A (CgA), histidine decarboxylase (HDC), vesicular monoamine transporter 2 (VMAT2), matrix metalloproteinase (MMP)-7, and protein Reg 1A, and stimulates paracrine cascades, including cytokines, growth factors such as trefoil factor, and prostanoids. Gastric acid secretion is regulated by endocrine, paracrine, and neurocrine mechanisms via at least three signalling pathways: gastrin-histamine (stimulation), $CCK_1$/somatostatin (inhibition) and neural networks (both stimulation and inhibition). Different pathways are suppressed or dominate, depending on the circumstances.

Circulating gastrin is increased by: hypoacidity due to autoimmune chronic atrophic gastritis (CAG) or *H. pylori*-induced gastritis; a gastrinoma in patients with Zollinger-Ellison syndrome (ZES); and acid suppression by histamine $H_2$-receptor antagonists, proton pump inhibitors (PPIs), potassium-competitive acid inhibitors or vagotomy. CAG hypergastrinaemia leads to ECL-cell hyperplasia and, in some patients, development of gastric carcinoids (type 1 neuroendocrine tumours), which are mostly benign but can become malignant. Patients with pernicious anaemia, which is one of the possible clinical presentations of atrophic gastritis, have a nearly seven-fold increased risk of gastric cancer. ZES hypergastrinaemia causes hyperacidity, peptic ulceration and gastric carcinoids (type 2 neuroendocrine tumours), which have greater potential for malignancy, especially in patients with the multiple endocrine neoplasia type 1 gene. *H. pylori* infection is a major risk factor for peptic ulcer disease and gastric cancer. PPI-induced hypergastrinaemia causes: enterochromaffin-like (ECL)-cell hyperplasia; parietal cell hyperplasia; fundic gland polyps; bone loss, impaired bone quality and bone fractures; and possibly malignant ECL-cell tumours in some patients. PPI withdrawal leads to rebound hyperacidity and, in some people, dyspepsia. Gastrin receptors are also expressed on pancreatic cancer, colonic cancer, medullary thyroid cancer, and Barrett's oesophagus cells. PPI-induced hypergastrinaemia is associated with advanced neoplasia in Barrett's oesophagus. Thus, there are various potential clinical indications for a gastrin/$CCK_2$ receptor antagonist.

A known 1,4-benzodiazepine-derived $CCK_2$ receptor antagonist is L-365,260, which possesses nanomolar affinity at $CCK_2$ receptors and reasonable selectivity (140-fold) versus the $CCK_1$ receptor. However, oral L-365,260 produced only modest and short lasting inhibition of gastrin-stimulated acid secretion in healthy men, and was ineffective in limiting panic attacks in patients, results attributed to its low aqueous solubility and poor oral bioavailability (Murphy et al. Clin Pharmacol Ther 1993; 54: 533-39 and Kramer et al. Biol Psychiatry 1995; 37: 462-466).

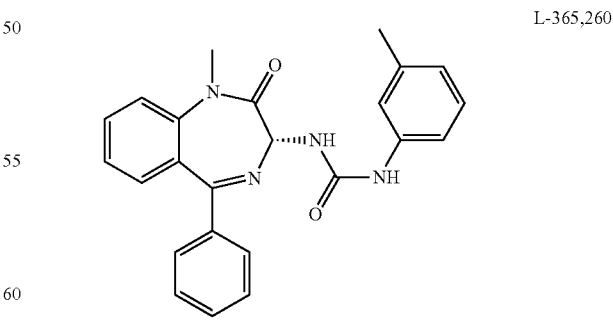

L-365,260

Another known 1,4-benzodiazepine-based $CCK_2$ receptor antagonist is YM022. YM022 showed subnanomolar affinity at rat brain $CCK_2$ receptors, which was more than two orders of magnitude higher than that for rat pancreatic $CCK_1$ receptors.

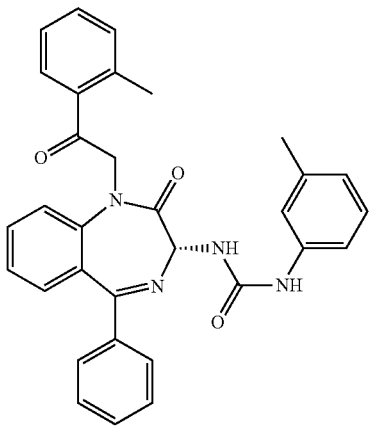

YM022

However, YM022 suffered low aqueous solubility and had to be formulated as a solid dispersion to achieve adequate oral bioavailability (Yano et al. Chem Pharm Bull (Tokyo) 1996; 44: 2309-2313).

Subsequently, YF476 was developed, which had a binding affinity at $CCK_2$ receptors similar to that of YM022, but was 5-fold more selective for $CCK_2$ receptors than for $CCK_1$ receptors (Semple et al. J Med Chem 1997; 40: 331-341).

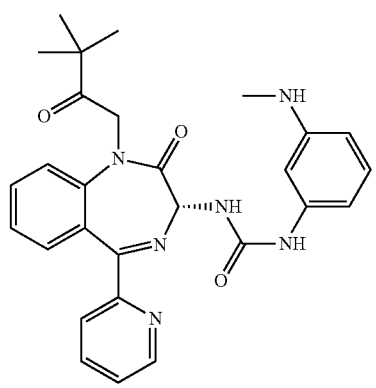

YF476

Examples of benzodiazepine derivatives that act as antagonists at $CCK_2$ receptors are also given in U.S. Pat. No. 4,820,834 and European Patents EP 0 628 033 B1 and EP 1 342 719 B1.

Despite considerable effort of pharmaceutical companies for three decades, no $CCK_2$/gastrin receptor antagonist has been developed into a medicine, mainly because of problems with potency, selectivity between $CCK_1$ and $CCK_2$ receptors, agonist activity, solubility, and oral bioavailability.

Accordingly, there remains a need for an efficacious $CCK_2$/gastrin receptor antagonist which can successfully be used in pharmaceutical compositions to provide beneficial properties in terms of pharmacokinetics, improved bioavailability, avoidance of a requirement for administration with food, minimisation of processing steps required in formulation, and the like.

It has been determined that serum concentrations of YF476 were extremely low and very variable when YF476 was administered in a crystalline form to healthy subjects. Bioavailability can be improved by preparing and administering a formulation of amorphous YF476, but this requires stabilisation such as in the form of a solid dispersion on hydroxypropyl methyl cellulose by spray-drying. Even with this processing, bioavailability of YF476 was still low. Because food increased bioavailability of YF476 by 1.6-fold in healthy subjects, it was administered with food in the patient studies. However, it would be beneficial to provide a $CCK_2$/gastrin receptor antagonist where administration with food is not required.

The inventors have now identified a class of compounds that exhibit properties favourable for successful use as a $CCK_2$/gastrin receptor antagonist and, if provided in the form of a pharmaceutical composition for administration to a patient, addresses problems previously hindering successful development of a $CCK_2$/gastrin receptor antagonist into a medicine.

SUMMARY OF THE INVENTION

In a first aspect, the present invention provides a pharmaceutical composition comprising a compound of formula (A)

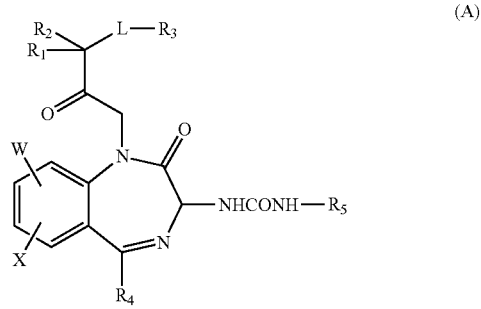

(A)

or a pharmaceutically acceptable salt, ester, thioester, salt of an ester or thioester, or prodrug thereof, wherein, $R_1$ and $R_2$ are each, independently, H, $C_{1-3}$ aliphatic, halo, or $C_{1-3}$ haloaliphatic, or wherein $R_1$ and $R_2$ together with the intervening carbon atom to which they are bonded, form a $C_{3-6}$ carbocyclic moiety;

L is a bond or $C_{1-3}$ alkylene;

$R_3$ is —$OR_6$ or —$SR_6$;

W and X are, independently, hydrogen, halo, $C_{1-8}$ alkyl or $C_{1-8}$ alkoxy;

$R_4$ and $R_5$ are both, independently, a monocyclic aryl or heteroaryl, optionally substituted with one or more substituents independently selected from halo, hydroxy, amino, nitro, carboxyl, carboxamido, cyano, —$SO_3H$, and optionally substituted $C_{1-5}$ alkyl, $C_{1-8}$ alkoxy, alkylamino or di($C_{1-8}$ alkyl)amino; and $R_6$ is hydrogen or alkyl (preferably methyl);

and optionally one or more pharmaceutically acceptable excipient(s).

In some embodiments, at least one of $R_4$ and $R_5$ is unsubstituted or substituted phenyl or pyridyl. At least one of $R_4$ and $R_5$ may be unsubstituted, monosubstituted or disubstituted phenyl or unsubstituted, monosubstituted or disubstituted 2-, 3- or 4-pyridyl. $R_4$ and $R_5$ may independently be selected from unsubstituted or substituted phenyl or pyridyl.

Where $R_4$ and/or $R_5$ is substituted with optionally substituted $C_{1-8}$ alkyl, $C_{1-8}$ alkoxy, $C_{1-8}$ alkylamino or di($C_{1-8}$ alkyl)amino, the optional substituents on $C_{1-8}$ alkyl, $C_{1-8}$ alkoxy, $C_{1-8}$ alkylamino and di($C_{1-8}$ alkyl)amino include any substituent as described herein for substituents on an aliphatic group, for example, halo, —$NO_2$, —CN, amino, $C_{1-8}$ alkylamino, di($C_{1-8}$ alkyl)amino, —S(O)H or —$CO_2H$.

In some embodiments, $R_5$ is phenyl having a meta substituent chosen from NHMe, NMeEt, $NEt_2$, F, Cl, Br, OH, $OCH_3$, $NH_2$, $NMe_2$, $NO_2$, Me, $(CH_2)_n$—$CO_2H$, CN, $CH_2NMe_2$, NHCHO and $(CH_2)_n$—$SO_3H$ where n is 0-2; unsubstituted phenyl or 2-, 3- or 4-pyridyl optionally with a substituent selected from F, Cl, $CH_3$ and $CO_2H$; and $R_4$ is 2-, 3- or 4-pyridyl or phenyl.

In any of the above embodiments, W and X may independently be H, halo, $C_{1-3}$ alkyl or $C_{1-3}$ alkoxy. Preferably, W and X are both H.

The compound of formula (A) may be a compound of formula (B):

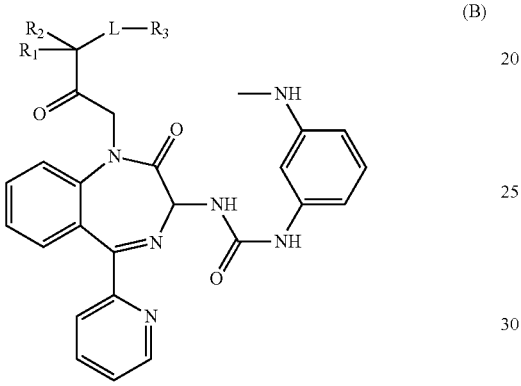

(B)

or a pharmaceutically acceptable salt, ester, thioester, salt of an ester or thioester, or prodrug thereof, wherein $R_1$, $R_2$, L, $R_3$ and $R_6$ are as defined in relation to formula (A).

In any of the above embodiments of formula (A) or (B), where $R_1$ and $R_2$ together with the intervening carbon atom to which they are bonded, form a carbocyclic moiety, the carbocyclic moiety may be a $C_{3-4}$ carbocyclic moiety.

In any of the above embodiments of formula (A) or (B), $R_1$ and $R_2$ may each, independently, be H or $C_{1-2}$ alkyl, L may be a bond or $C_{1-3}$ alkylene and $R_3$ may be —OH or —SH. In some embodiments, $R_1$ and $R_2$ may each, independently, be H or $C_{1-2}$ alkyl, L may be $C_1$ alkylene (—$CH_2$—) and $R_3$ may be —OH or —SH.

In any of the above embodiments of formula (A) or (B), $R_1$ and $R_2$ may each, independently, be $C_{1-2}$ alkyl, L may be $C_{1-3}$ alkylene and $R_3$ may be —OH. In some embodiments, $R_1$ and $R_2$ may each, independently, be $C_{1-2}$ alkyl, L may be $C_1$ alkylene (—$CH_2$—) and $R_3$ may be —OH.

The compounds of formula (A) and (B) contain a chiral centre at the position marked * below

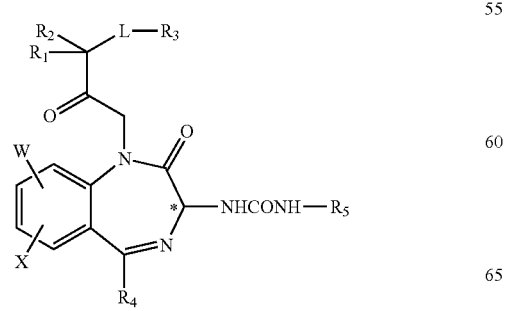

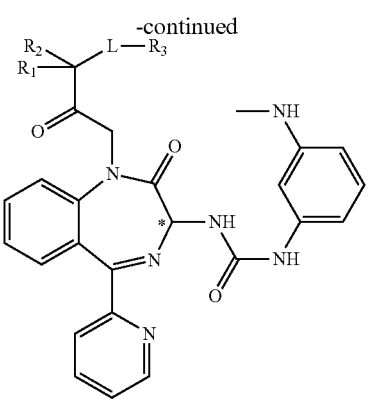

and may exist in enantiomeric forms:

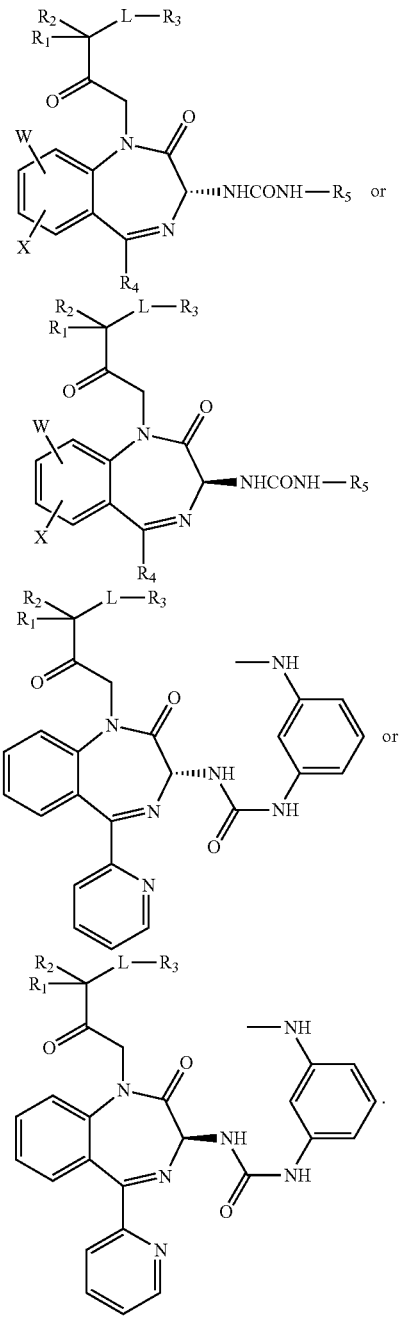

Compounds may be provided as a racemic mixture of enantiomers, a non-racemic mixture of enantiomers or as a single enantiomer in optically pure form, for example the R-enantiomer at*.
A compound of formula (A) or (B) may be, for example, a compound selected from:
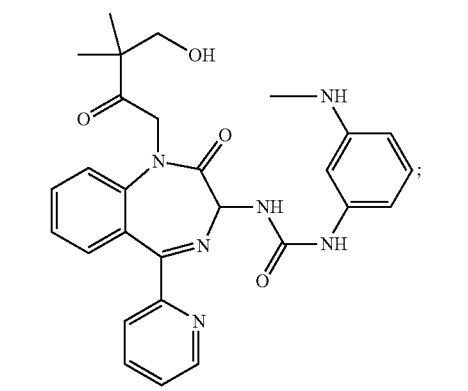
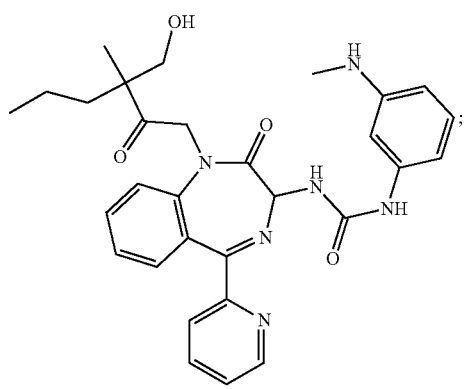
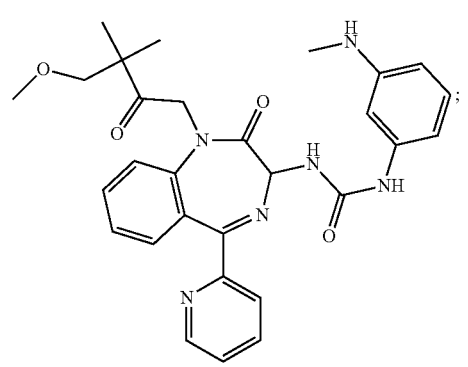
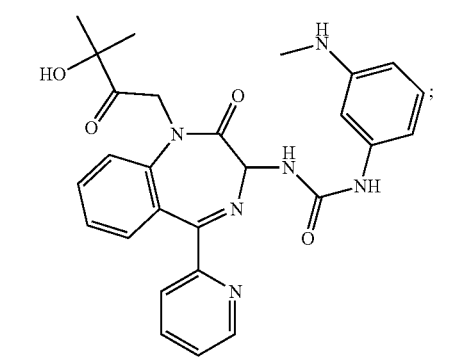
-continued
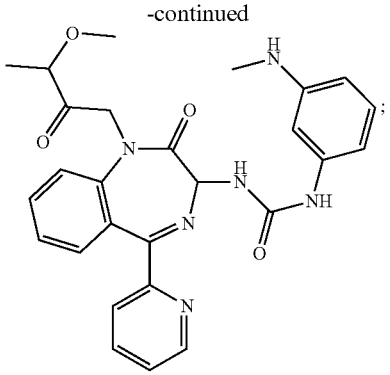
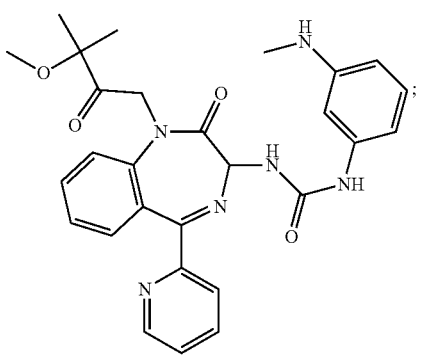
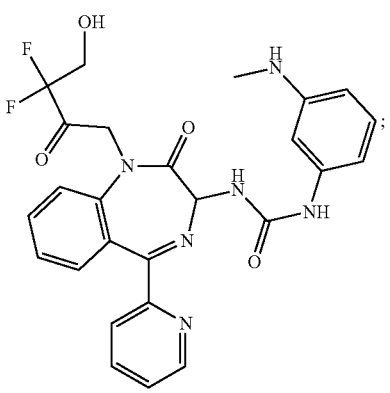
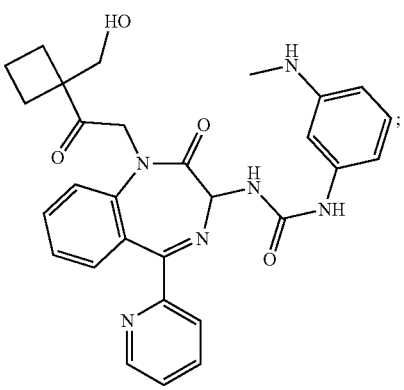

-continued
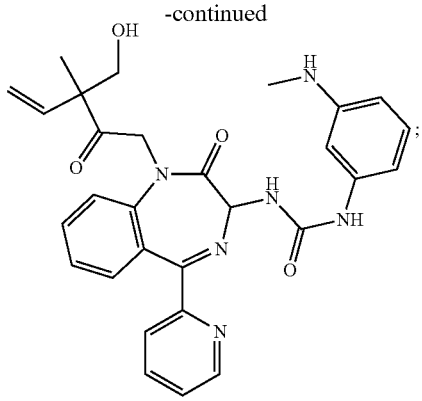
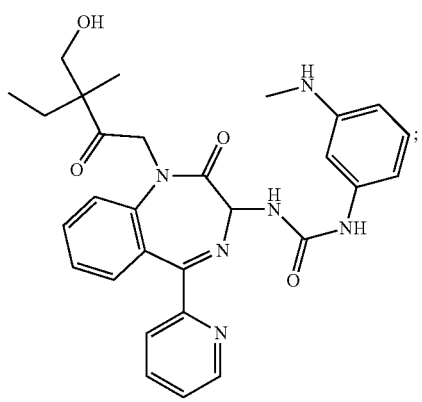
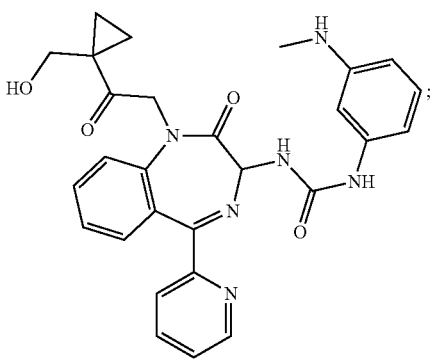
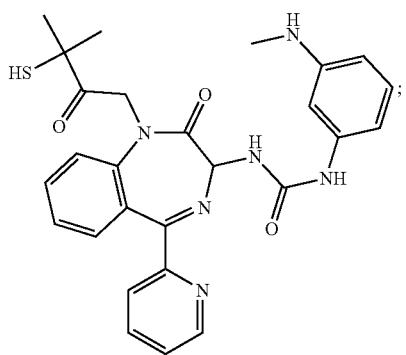
-continued
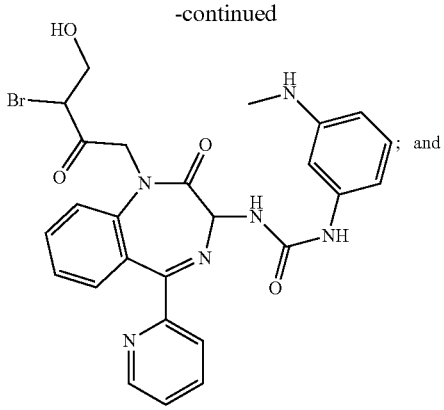
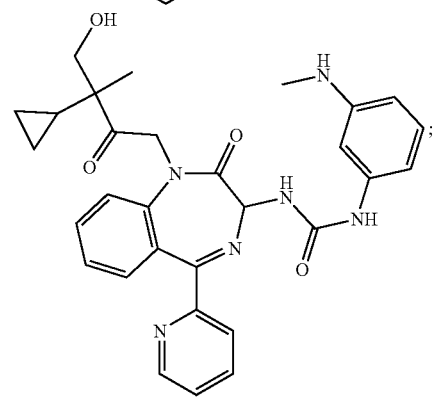
or a pharmaceutically acceptable salt, ester, thioester, salt of an ester or thioester, or prodrug thereof.
In some embodiments, the compound may be selected from:
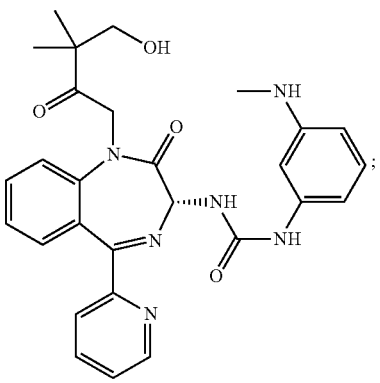
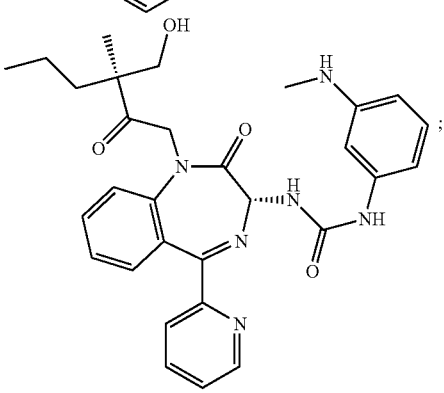

-continued

-continued

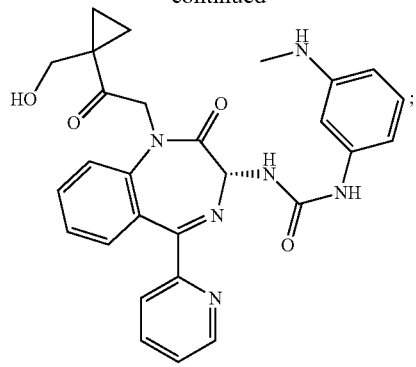

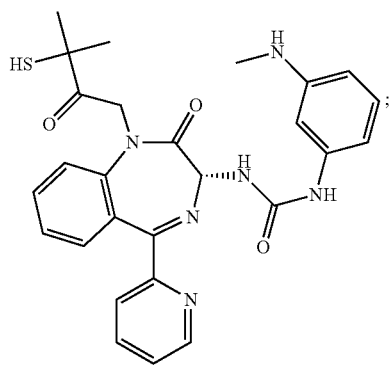

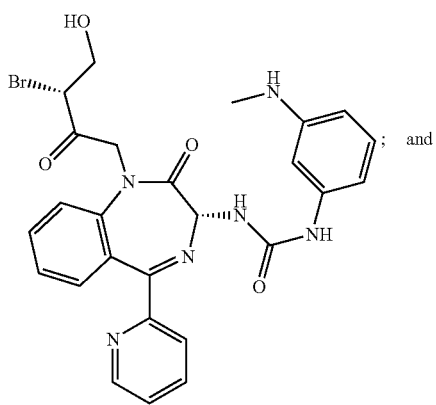

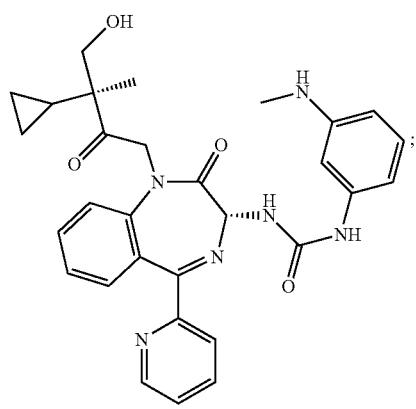

or a pharmaceutically acceptable salt, ester, thioester, salt of an ester or thioester, or prodrug thereof.

In a preferred embodiment, the compound of formula (A) or (B) is a compound (TR):

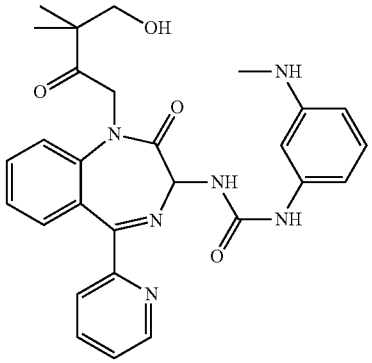

(TR)

or a pharmaceutically acceptable salt, ester, salt of an ester, or prodrug thereof.

Compound (TR) contains a chiral centre and therefore exists as two enantiomers, designated (TR2) (the R-enantiomer) and (TR3) (the S-enantiomer).

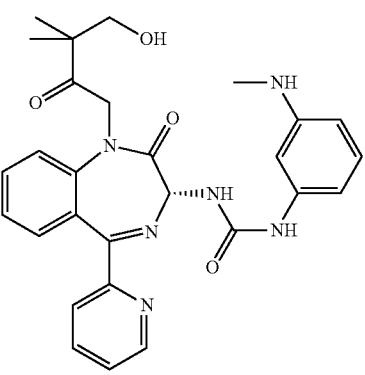

(TR2)

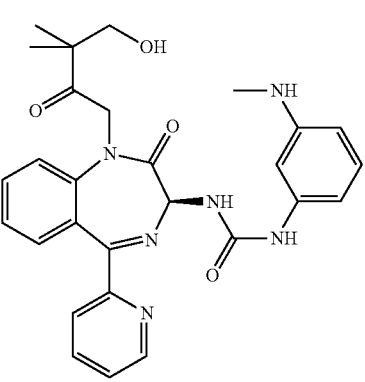

(TR3)

In a composition of the invention, TR may be provided as the racemic mixture of the enantiomers (TR2) and (TR3), a non-racemic mixture of the enantiomers (TR2) and (TR3) or as a single enantiomer (TR2 or TR3) in optically pure form. The racemic mixture of (TR2) and (TR3) is designated "(TR1)" herein.

The composition comprises, in some embodiments, an ester or thioester, or a pharmaceutically acceptable salt thereof, of any of the embodiments described herein of a compound of formula (A), (B) or (TR) wherein $R_3$ is —OH or —SH and the H of $R_3$ is replaced by a moiety —C(O)R, wherein R is an optionally substituted aliphatic, heteroaliphatic, aromatic or heteroaromatic moiety. Accordingly, the composition may comprise a compound of formula (A) or (B), or a pharmaceutically acceptable salt thereof, wherein $R_3$ is —$OR_6$, —$SR_6$, —$OC(O)R_7$ or —$SC(O)R_7$, $R_6$ is hydrogen or alkyl (preferably methyl), and $R_7$ is an optionally substituted aliphatic, heteroaliphatic, aromatic or heteroaromatic moiety. For example, the composition may comprise a compound of formula (C)

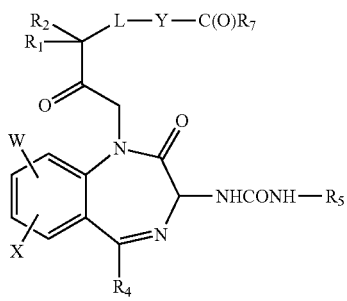

(C)

or a pharmaceutically acceptable salt thereof, wherein, $R_1$, $R_2$, L, W, X, $R_4$, $R_5$ are as defined in any of the embodiments herein for a compound of formula (A), (B) or (TR); Y is —O— or —S—; and $R_7$ is an optionally substituted aliphatic, heteroaliphatic, aromatic or heteroaromatic moiety. The compound of formula (C) may be a compound of formula (D):

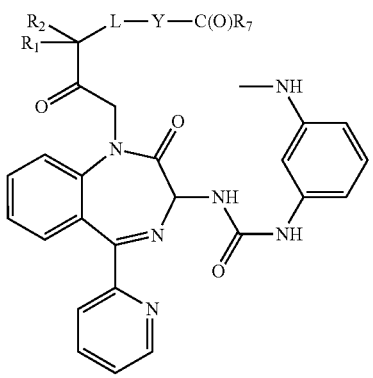

(D)

or a pharmaceutically acceptable salt thereof, wherein $R_1$, $R_2$, L, Y and $R_7$ are as defined above.

In some embodiments, $R_7$ is an optionally substituted aliphatic moiety, for example $R_7$ is substituted or unsubstituted $C_{1-6}$ aliphatic, preferably substituted or unsubstituted $C_{1-3}$ aliphatic, more preferably methyl. In some embodiments, Y is —O—.

A compound of formula (C) or (D) may, for example, be a compound of formula

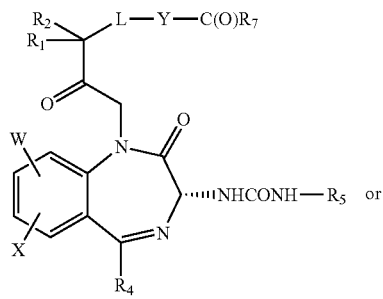

or

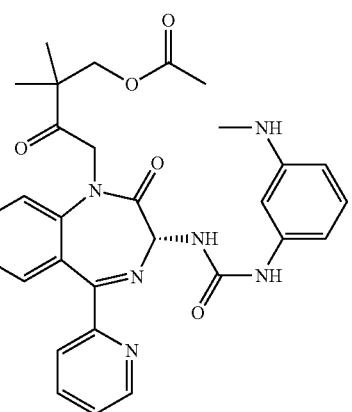

;

or a pharmaceutically acceptable salt thereof.

In a preferred embodiment, the compound of formula (C) or (D) is a compound (TR-A):

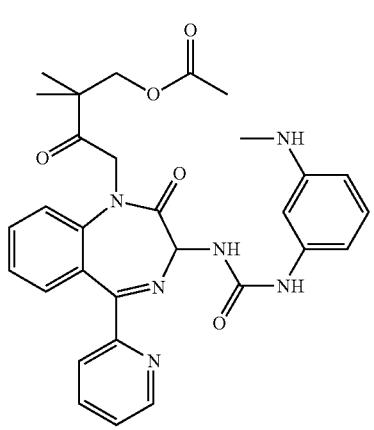

(TR-A)

or a pharmaceutically acceptable salt thereof. The compound (TR-A) may be provided as the racemic mixture (TR1-A) of the enantiomers (TR2-A) (the R-enantiomer) and (TR3-A) (the S-enantiomer), a non-racemic mixture of the enantiomers (TR2-A) and (TR3-A) or as a single enantiomer (TR2-A) or (TR3-A) in optically pure form.

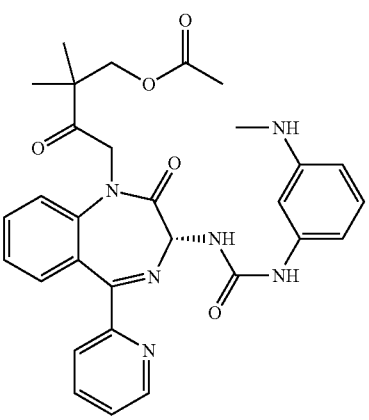

(TR2-A)

-continued (TR3-A)

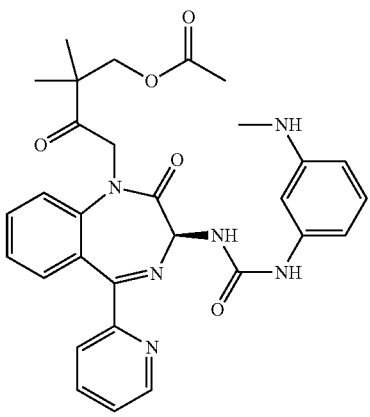

A composition of the invention may be provided as an oral or sublingual dosage form, such as a tablet or capsule. In other embodiments, a composition of the invention may be provided as a parenteral dosage form, such as an injectable solution or suspension or depot formulation.

A composition of the invention may optionally further comprise one or more additional active agents. An additional active agent may be, for example, a histamine $H_2$-receptor antagonist, a PPI, a potassium-competitive acid inhibitor or any other gastric acid suppressant. The histamine $H_2$-receptor antagonist may be, for example, a competitive histamine $H_2$-receptor antagonist, such as cimetidine, famotidine, nizatidine, roxatidine or ranitidine; or an insurmountable histamine $H_2$-receptor antagonist, such as loxtidine or lamitidine. The PPI may be, for example, esomeprazole, omeprazole, lanzoprazole, dexlansoprazole, pantoprazole, rabeprazole or ilaprazole. The potassium-competitive acid inhibitor may be, for example, revaprazan or TAK-438.

In other embodiments, an additional active agent may be a cytotoxic agent or a tumour-specific antibody.

In other embodiments, an additional active agent may be an analgesic, such as an opioid or dyhydrocodeine.

In a second aspect, the present invention provides a compound of formula (C)

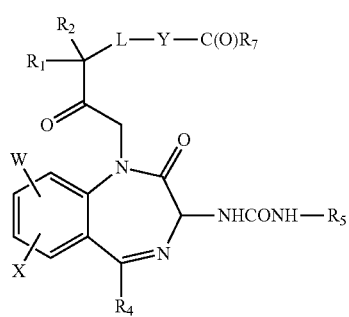

(C)

or a pharmaceutically acceptable salt thereof,
wherein, $R_1$ and $R_2$ are each, independently, H, $C_{1-3}$ aliphatic, halo, or $C_{1-3}$ haloaliphatic, or
wherein $R_1$ and $R_2$ together with the intervening carbon atom to which they are bonded, form a $C_{3-6}$ carbocyclic moiety;
L is a bond or $C_{1-3}$ alkylene;
Y is —O— or —S—;

W and X are, independently, hydrogen, halo, $C_{1-8}$ alkyl or $C_{1-8}$ alkoxy;

$R_4$ and $R_5$ are both, independently, a monocyclic aryl or heteroaryl, optionally substituted with one or more substituents independently selected from halo, hydroxy, amino, nitro, carboxyl, carboxamido, cyano, —$SO_3H$, and optionally substituted $C_{1-8}$ alkyl, $C_{1-8}$ alkoxy, $C_{1-8}$ alkylamino or di($C_{1-8}$ alkyl)amino; and $R_7$ is an optionally substituted aliphatic, heteroaliphatic, aromatic or heteroaromatic moiety.

In some embodiments, at least one of $R_4$ and $R_5$ is unsubstituted or substituted phenyl or pyridyl. At least one of $R_4$ and $R_5$ may be unsubstituted, monosubstituted or disubstituted phenyl or unsubstituted, monosubstituted or disubstituted 2-, 3- or 4-pyridyl. $R_4$ and $R_5$ may independently be selected from unsubstituted or substituted phenyl or pyridyl.

Where $R_4$ and/or $R_5$ is substituted with optionally substituted $C_{1-8}$ alkyl, $C_{1-8}$ alkoxy, $C_{1-8}$ alkylamino or di($C_{1-8}$ alkyl)amino, the optional substituents on $C_{1-8}$ alkyl, $C_{1-8}$ alkoxy, $C_{1-8}$ alkylamino and di($C_{1-8}$ alkyl)amino include any substituent as described herein for substituents on an aliphatic group, for example, halo, —$NO_2$, —CN, amino, $C_{1-8}$ alkylamino, di($C_{1-8}$ alkyl)amino, —S(O)H or —$CO_2H$.

In some embodiments, $R_5$ is phenyl having a meta substituent chosen from NHMe, NMeEt, $NEt_2$, F, Cl, Br, OH, $OCH_3$, $NH_2$, $NMe_2$, $NO_2$, Me, $(CH_2)_n$—$CO_2H$, CN, $CH_2NMe_2$, NHCHO and $(CH_2)_n$—$SO_3H$ where n is 0-2; unsubstituted phenyl or 2-, 3- or 4-pyridyl optionally with a substituent selected from F, Cl, $CH_3$ and $CO_2H$; and $R_4$ is 2-, 3- or 4-pyridyl or phenyl.

In any of the above embodiments, W and X may independently be H, halo, $C_{1-3}$ alkyl or $C_{1-3}$ alkoxy. Preferably, W and X are both H.

The compound of formula (C) may be a compound of formula (D):

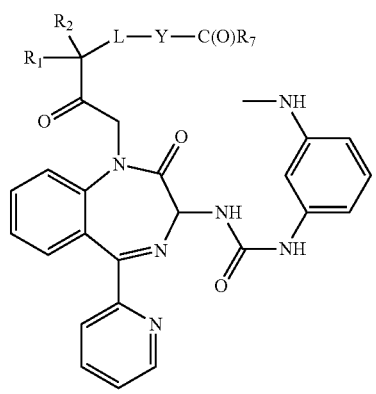

(D)

or a pharmaceutically acceptable salt thereof, wherein $R_1$, $R_2$, L, Y and $R_7$ are as defined in relation to formula (C).

In any of the above embodiments of formula (C) or (D), where $R_1$ and $R_2$ together with the intervening carbon atom to which they are bonded, form a carbocyclic moiety, the carbocyclic moiety may be a $C_{3-4}$ carbocyclic moiety.

In any of the above embodiments of formula (C) or (D), $R_1$ and $R_2$ may each, independently, be H or $C_{1-2}$ alkyl, and L may be a bond or $C_{1-3}$ alkylene. In some embodiments, $R_1$ and $R_2$ may each, independently, be H or $C_{1-2}$ alkyl, and L may be $C_1$ alkylene (—$CH_2$—).

In any of the above embodiments of formula (C) or (D), $R_1$ and $R_2$ may each, independently, be $C_{1-2}$ alkyl, L may be $C_{1-3}$ alkylene and Y may be —O—. In some embodiments, $R_1$ and $R_2$ may each, independently, be $C_{1-2}$ alkyl, L may be $C_1$ alkylene (—CH$_2$—) and Y may be —O—.

In any of the above embodiments of formula (C) or (D), $R_7$ may be optionally substituted aliphatic, for example $R_7$ may be substituted or unsubstituted $C_{1-6}$ aliphatic, preferably substituted or unsubstituted $C_{1-3}$ aliphatic, more preferably methyl.

A compound of formula (C) or (D) may, for example, be a compound of formula

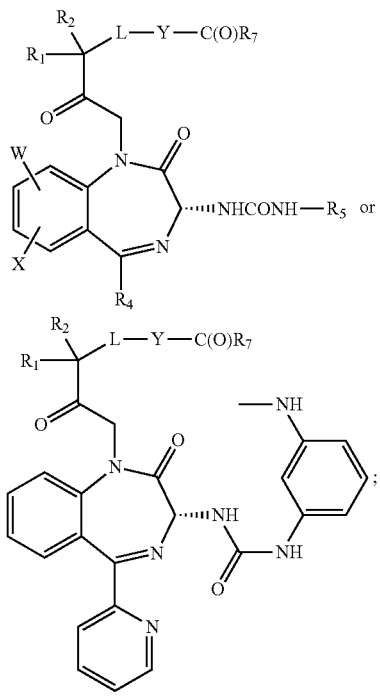

or a pharmaceutically acceptable salt thereof.

A compound of formula (C) or (D) may be a compound of formula (E):

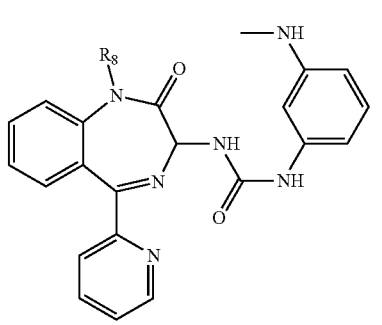

or a pharmaceutically acceptable salt thereof, wherein R8 is selected from

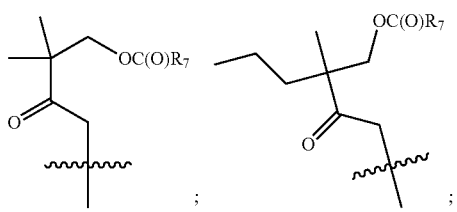

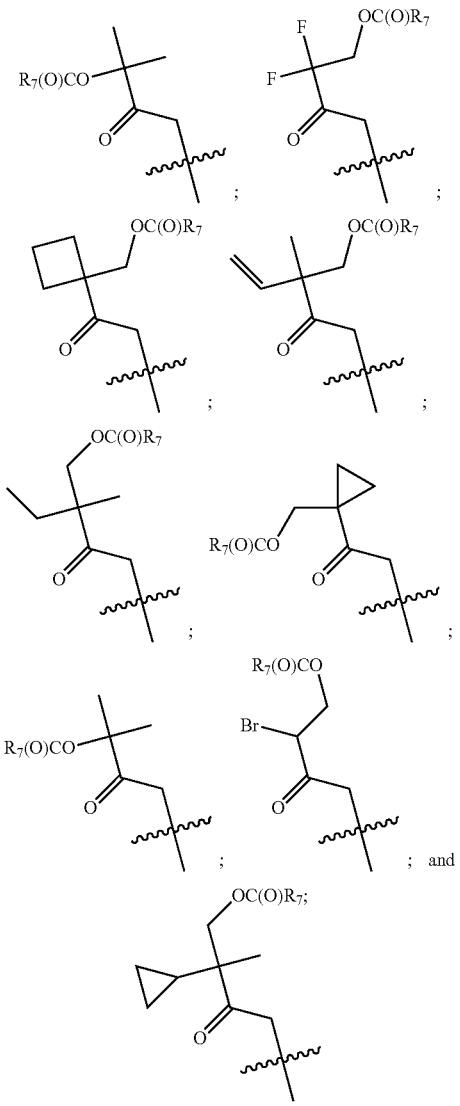

wherein $R_7$ is as defined for any of the embodiments of formula (C) or (D) above.

In some embodiments, the compound of formula (E) may be a compound of formula (F):

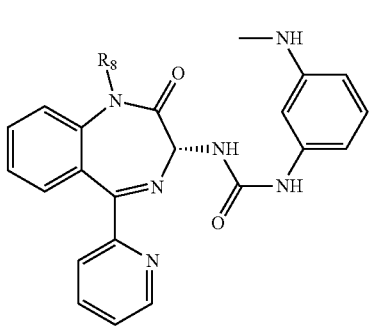

or a pharmaceutically acceptable salt thereof. Preferably, $R_5$ is selected from:

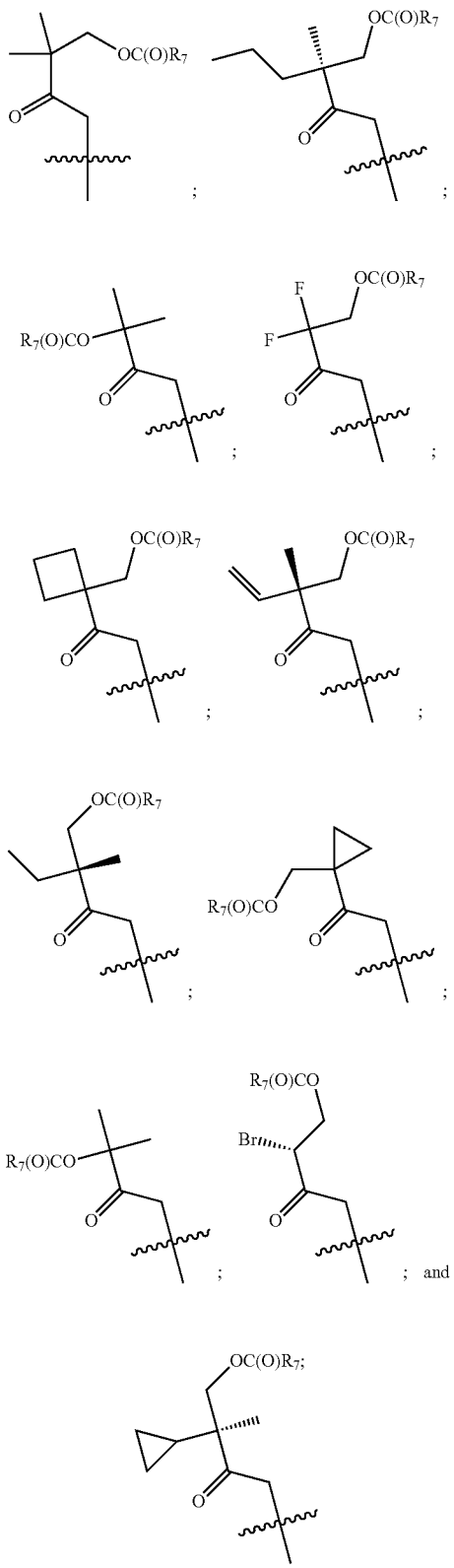

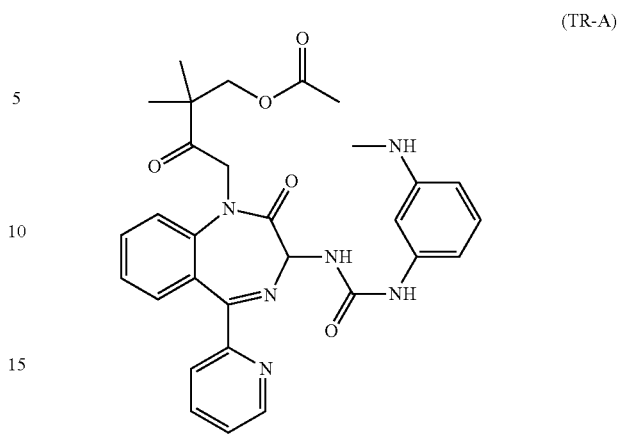

wherein $R_7$ is as defined for any of the embodiments of formula (C) or (D) above.

In a preferred embodiment, the compound of formula (C) or (D) is a compound (TR-A):

or a pharmaceutically acceptable salt thereof. In some embodiments, the compound (TR-A) is (TR2-A) or (TR3-A).

In a third aspect, the present invention provides a pharmaceutical composition according to any embodiment of the first aspect of the invention, or a compound according to any embodiment of the second aspect of the invention, for use in therapy.

In a fourth aspect, the present invention provides a pharmaceutical composition according to any embodiment of the first aspect of the invention, or a compound according to any embodiment of the second aspect of the invention, for use in the treatment or prevention of a disorder associated with $CCK_2$/gastrin receptors, a disorder caused by or associated with hypergastrinaemia or a gastric acid-related disorder. In some embodiments, a pharmaceutical composition or compound of the invention may be for use in the treatment or prevention of a disorder associated with $CCK_2$ receptor-bearing cells or failure or dysfunction of a physiological function in which gastrin is involved. A composition or compound of the invention may therefore be provided for use in the treatment or prevention of disorders including, without limitation, any one or more of gastric and duodenal ulcers, non-steroid anti-inflammatory drug (NSAID)-induced gastric ulceration, dyspepsia, gastro-oesophageal reflux disease (GORD), Barrett's oesophagus, ZES, hypergastrinaemia induced by a PPI or other acid-suppressant (including the effects of withdrawal) and conditions caused by hypergastrinaemia (such as bone loss, impaired bone quality and bone fractures), gastritis (including *H. pylori*-induced gastritis and complications of autoimmune chronic atrophic gastritis, such as gastric carcinoids and ECL-cell hyperplasia), neuroendocrine tumours (not limited to gastric carcinoids), parietal cell hyperplasia, fundic gland polyps, gastric cancer, colorectal cancer, medullary thyroid cancer, pancreatic cancer, and small cell lung cancer. The pharmaceutical compositions or compounds of the invention may be provided for use in treatment of tumours comprising $CCK_2$ receptor-bearing cells (e.g. tumours of the pancreas, stomach, colon or medullary thyroid, or other $CCK_2$ receptor-bearing tumours). The pharmaceutical compositions or compounds of the invention may also be provided for use in the prevention and/or treatment of a disorder induced by the failure of a physiological function associated with the central or peripheral $CCK_2$ receptor, for example anxiety, nociception, pain, drug addiction, analgesic dependence or analgesia withdrawal reactions. The pharmaceutical composition or compound may be provided for use by administration with an additional active agent, for example a cytotoxic agent or a tumour-specific antibody. Administration may be in a single dosage form or separate dosage forms, simultaneously, sequentially or separately.

In some embodiments, the pharmaceutical composition or compound of the invention is provided for use in the treatment or prevention of an acid-related disorder (for example, gastric and duodenal ulcers, gastritis, NSAID-induced gastric ulceration, GORD, Barrett's oesophagus, ZES, or dyspepsia) by administration in combination with a histamine $H_2$-receptor antagonist, PPI, potassium-competitive acid inhibitor or any other gastric acid suppressant. Administration may be in a single dosage form or separate dosage forms, simultaneously, sequentially or separately.

In some embodiments, the pharmaceutical composition or compound of the invention is provided for use in the treatment of a tumour of the pancreas, stomach, colon or medullary thyroid, or other $CCK_2$ receptor-bearing tumour, by administration in combination with a cytotoxic therapy or tumour-specific antibody. Administration may be in a single dosage form or separate dosage forms, simultaneously, sequentially or separately.

In some embodiments, the pharmaceutical composition or compound of the invention is provided for use in the treatment of pain by administration in combination with an analgesic. Administration may be in a single dosage form or separate dosage forms, simultaneously, sequentially or separately.

In some embodiments, the pharmaceutical composition or compound of the invention is provided for use in treating or preventing a disorder of bone (for example, bone loss, deterioration in bone quality, and bone fractures) caused by hypergastrinaemia, by administration of a pharmaceutical composition or compound of the invention either alone or in combination with a PPI, histamine $H_2$-receptor antagonist, potassium-competitive acid inhibitor or any other gastric acid suppressant. Administration may be in a single dosage form or separate dosage forms, simultaneously, sequentially or separately.

In a fifth aspect, the invention provides a method of treating or preventing a disorder associated with $CCK_2$/gastrin receptors, a disorder caused by or associated with hypergastrinaemia or a gastric acid-related disorder in a subject in need thereof, the method comprising administration of a therapeutically effective amount of a pharmaceutical composition according to any embodiment of the first aspect of the invention, or a compound according to any embodiment of the second aspect of the invention, to said subject. Such disorders include disorders associated with $CCK_2$ receptor-bearing cells or failure or dysfunction of a physiological function in which gastrin is involved. Accordingly, disorders that can be treated and/or prevented by a method of the invention include, without limitation, any one or more of gastric and duodenal ulcers, NSAID-induced gastric ulceration, dyspepsia, GORD, Barrett's oesophagus, ZES, hypergastrinaemia induced by a PPI or other acid-suppressant (including the effects of withdrawal) and conditions caused by hypergastrinaemia (such as bone loss, impaired bone quality and bone fractures), gastritis (including *H. pylori*-induced gastritis and complications of autoimmune chronic atrophic gastritis, such as gastric carcinoids and ECL-cell hyperplasia), neuroendocrine tumours (not limited to gastric carcinoids), parietal cell hyperplasia, fundic gland polyps, gastric cancer, colorectal cancer, medullary thyroid cancer, pancreatic cancer, and small cell lung cancer. Disorders that can be treated by a method of the invention include tumours comprising $CCK_2$ receptor-bearing cells (e.g. tumours of the pancreas, stomach, colon or medullary thyroid, or other $CCK_2$ receptor-bearing tumours). Disorders that can be treated by a method of the invention also include disorders associated with the dysfunction of a physiological function controlled by the central or peripheral $CCK_2$ receptor, for example anxiety, nociception, pain, drug addiction, analgesic dependence and analgesia withdrawal reactions. Accordingly, in some embodiments, the invention provides a method of treating or preventing a disorder associated with the dysfunction of a physiological function controlled by the central or peripheral $CCK_2$ receptor, for example anxiety, nociception, drug addiction, analgesic dependence or an analgesia withdrawal reaction in a subject in need thereof, the method comprising administration of a therapeutically effective amount of a pharmaceutical composition according to any embodiment of the first aspect of the invention, or a compound according to any embodiment of the second aspect of the invention, to said subject.

In some embodiments, the invention provides a method of treating or preventing an acid-related disorder (for example, gastric and duodenal ulcers, gastritis, NSAID-induced gastric ulceration, GORD, Barrett's oesophagus, ZES, or dyspepsia) in a subject in need thereof, comprising administration of a therapeutically effective amount of a pharmaceutical composition of the invention, or a compound according to any embodiment of the second aspect of the invention, in combination with a histamine $H_2$-receptor antagonist, PPI, potassium-competitive acid inhibitor or any other gastric acid suppressant. Administration may be in a single dosage form or separate dosage forms, simultaneously, sequentially or separately.

In some embodiments, the invention provides a method of treating a tumour of the pancreas, stomach, colon or medullary thyroid, or other $CCK_2$ receptor-bearing tumour in a subject in need thereof, comprising administration of a therapeutically effective amount of a pharmaceutical composition or compound of the invention in combination with a cytotoxic therapy or tumour-specific antibody. Administration may be in a single dosage form or separate dosage forms, simultaneously, sequentially or separately.

In some embodiments, the invention provides a method of treating pain in a subject in need thereof, comprising administration of a therapeutically effective amount of a pharmaceutical composition or compound of the invention in combination with an analgesic. Administration may be in a single dosage form or separate dosage forms, simultaneously, sequentially or separately.

In some embodiments, the invention provides a method of treating or preventing a disorder of bone (for example, bone loss, deterioration in bone quality, and bone fractures) caused by hypergastrinaemia in a subject in need thereof, comprising administration of a therapeutically effective amount of a pharmaceutical composition or compound of the invention either alone or in combination with a PPI, histamine $H_2$-receptor antagonist, potassium-competitive acid inhibitor or any other gastric acid suppressant. Administration may be in a single dosage form or separate dosage forms, simultaneously, sequentially or separately.

In a sixth aspect, the invention provides use of a compound of formula (A) or (B), or a pharmaceutically acceptable salt, ester, thioester, salt of an ester or thioester, or prodrug thereof, as defined in respect of the first aspect of the invention in the manufacture of a medicament for the treatment or prevention of a disorder mediated via $CCK_2$/gastrin receptors, a disorder caused by or associated with hypergastrinaemia or a gastric acid-related disorder. In some embodiments, the compound is a compound of formula (C) or (D) as defined in respect of the first and second aspects of the invention. Preferably, the compound of formula (A) or (B) is a compound (TR):

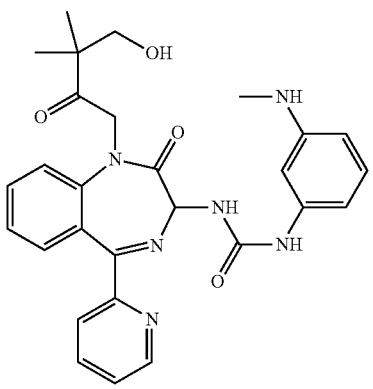

(TR)

or a pharmaceutically acceptable salt, ester, salt of an ester, or prodrug thereof, for example a compound of formula (TR-A):

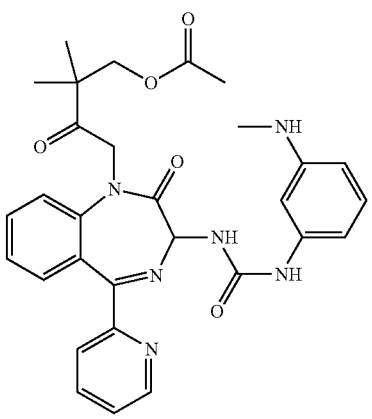

(TR-A)

or a pharmaceutically acceptable salt thereof.

In a seventh aspect, the invention provides a compound of formula (A) or (B), or a pharmaceutically acceptable salt, ester, thioester, salt of an ester or thioester, or prodrug thereof, as defined in respect of the first aspect of the invention for use as a medicament. In some embodiments, the compound is a compound of formula (C) or (D) as defined in respect of the first or second aspects of the invention. Preferably, the compound of formula (A) or (B) is a compound (TR):

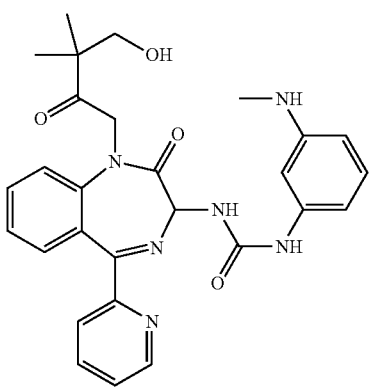

(TR)

or a pharmaceutically acceptable salt ester, salt of an ester, or prodrug thereof, for use as a medicament. For example, the compound may be a compound of formula (TR-A):

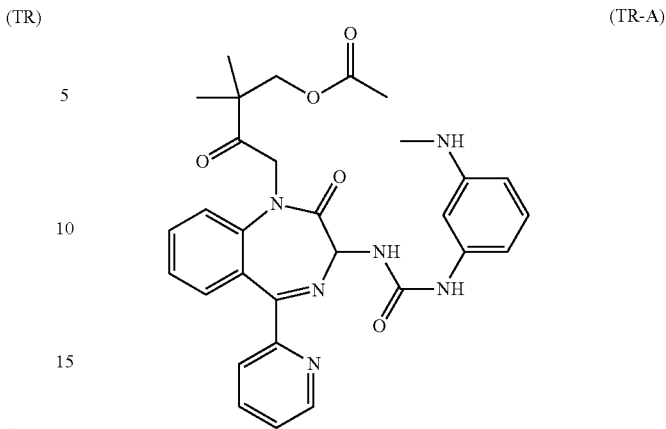

(TR-A)

or a pharmaceutically acceptable salt thereof.

The medicament may be for use for the prevention or treatment of a disorder mediated via $CCK_2$/gastrin receptors, a disorder caused by or associated with hypergastrinaemia or a gastric acid-related disorder, as described herein.

In an eighth aspect, the invention provides an isolated compound of formula (A) or (B), or a pharmaceutically acceptable salt, ester, thioester, salt of an ester or thioester, or prodrug thereof, as defined in respect of the first aspect of the invention. Preferably, the isolated compound of formula (A) or (B) is an isolated compound (TR):

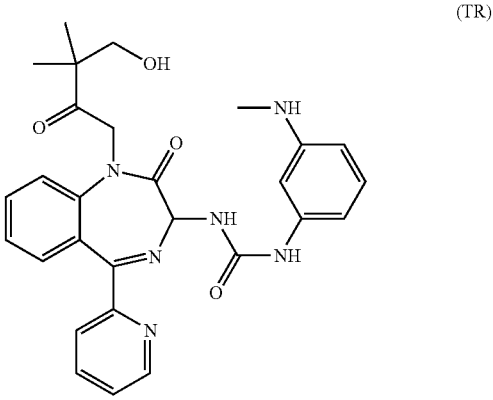 [SMILES: CNc1cccc(NC(=O)NC2N=C(c3ccccn3)c3ccccc3N(CC(=O)C(C)(C)CO)C2=O)c1]

(TR)

or a pharmaceutically acceptable salt ester, salt of an ester, or prodrug thereof.

In any aspect of the invention, the compound of formula (A), (B), (C), (D) or (E) may be provided as a racemic mixture of enantiomers, a non-racemic mixture of the enantiomers or as a single enantiomer in optically pure form. In any aspect of the invention, (TR) may be provided as the racemic mixture (TR1) of the enantiomers (TR2) and (TR3), a non-racemic mixture of the enantiomers (TR2) and (TR3) or as a single enantiomer (TR2 or TR3) in optically pure form. In any aspect of the invention, (TR-A) may be provided as a racemic mixture (TR1-A) of the enantiomers (TR2-A) and (TR3-A), a non-racemic mixture of the enantiomers (TR2-A) and (TR3-A) or as a single enantiomer (TR2-A) or (TR3-A) in optically pure form.

In a ninth aspect, the invention provides a process for preparing a compound of formula

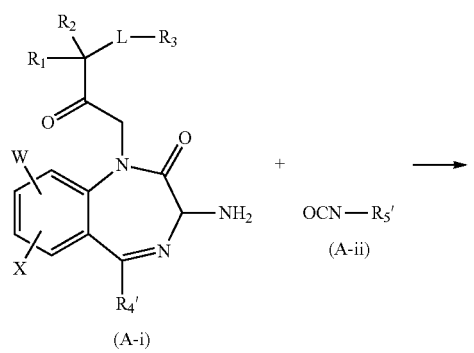

(A-i)  +  OCN—R₅'  (A-ii)

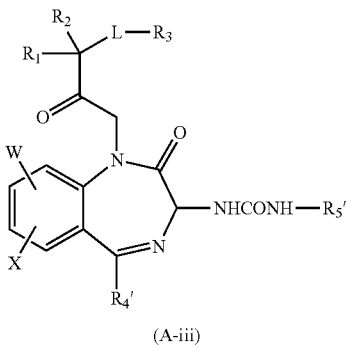

(A-iii)

said process comprising coupling a compound of formula (A-i) with a compound of formula (A-ii) to form a compound of formula (A-iii); wherein, $R_1$, $R_2$, L, W and X are as defined herein in relation to the first and second aspects of the invention, $R_3$ is —$OR_6$, —$SR_6$, —$OC(O)R_7$ or —$SC(O)R_7$, $R_6$ is hydrogen or alkyl (preferably methyl), $R_7$ is an optionally substituted aliphatic, heteroaliphatic, aromatic or heteroaromatic moiety; and $R_4'$ and $R_5'$ are, independently, a monocyclic aryl or heteroaryl, optionally substituted with one or more substituents independently selected from halo, hydroxy, amino, nitro, carboxyl, carboxamido, cyano, —$SO_3H$, and optionally substituted $C_{1-5}$ alkyl, $C_{1-8}$ alkoxy, $C_{1-8}$ alkylamino or di($C_{1-8}$alkyl)amino; or a protected form thereof. Coupling may be carried out in the presence of an organic aprotic solvent. The solvent may, for example, be dichloromethane, acetonitrile, acetone, tetrahydrofuran, ethyl acetate, dimethylformamide or dimethyl sulfoxide, or a mixture thereof. It will be appreciated that embodiments described herein in relation to $R_4$ and $R_5$ in the first and second aspects of the invention apply mutatis mutandis to the $R_4'$ and $R_5'$.

In some embodiments, the process comprises coupling a compound of formula (C-i) with a compound of formula (A-ii) to form a compound of formula (C-iii).

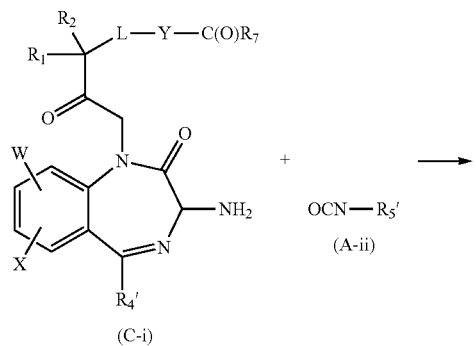

(C-i)  +  OCN—R₅'  (A-ii)

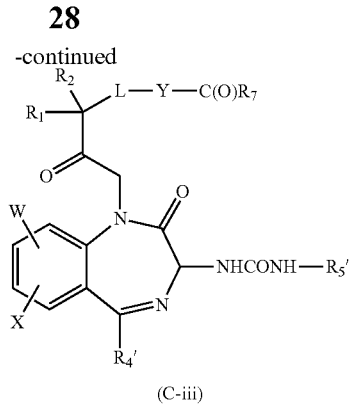

(C-iii)

Where $R_4'$ and/or $R_5'$ are provided as a protected form, the process may comprise the further step of deprotecting the compound of formula (A-iii) or (C-iii) to form a compound of formula (A) or (C)

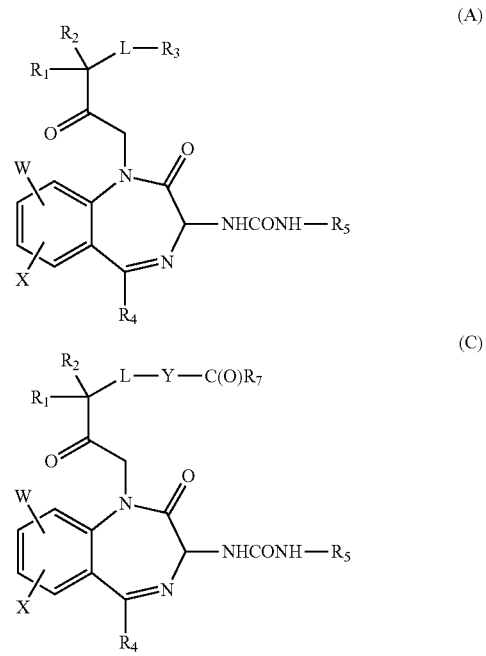

wherein, $R_1$ and $R_2$ are each, independently, H, $C_{1-3}$ aliphatic, halo, or $C_{1-3}$ haloaliphatic, or wherein $R_1$ and $R_2$ together with the intervening carbon atom to which they are bonded, form a $C_{3-6}$ carbocyclic moiety; L is a bond or $C_{1-3}$ alkylene; $R_3$ is —$OR_6$, —$SR_6$, —$OC(O)R_7$ or —$SC(O)R_7$; W and X are, independently, hydrogen, halo, $C_{1-8}$ alkyl or $C_{1-8}$ alkoxy; $R_4$ and $R_5$ are both, independently, a monocyclic aryl or heteroaryl, optionally substituted with one or more substituents independently selected from halo, hydroxy, amino, nitro, carboxyl, carboxamido, cyano, —$SO_3H$, and optionally substituted $C_{1-8}$ alkyl, $C_{1-8}$ alkoxy, alkylamino or di($C_{1-8}$ alkyl)amino; $R_6$ is hydrogen or alkyl (preferably methyl); and $R_7$ is an optionally substituted aliphatic, heteroaliphatic, aromatic or heteroaromatic moiety.

Where the process forms a compound of formula (A) in which $R_3$ is —$OC(O)R_7$ or —$SC(O)R_7$, or a compound of formula (C), the process may optionally comprise the additional step of converting —$OC(O)R_7$ or —$SC(O)R_7$ to —OH or —SH by exposure to acid or base. For example, this step may involve exposure to $K_2CO_3$, in methanol and water.

In some embodiments, the compound of formula (C-i) is a compound of formula (C-i-2), which may be coupled with a compound of formula (A-ii) to form a compound of formula (C-iii-2):

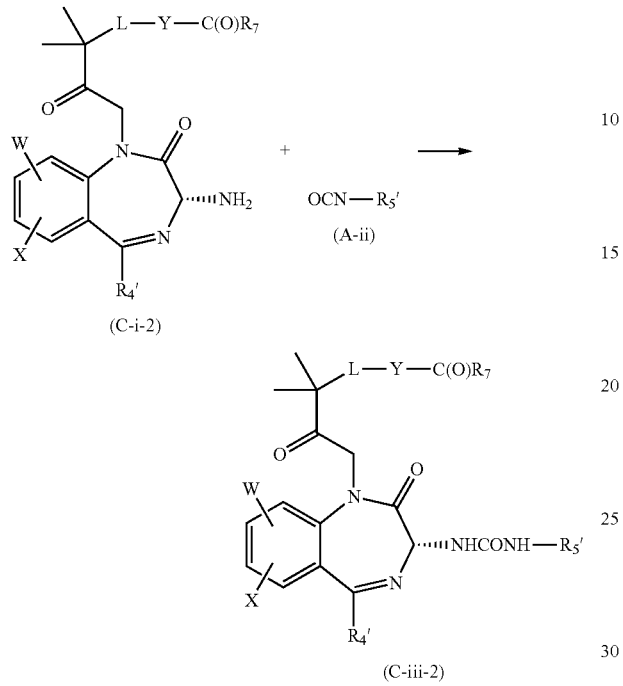

In some embodiments the compound of formula (A-i) is a compound of formula (A-i-a) (for example a compound of formula (A-i-b)), preferably a compound of formula (A-i-c):

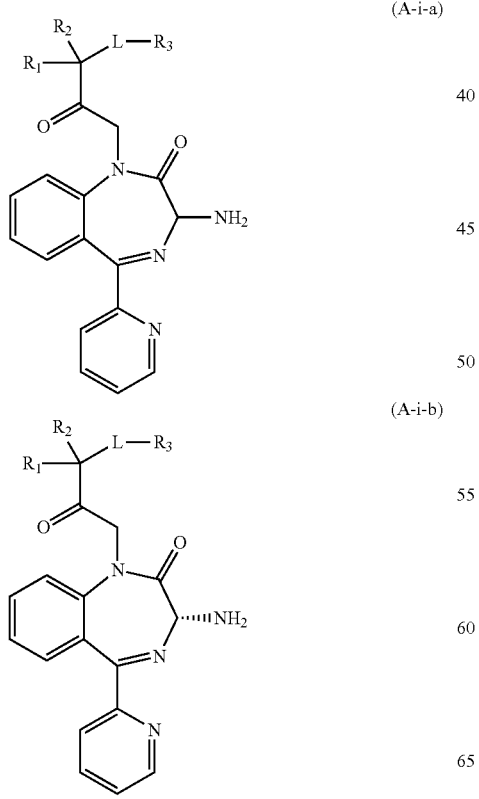

In some embodiments the compound of formula (C-i) is a compound of formula (C-i-a) (for example a compound of formula (C-i-b)), preferably a compound of formula (C-i-c), more preferably a compound of formula (C-i-d):

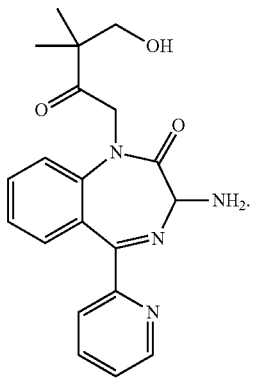
(C-i-a)

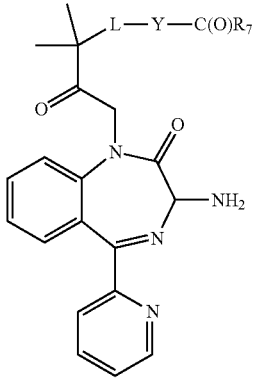
(C-i-b)

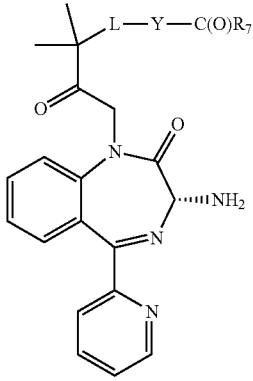
(C-i-c)

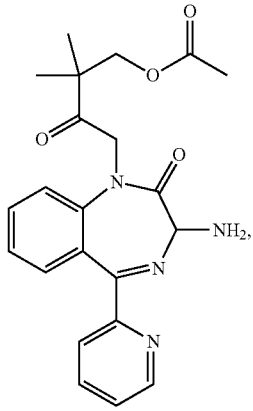
(A-i-c)

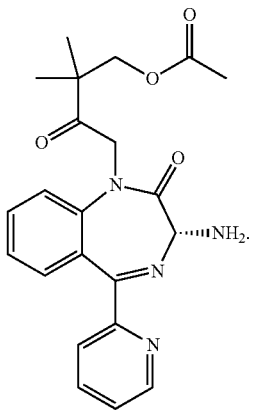

(C-i-d)

In some embodiments, the compound of formula (A-ii) is a compound of formula (A-ii-a):

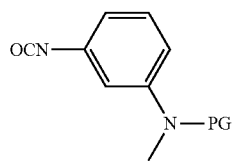

(A-ii-a)

wherein PG is a protecting group, preferably a Boc protecting group. Coupling of a compound of formula (C-i-a) or (C-i-d) with a compound of formula (A-ii-a), followed by deprotection, produces a compound of formula (TR-A) or (TR2-A), respectively. Coupling of a compound of formula (A-i-a) with a compound of formula (A-ii-a), followed by deprotection, produces a compound of formula (TR).

In some embodiments, where the compound of formula (C-i) is a compound of formula (C-i-2), the process may comprise chiral resolution of a compound of formula (C-i), in the form of a mixture of its enantiomers, e.g. a racemic mixture, to provide a compound of formula (C-i-2), wherein chiral resolution is carried out with a chiral acid in a solvent. In the chiral resolution, the chiral acid may, for example, be R-mandelic acid, R-camphor-10-sulfonic acid, or dibenzoyl D-tartaric acid, preferably R-mandelic acid. The solvent may be, for example, acetonitrile, isopropanol or ethyl acetate, preferably, acetonitrile. For example, the process may comprise the step of resolving racemic (C-i-a) to form (C-i-b), prior to coupling (C-i-d) with a compound of formula (A-ii-a) to form a compound of formula (TR2-A). Chiral resolution may involve formation of the respective chiral acid salt of a compound of formula (C-i-2) by exposure of the compound of formula (C-i) to a chiral acid in solvent. This may be followed by conversion of the salt to the free base compound of formula (C-i-2), for example using NaHCO$_3$. It will be appreciated that the (S)-enantiomer may also be produced by corresponding chiral resolution.

It will be appreciated that compounds of formulae (A-i), (A-iii), (C-i), (C-iii), (A-i-a), (A-i-c), (C-i-a) and (C-i-c) may be provided as a racemic mixture of enantiomers, a non-racemic mixture of the enantiomers or as a single enantiomer in optically pure form.

Embodiments described herein in relation to $R_1$, $R_2$, $R_3$, L, W, X, $R_4$, $R_5$, $R_6$ and $R_7$ for compounds of formulae (A), (B), (C), (D), (E), (F), (TR) and (TR-A) in the first and second aspects of the invention, apply mutatis mutandis to the ninth aspect of the invention.

In a tenth aspect, the invention provides an intermediate of formula (A-i), (C-i) or (C-i-2) as defined in relation to the ninth aspect of the invention. In some embodiments, the intermediate is a compound of formula (A-i-a), (A-i-b), (A-i-c), (C-i-a), (C-i-b), (C-i-c) or (C-i-d).

In an eleventh aspect, the invention provides a process for producing a compound of formula (C-i-2) wherein the process comprises chiral resolution of a compound of formula (C-i), in the form of a mixture of its enantiomers, e.g. a racemic mixture, the chiral resolution comprising exposing the compound of formula (C-i) to a chiral acid in a solvent. In some embodiments, the process comprises chiral resolution of compound (C-i-a) to produce compound (C-i-b). Preferably, the process comprises chiral resolution of compound (C-i-c) to produce compound (C-i-d). The chiral acid may, for example, be R-mandelic acid, R-camphor-10-sulfonic acid, or dibenzoyl D-tartaric acid, preferably R-mandelic acid. The solvent may be, for example, acetonitrile, isopropanol or ethyl acetate, preferably, acetonitrile. Chiral resolution may involve formation of the respective chiral acid salt of a compound of formula (C-i-2) by exposure of the compound of formula (C-i) to a chiral acid in solvent. This may be followed by conversion of the salt to the free base compound of formula (C-i-2), for example using NaHCO$_3$. It will be appreciated that the (S)-enantiomer may also be produced by corresponding chiral resolution.

BRIEF DESCRIPTION OF THE FIGURES

FIG. 1 shows a mean of H$^+$ concentration-time plots after the administration of (TR2-A) doses in combination with pentagastrin infusion.

DETAILED DESCRIPTION

The meanings of terms used in the specification of the present application will be explained below, and the present invention will be described in detail.

The term "aliphatic", as used herein, means a substituted or unsubstituted straight-chain, branched or cyclic hydrocarbon, which is completely saturated or which contains one or more units of unsaturation, but which is not aromatic. Aliphatic groups include substituted or unsubstituted linear, branched or cyclic alkyl, alkenyl, alkynyl groups and hybrids thereof, such as (cycloalkyl)alkyl, (cycloalkenyl)alkyl or (cycloalkyl)alkenyl. In various embodiments, an aliphatic group has 1 to 12, 1 to 8, 1 to 6, or 1 to 3 carbons. For example, $C_{1-3}$ aliphatic encompasses straight chain and branched $C_{1-3}$ alkyl, alkenyl and alkynyl and cyclopropyl. The term "heteroaliphatic" means an aliphatic group in which one or more carbon atom is replaced by a heteroatom. The term "heteroatom" refers to nitrogen (N), oxygen (O), or sulfur (S).

The term "alkylene" refers to a bivalent alkyl group. An "alkylene" is a methylene or polymethylene group, i.e., —(CH$_2$)$_n$—, wherein n is a positive integer. An alkylene may be unsubstituted or substituted. A substituted alkylene is an alkylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "carbocyclic moeity" refers to a cyclic aliphatic group and includes, for example, cycloalkyl moieties.

The term "aryl" refers to a $C_{6-14}$ (preferably $C_{6-10}$) aromatic hydrocarbon, comprising one to three rings, each of which is optionally substituted. Aryl groups include, without limitation, phenyl, naphthyl, and anthracenyl. In some embodiments, two adjacent substituents on an aryl ring, taken together with the intervening ring atoms, form an optionally substituted fused 5- to 6-membered aromatic or 4- to 8-membered non-aromatic ring having 0-3 ring heteroatoms selected from the group consisting of N, O and S. Thus, the term "aryl", as used herein, includes groups in which an aromatic ring is fused to one or more heteroaromatic, cycloaliphatic, or heterocyclic rings, where the radical or point of attachment is on the aromatic ring.

The terms "heteroaryl" and "heteroar-" refer to an aromatic group having 5 to 14 ring atoms, preferably 5, 6, 9, or 10 ring atoms and having, in addition to carbon atoms, from one to four heteroatoms as ring atoms. The term "heteroatom" refers to N, O, or S. In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of N, O and S. Thus, the terms "heteroaryl" and "heteroar-", as used herein, also include groups in which a heteroaromatic ring is fused to one or more aromatic, cycloaliphatic, or heterocyclic rings, where the radical or point of attachment is on the heteroaromatic ring.

As used herein, "halo" refers to fluoro, chloro, bromo or iodo.

As used herein, "haloaliphatic" refers to an aliphatic moiety as defined above, substituted by one or more halo moieties.

As used herein, "alkoxy" refers to a —O-alkyl moiety. The alkyl is as defined herein and, accordingly, may optionally be substituted as defined herein for optional substituents of an aliphatic moiety.

As used herein, "carboxamido" refers to a —C(O)NR$_2$ moiety, wherein each R is, independently, H or aliphatic, preferably H.

As used herein, "amino" refers to —NH$_2$, "alkylamino" refers to —NHalkyl and "dialkylamino" refers to —N(alkyl)$_2$, wherein each alkyl may be the same or different.

As used herein, the term "comprises" means "includes, but is not limited to."

The term "substituted", as used herein, means that a hydrogen radical of a designated moiety is replaced with the radical of a specified substituent, provided that the substitution results in a stable or chemically feasible compound. The phrase "one or more substituents", as used herein, refers to a number of substituents that equals from one to the maximum number of substituents possible based on the number of available bonding sites. Unless otherwise indicated, where multiple substituents are present, substituents may be either the same or different.

An aryl or heteroaryl group may be optionally substituted. Suitable substituents on the unsaturated carbon atom of an aryl or heteroaryl group include halo, —NO$_2$, —CN, —R', —C(R)═C(R)$_2$, —OR', —SR', —S(O)R', —SO$_2$R', —SO$_3$R', —SO$_2$N(R)$_2$, —N(R)$_2$, —NR'C(O)R', —NaC(O)N(R)$_2$, —NR'CO$_2$R', —NRSO$_2$R', —NRSO$_2$N(R)$_2$, —O—C(O)R', —O—CO$_2$R', —OC(O)N(R), —C(O)R', —CO$_2$R', —C(O)N(R)$_2$, —P(O)(R)$_2$, —P(O)(OR)$_2$, —O—P(O)—OR', wherein R', independently, is hydrogen or an optionally substituted aliphatic, heteroaliphatic, aromatic or heteroaromatic moiety, or two occurrences of a are taken together with their intervening atom(s) to form an optionally substituted 5-7-membered aromatic, heteroaromatic, cycloaliphatic, or heterocyclic ring.

An aliphatic or heteroaliphatic group, including carbocyclic or heterocyclic rings, may be "optionally substituted". Unless otherwise defined, suitable substituents on the saturated carbon of an optionally substituted aliphatic or heteroaliphatic group, are selected from those listed above for the unsaturated carbon of an aryl or heteroaryl group and additionally include the following: ═O, ═S, ═C(R")$_2$, where R" is hydrogen or an optionally substituted $C_{1-6}$ aliphatic group.

In addition to the substituents defined above, optional substituents on the nitrogen of a non-aromatic heterocyclic ring also include and are generally selected from —N(R)$_2$, —C(O)R, —C(O)OR, —S(O)$_2$R, —S(O)$_2$N(R)$_2$, wherein each R is defined above. A ring nitrogen atom of a heteroaryl or non-aromatic heterocyclic ring also may be oxidized to form the corresponding N-hydroxy or N-oxide compound.

As used herein, a "protected form" of a compound refers to a compound in which a functional moiety is protected by a protecting group. The functional moiety to be protected may be hydroxyl, carboxyl, amino, or alkylamino. Thus, a protected form as used herein may comprise a protected hydroxyl, protected carboxyl, or a protected amino or alkylamino moiety. Protection involves temporary blocking of the moiety so that a reaction can be carried out selectively at another reactive site in a multifunctional compound. A protected amino or alkylamino may be protected by a protecting group, selected from protecting groups including, but not limited to, carbamates (including methyl, ethyl and substituted ethyl carbamates (e.g., Troc), carbobenzyloxy (Cbz), tert-butyloxycarbonyl (BOC), 9-fluorenylmethyloxycarbonyl (FMOC)), p-methoxybenzyloxycarbonyl (Moz or MeOZ), acetyl (Ac), benzoyl (Bz), benzyl (Bn), p-methoxybenzyl (PMB) 3,4-dimethoxybenzyl (DMPM), p-methoxyphenyl (PMP), succinyl (Suc), methoxysuccinyl (MeOSuc), formyl, urethane protecting groups, tosyl (Ts), other sulfonamides (e.g. Nosyl & Nps). For example, in certain embodiments, as detailed herein, certain exemplary oxygen protecting groups are utilized. A protected hydroxyl or carboxyl may be protected by an oxygen protecting group, selected from protecting groups including, but not limited to, acetyl (Ac), benzoyl (Bz), benzyl (Bn), pivaloyl (Piv), methyl ethers, substituted methyl ethers (e.g., MOM (methoxymethyl ether), β-methoxyethoxymethyl ether (MEM), MTM (methylthiomethyl ether), BOM (benzyloxymethyl ether), p-methoxybenzyl (PMB), PMBM (p-methoxybenzyloxymethyl ether)), substituted ethyl ethers, ethoxyethyl ethers, substituted benzyl ethers, methoxytrityl (MMT), tetrahydropyranyl (THP), trityl (Tr), silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether, TOM (tri-iso-propylsilyloxymethyl)), esters (e.g., formate, acetate, benzoate (Bz), trifluoroacetate, dichloroacetate), carbonates, cyclic acetals and ketals. It will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

An "organic aprotic solvent" is used herein in accordance with standard terminology in the art to refer to an organic solvent which is incapable of acting as a proton donor. Aprotic solvents include, but are not limited to, dichloromethane, tetrahydrofuran, ethyl acetate, acetonitrile, dimethylformamide, dimethyl sulfoxide, acetone, hexane, pentane, benzene, toluene, 1,4-dioxane, diethyl ether, and chloroform.

Compounds of formula (A), (B), (C), (D), (E), (F), (TR), (TR2), (TR-A) and (TR2-A), and embodiments thereof as described herein, are $CCK_2$/gastrin receptor antagonists. Pharmaceutical compositions and compounds of the present invention are useful for the prevention and/or treatment of disorders associated with $CCK_2$/gastrin receptors, disorders caused by or associated with hypergastrinaemia and gastric acid-related disorders. Such disorders include disorders associated with $CCK_2$ receptor-bearing cells or failure or dysfunction of a physiological function in which gastrin is involved. Accordingly, examples of disorders that can be treated and/or prevented include, without limitation, any one or more of gastric and duodenal ulcers, NSAID-induced gastric ulceration, dyspepsia, GORD, Barrett's oesophagus, ZES, hypergastrinaemia induced by a PPI or other acid-suppressant (including the effects of withdrawal) and conditions caused by hypergastrinaemia (such as bone loss, impaired bone quality and bone fractures), gastritis (including *H. pylori*-induced gastritis and complications of autoimmune chronic atrophic gastritis, such as gastric carcinoids and ECL-cell hyperplasia), neuroendocrine tumours (not limited to gastric carcinoids), parietal cell hyperplasia, fundic gland polyps, gastric cancer, colorectal cancer, medullary thyroid cancer, pancreatic cancer, and small cell lung cancer. The pharmaceutical compositions of the invention are also useful for the prevention and/or treatment of disorders induced by the dysfunction of a physiological function controlled by the central or peripheral $CCK_2$ receptor, for example anxiety, nociception, pain, drug addiction, analgesic dependence and analgesia withdrawal reactions.

Compositions of the invention, when used for preventing or treating a disorder, may be administered in an "effective amount". By an "effective amount" it is meant a "therapeutically effective amount", namely an amount of compound sufficient, upon single dose or multiple dose administration, to cause a detectable decrease in disease severity, to prevent advancement of a disease or alleviate disease symptoms beyond that expected in the absence of treatment. A subject to be treated in accordance with a method of treatment of the invention is preferably a human subject.

Compositions of the invention are useful for reducing the severity of symptoms of any of the above disorders to be treated. Compositions of the invention are also useful for administration to patients susceptible to, at risk of, or suffering from, any of the above disorders. Compositions useful for prevention of the above disorders are not required to prevent absolutely occurrence of the disorder in all cases, but may prevent or delay onset of the disorder when administered to a patient susceptible to or at risk of the disorder. One or more of the above disorders may be present in a subject in combination and, accordingly, a pharmaceutical composition of the invention may treat one or more of the above disorders in combination.

Compounds of formula (A), (B), (C), (D), (E), (F), (TR) and (TR-A), and embodiments thereof as described herein, have at least one chiral carbon atom and may have more than one chiral carbon atom. The invention includes any enantiomeric form, at any level of optical purity, and mixtures thereof, both racemic and non-racemic. Accordingly, all stereoisomeric forms of the compounds disclosed herein form part of the invention. For example, the compound (TR) has a chiral carbon atom and the invention is understood to include both enantiomeric forms, at any level of optical purity, and mixtures thereof, both racemic and non-racemic. An optically pure form of an enantiomer as referred to herein has an enantiomeric excess (ee) of at least 90%, preferably at least 95%, more preferably at least 98%, and even more preferably at least 99%. ee may be assessed, for example, by chiral HPLC.

The compounds disclosed herein can exist in unsolvated as well as solvated forms for example with pharmaceutically acceptable solvents such as water, ethanol, and the like, and it is intended that the invention embrace both solvated and unsolvated forms. The compounds of formula (A), (B), (C), (D), (E), (F), (TR), (TR2), (TR-A) and (TR2-A), and embodiments thereof as described herein, their enantiomers and mixtures thereof, may be provided as the free compound or as a suitable salt or hydrate thereof. Salts should be those that are pharmaceutically acceptable, and salts and hydrates can be prepared by conventional methods, such as contacting a compound of the invention with an acid or base whose counterpart ion does not interfere with the intended use of the compound. Examples of pharmaceutically acceptable salts include hydrohalogenates, inorganic acid salts, organic carboxylic acid salts, organic sulphonic acid salts, amino acid salt, quaternary ammonium salts, alkaline metal salts, alkaline earth metal salts and the like. Basic compounds may form non-toxic acid addition salts with various inorganic and organic acids, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, toluenesulfonate and pamoate salts. Acidic compounds may form salts with various pharmacologically acceptable cations, including alkali metal or alkaline earth metal salts, particularly calcium, magnesium, sodium, lithium, zinc, potassium, and iron salts. Compounds that include a basic or acidic moiety may also form pharmaceutically acceptable salts with various amino acids.

The term "prodrug" refers to a compound that is transformed in vivo to yield a disclosed compound or pharmaceutically acceptable salt, by various mechanisms, for example by esterase, amidase, phosphatase, oxidative and/or reductive metabolism.

An ester or thioester of a compound of formula (A), (B) or (TR) is a compound in which the H of $R_3$ (—OH or —SH) is replaced by a moiety —C(O)R, wherein R is an optionally substituted aliphatic, heteroaliphatic, aromatic or heteroaromatic moiety. A prodrug can also be formed by the replacement of the hydrogen atom of the —OH or —SH group of $R_3$ with a group such as —P(O)(OH)$_2$, —P(O)(O($C_{1-6}$) alkyl)$_2$, an alkylcarbonyloxyalkyl (e.g. ($C_{1-6}$) alkylcarbonyloxymethyl, 1-methyl-1-(($C_{1-6}$) alkylcarbonyloxy)ethyl, ($C_{1-6}$) alkoxycarbonyloxymethyl), N—($C_{1-6}$) alkoxycarbonylaminomethyl, succinoyl, or a α-aminoalkylcarbonyl (e.g. a naturally occurring L-amino acid). A prodrug can be formed from an amine functional group, for example, by creation of an amide or carbamate, an N-alkylcarbonyloxyalkyl derivative, an (oxodioxolenyl)methyl derivative, an N-Mannich base, imine or enamine.

The invention includes the provision of compounds as described herein in substantially amorphous or substantially crystalline form. For example, the invention encompasses compound (TR2-A) in substantially amorphous or substantially crystalline form. "Substantially crystalline" and "substantially amorphous" refers to a compound that may be at least a particular weight percent crystalline or amorphous, respectively. In some embodiments, substantially crystalline or substantially amorphous refers to compounds that are at least 70%, at least 80%, at least 90%, or at least 95% crystalline or amorphous, respectively.

A pharmaceutical composition of the invention may additionally comprise one or more pharmaceutically acceptable excipients, for example pharmaceutically acceptable carriers, diluents, preserving agents, solubilising agents, stabilising agents, disintegrating agents, binding agents, lubricating agents, wetting agents, emulsifiers, sweeteners, colourants, odourants, salts, buffers, coating agents and antioxidants. Suitable excipients and techniques for formulating pharmaceutical compositions are well known in the art (see, e.g. *Remington: The Science and Practice of Pharmacy*, 20th Ed., ed. A. Gennaro, Lippincott Williams & Wilkins, 2000). Suitable excipients include, without limitation, pharmaceutical grade starch, mannitol, lactose, corn starch, magnesium stearate, stearic acid, alginic acid, sodium saccharin, talcum, cellulose, cellulose derivatives (e.g. hydroxypropylmethylcellulose, carboxymethylcellulose) glucose, sucrose (or other sugar), sodium carbonate, calcium carbonate, magnesium carbonate, sodium phosphate, calcium phosphate, gelatin, agar, pectin, liquid paraffin oil, olive oil, alcohol, detergents, emulsifiers or water (preferably sterile).

A pharmaceutical composition may further comprise an adjuvant and/or one or more additional therapeutically active agent(s).

A pharmaceutical composition may be provided in unit dosage form, will generally be provided in a sealed container and may be provided as part of a kit. Such a kit would normally (although not necessarily) include instructions for use. It may include a plurality of said unit dosage forms.

A pharmaceutical composition may be adapted for administration by any appropriate route, for example by oral, buccal or sublingual routes or parenteral routes, including subcutaneous, intramuscular, intravenous, intraperitoneal, and intradermal, rectal and topical administration, and inhalation. Such compositions may be prepared by any method known in the art of pharmacy, for example by admixing the active ingredient with a excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example water or oils (e.g vegetable oils, liquid paraffin oil or olive oil), waxes, fats, semi-solid, or liquid polyols etc. For the preparation of solutions and syrups, excipients which may be used include for example water, polyols and sugars. For the preparation of suspensions, oils (e.g. vegetable oils) may be used to provide oil-in-water or water-in-oil suspensions.

Pharmaceutical compositions adapted for administration by inhalation include fine particle dusts or mists, which may be generated by means of various types of metered dose pressurised aerosols, nebulizers or insufflators.

Pharmaceutical compositions adapted for parenteral administration (e.g. subcutaneous, intramuscular, intravenous, intraperitoneal) include aqueous and non-aqueous sterile injection solutions which may contain anti-oxidants, buffers, bacteriostats and solutes which render the formulation substantially isotonic with the blood of the intended recipient; and aqueous and non-aqueous sterile suspensions which may include suspending agents, thickening agents and wetting agents. Excipients which may be used for injectable solutions include, for example, water, alcohols, polyols, glycerine and vegetable oils. Suitable aqueous vehicles include Ringer's solution and isotonic sodium chloride. Aqueous suspensions may, for example, include suspending agents such as cellulose derivatives, sodium alginate, gum tragacanth, polyvinylpyrrolidone and wetting agents such as lecithin. The compositions may be presented in unit-dose or multi-dose containers, for example, sealed ampoules and vials, and may be stored in a freeze-dried (lyophilized) condition requiring only the addition of the sterile liquid carrier, for example, water for injection, immediately prior to use. Extemporaneous injection solutions and suspensions may be prepared from sterile powders, granules and tablets.

In some embodiments, the pharmaceutical composition of the invention is a depot formulation, formulated to provide controlled drug release into the bloodstream over a period of, for example, weeks or months, depending on the exact formulation. A depot formulation may, for example, be a nanoparticulate formulation of nanoparticles comprising a compound of formula (A), (B), (C), (D), (E), (F), (TR), (TR2), (TR-A) or (TR2-A), or any embodiment thereof as described herein, and one or more excipients, for example, surface stabilisers, bulking agents or carriers, or a formulation comprising a compound of formula (A), (B), (C), (D), (E), (F), (TR), (TR2), (TR-A) or (TR2-A), or any embodiment thereof as described herein, enclosed in micellar nanoparticles. A depot formulation is usually injected subcutaneously or intramuscularly, to produce a reservoir of drug in the muscle or under the skin. A depot formulation is usually solid or oil-based.

Compositions of the invention, when used for preventing or treating a disorder, may be administered in an "effective amount". For use as a single monotherapy, by an "effective amount" it is meant a "therapeutically effective amount", namely an amount of compound sufficient, upon single dose or multiple dose administration, to cause a detectable decrease in disease severity, to prevent advancement of a disease or alleviate disease symptoms beyond that expected in the absence of treatment. In the case were the invention is used in combination with another agent by an "effective amount" is meant to be an amount sufficient in combination with another agent when given either by a single or multiple dose administration to cause a detectable decrease in disease severity, to prevent advancement of a disease or alleviate disease symptoms beyond that expected in the absence of treatment or treatment with the second agent when given alone. The "effective amount" when used as a monotherapy may or may not be the same as that in combination with a second agent.

Dosages of the substance of the present invention can vary between wide limits, depending upon a variety of factors including the disease or disorder to be treated, the age, weight and condition of the individual to be treated, the route of administration, etc. A physician will ultimately determine appropriate dosages to be used. Typically, however, the daily dosage (whether administered as a dose or multiple divided doses) adopted for each route of administration when a compound of the invention is administered will be 0.001 to 5,000 mg/day, usually 1 to 1,000 mg/day, more usually 2 to 200 mg/day, and even more usually 2 to 50 mg/day. A typical dose may be, expressed as dosage per unit body weight, between 0.01 µg/kg and 50 mg/kg, preferably between 10 µg/kg and 10 mg/kg, for example between 100 µg/kg and 2 mg/kg.

The following examples describe exemplary compounds of the invention, (TR), which includes the enantiomers (TR2) and (TR3) in optically pure form or any mixture of these enantiomers, and (TR2-A). These compounds are demonstrated to be $CCK_2$/gastrin receptor antagonists that exhibit favourable properties compared with those of YF476 for successful use as a medicament. These properties include improved solubility, bioavailability, stability in amorphous form, and selectivity for the $CCK_2$ receptor (over the $CCK_1$ receptor).

EXAMPLES

Abbreviations
DCM dichloromethane
DIPEA N,N'-diisopropylethyl amine
DMF N,N'-dimethylformamide
DMS dimethyl sulphate
GC gas chromatography
HPLC high performance liquid chromatography
MeI methyliodide
MTBE methyltert-butylether
THF tetrahydrofuran
TLC thin layer chromatography
UV ultra violet Gas chromatography was carried out on a Shimadzu GC2014. HPLC was carried out on an Agilent/HP 1100 reverse phase HPLC system. NMR spectra were recorded on a 400 Mz Bruker Avance 111 spectrometer with QNP (1H/13C/19F/31P/Cryoprobe) or 500 Mz Bruker Avance 111 HD spectrometer with dual (1H/13C). Elemental analysis (CHN) was performed on an Exeter Analytical CE-440 elemental analyser. XPRD spectra were obtained on a Pananalytical X'pert Pro diffractometer.

The following examples of the invention are provided to aid understanding of the invention but should not be taken to limit the scope of the invention. Unless otherwise described, reagents may be commercially available or prepared according to procedures in the literature.

Example 1

Synthesis of (TR1)

(TR1) was synthesised according to the Scheme 1 below. It will be appreciated that this scheme can be applied generally to the synthesis of compounds of formulae (A) and (B) by variation of the starting materials 3, 4 and 7, as appropriate.

Scheme 1

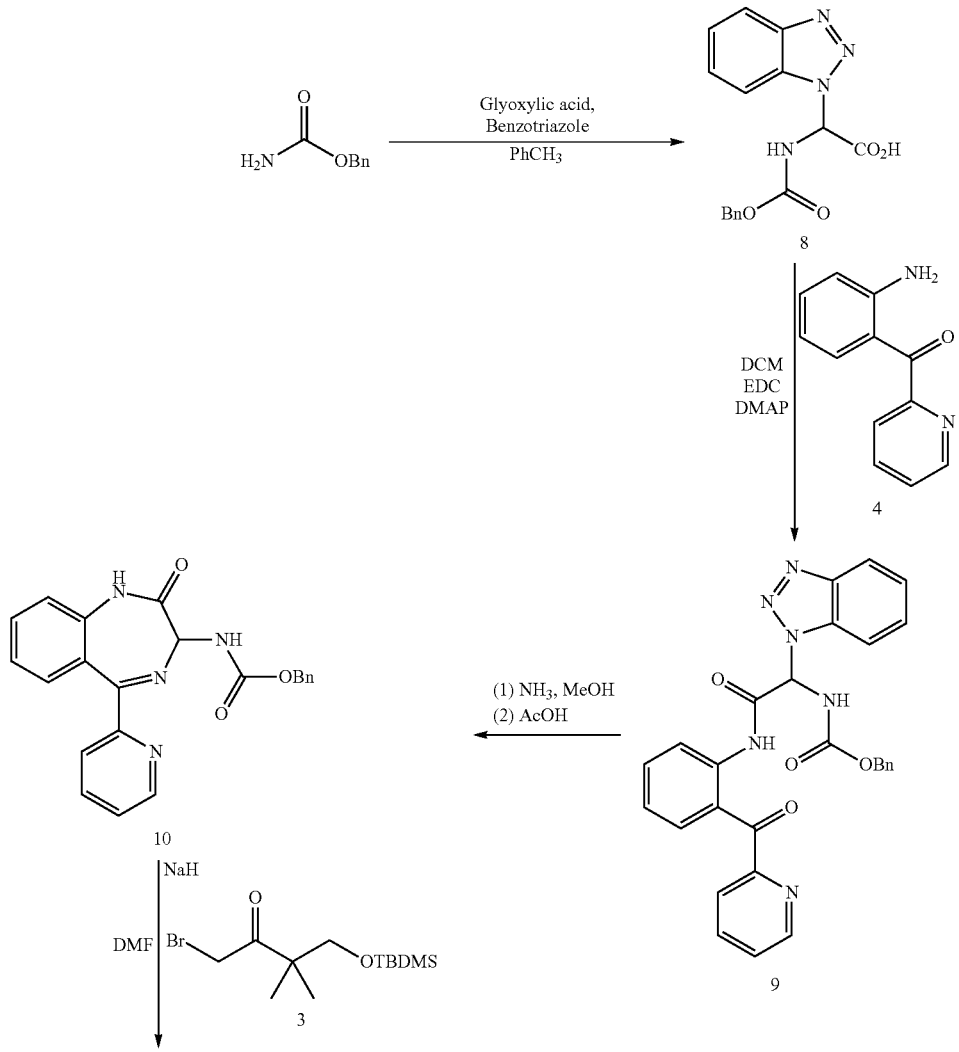

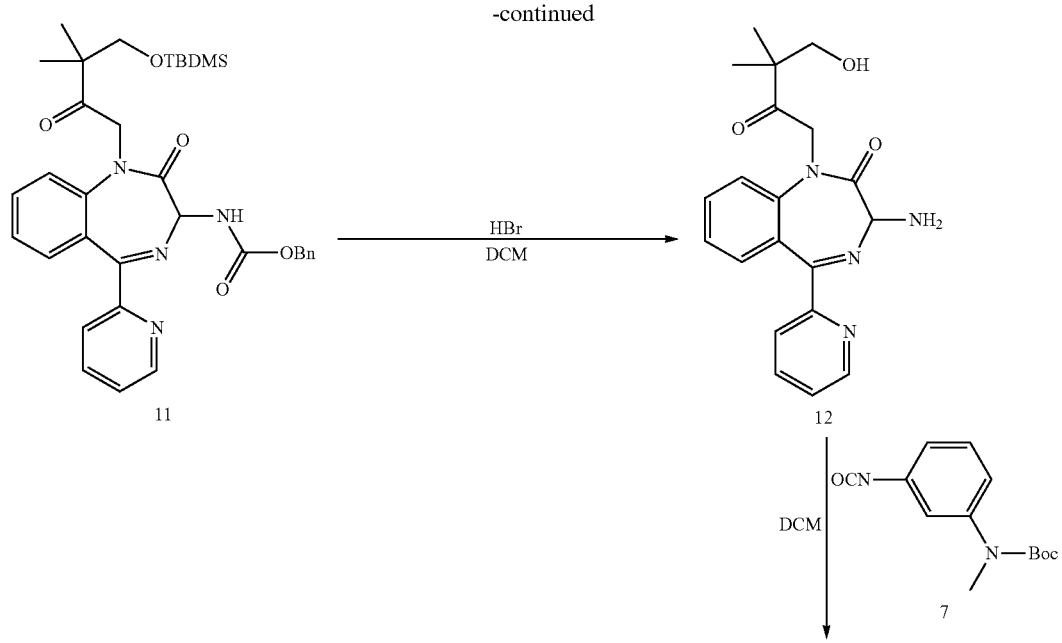
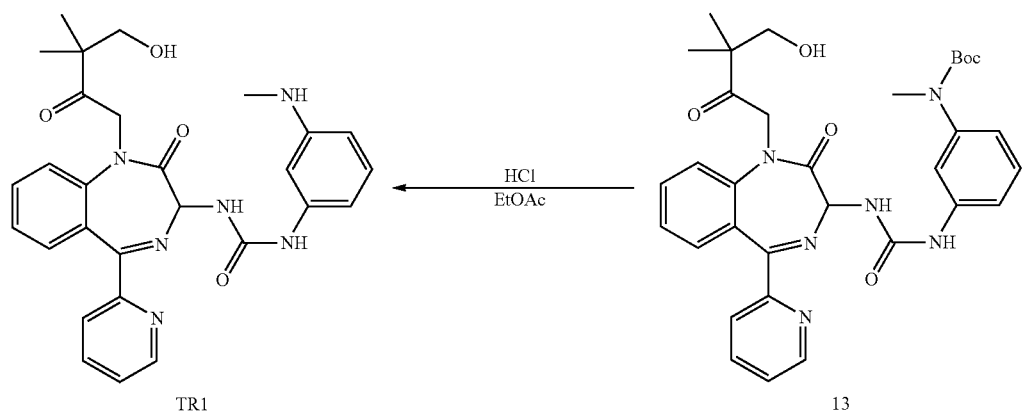
Reagents 3, 4 and 7, used in the synthesis of (TR1) were synthesised according to Scheme 2, 3 and 4 below:
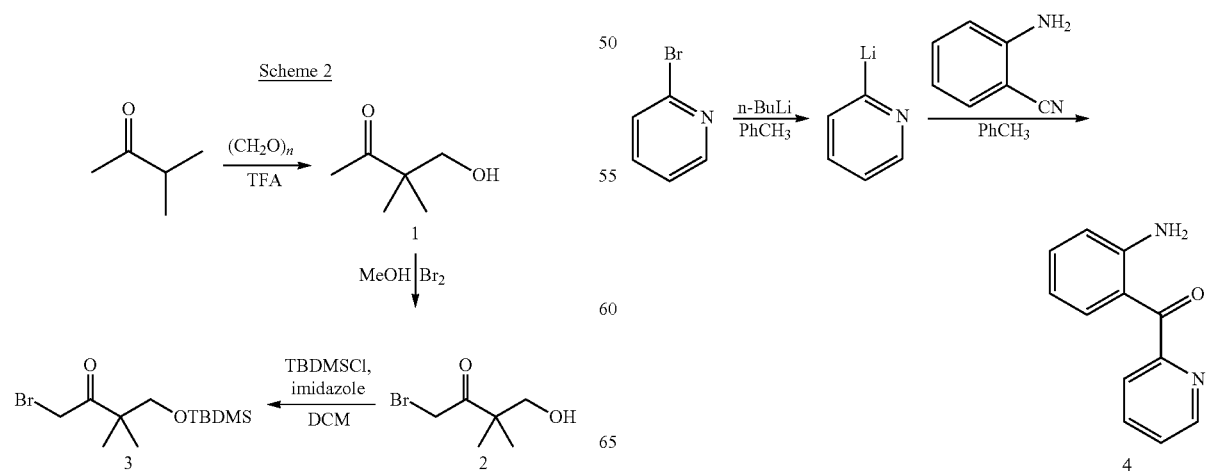

Scheme 4

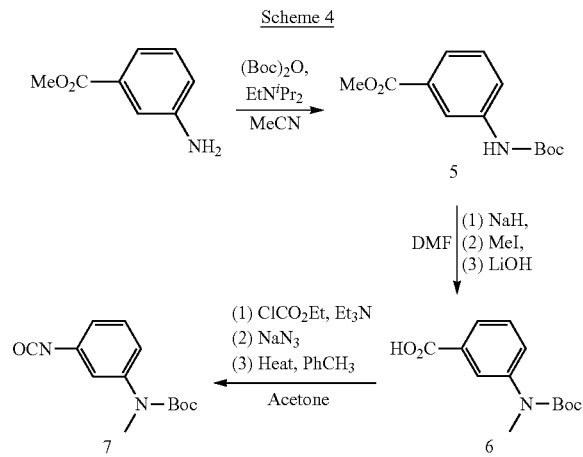

4-Hydroxy-3,3-dimethyl-2-butanone (1)

A mixture of 3-methyl-2-butanone (250 mL, 201.3 g, 2.34 mol), paraformaldehyde (84.2 g, 2.80 mol) and trifluoroacetic acid (365 mL, 4.77 mol) was heated at 90° C. under a nitrogen atmosphere for 7 hours (h). The resulting solution was cooled to 0-5° C. and neutralised with 2 M sodium hydroxide solution while maintaining the temperature at 0-5° C. The mixture was extracted with dichloromethane (3×1 L). The combined extracts were dried over anhydrous sodium sulphate and carefully stripped of solvent under vacuum to give an oil (260 g). The crude product was distilled at 90° C./50 mmHg through a 15 cm Fenski packed column to give two main fractions. Fraction 1 contained 71.5 g at 89.7% purity by gas chromatography (GC) and fraction 2 contained 75.7 g at 95.6% purity by GC. Fraction 2 was used in the next step.

1-Bromo-4-hydroxy-3,3-dimethyl-2-butanone (2)

Compound 1 (75.7 g, 652 mmol) was dissolved in dry methanol (400 mL) and cooled to −10° C. under a nitrogen atmosphere. Bromine (104.1 g, 652 mmol) was slowly added in the dark over 30 minutes (min), while maintaining the temperature at −10° C. The mixture was then stirred at 0° C. for 1 h. GC indicated that all but a trace of starting material had been consumed and a 95% product component had formed. Ethyl acetate (600 mL) was added and the mixture washed with cold water (600 mL). The aqueous layer was saturated with sodium chloride and extracted with diethyl ether (4×300 mL). The combined ethyl acetate and diethyl ether extracts were washed with 10% sodium carbonate solution (300 mL) and dried over anhydrous sodium sulphate. The solvents were removed under vacuum at 40° C. to give a pale orange/brown oil (118.6 g).

1-Bromo-4-(tert-butyl-dimethyl-silanyloxy)-3,3-dimethyl-2-butanone (3)

A solution of imidazole (43.0 g, 631 mmol) in dichloromethane (530 mL) was cooled to −15° C. to −20° C. while stirring under a nitrogen atmosphere. Compound 2 (102.7 g, 527 mmol) was added resulting in a clear solution. tert-Butyl-dimethyl-silyl chloride (91.1 g, 604 mmol) was slowly added while maintaining the temperature at −15° C. to −20° C. The mixture was then stirred at that temperature for 2.5 h. GC of a small water-quenched sample indicated that all of compound 2 had been consumed. Water (500 mL) was added and the lower organic layer removed and washed with more water (2×500 mL). The combined aqueous layers were back extracted with diethyl ether (2×800 mL). The combined dichloromethane and diethyl ether layers were dried over sodium sulphate and stripped of solvent under vacuum to give an oil (187 g). Chromatography through silica gel (3 kg), slurry-packed in 1% triethylamine in hexane, using 3% ethyl acetate in hexane as eluent provided the product. Good fractions were stripped of solvent under vacuum to give a near-colourless oil (113.8 g, 94.2% A by GC). Less pure fractions were also stripped of solvent to give a further 33 g (85% A by GC). $^1$H NMR (400 MHz, CDCl$_3$) δ 4.24 (s, 2H); 3.55 (s, 2H); 1.17 (s, 6H); 0.86 (s, 9H); 0.02 (s, 6H).

2-(2-Aminobenzoyl)pyridine (4)

2-Bromopyridine (307.6 g, 1.95 mol) was dissolved in toluene (1.2 L) and cooled to below −60° C. under a nitrogen atmosphere. n-Butyl lithium (1.6 M in hexanes; 1190 mL, 1.91 mol) was slowly added while maintaining the temperature below −60° C. The mixture was stirred for 15 min at that temperature. GC of a small quenched sample indicated that most of the 2-bromopyridine had been consumed. A solution of 2-aminobenzonitrile (100 g, 0.85 moles) in toluene (590 mL) was slowly added over a 20-minute period while maintaining a temperature below −60° C. The mixture was allowed to warm to room temperature overnight. The mixture was poured into 3 M hydrochloric acid (1.9 L) and stirred at room temperature for 1 h. The organic layer was removed and extracted with 1 M hydrochloric acid. The combined aqueous layers were washed with toluene (500 mL). The acidic solution was then basified to pH=9 with 25% ammonia solution while maintaining the temperature at about 0-5° C. The mixture was stirred for 1 h. at that temperature. The resulting precipitate was filtered, washed with water and dried to give a yellow/brown powder (171 g, GC=95.7% (total uncorrected area %) with a close 4.3% A after-peak). This was used directly in the next step.

Methyl 3-tert-butoxycarbonylamino-benzoate (5)

Di-tert-butyl dicarbonate (56 g, 257 mmol) was added to a solution of methyl 3-aminobenzoate (19.4 g, 128 mmol) and N,N-diisopropylethylamine (33.2 g, 257 mmol) in acetonitrile (150 mL) under a nitrogen atmosphere. The mixture was heated at 70° C. for 65 h (all weekend). Thin layer chromatography (TLC; elute 50% ethyl acetate in hexane) indicated that all but trace of methyl 3-aminobenzoate (R$_f$=0.65) had been consumed and a new component (R$_f$=0.8) had formed. The mixture was stripped under vacuum to remove acetonitrile and N,N-diisopropylethylamine resulting in an orange oil. The crude product was dissolved/triturated in hexane (3 volumes). The mixture was allowed to stand for 1 h at 4° C. (fridge) while the solid fully formed. The mixture was filtered and washed with a small amount of cold hexane. The solid was slurried in hexane (100 mL) for 1 h and then refiltered. The product was vacuum dried overnight to give a pale yellow/cream solid (19.5 g).

3-(N-tert-Butoxycarbonyl-N-methyl-amino)-benzoic acid (6)

Sodium hydride (60% disp. in oil; 7.72 g, 193 mmol) was added portionwise to a solution of compound 5 (19.4 g, 77.2 mmol) in dry N,N-dimethylformamide (250 mL) while maintaining a temperature below 10° C. The mixture was then allowed to warm to room temperature and stirred for 1 h. The mixture was re-cooled to 5° C. and methyl iodide (35.6 g, 251 mmol) added dropwise over a 30-minute period at that temperature. The mixture was then allowed to warm to room temperature and stirred for 2 h. TLC (elute 20% ethyl acetate in hexane) indicated that the reaction was complete. Both compound 5 and the methylated product had the same $R_f$=0.55 by TLC. However only compound 5 produced a coloured spot when developed with ninhydrin. Most of the N,N-dimethylformamide was removed under high vacuum and the residue partitioned between ethyl acetate (700 mL) and 5% sodium bicarbonate solution (250 mL). The organic layer was then washed with water (5×100 mL) before drying over anhydrous sodium sulphate and stripping to an oil (21.7 g). The oil was dissolved in methanol (420 mL) and cooled to 5° C. before adding 1 M aqueous lithium hydroxide solution (78 mL, 78 mmol). The mixture was then stirred at room temperature overnight. A further charge of 1 M lithium hydroxide solution (38 mL, 38 mmol) was added and the mixture stirred for 1 h. Most of the methanol was removed under vacuum before adding more water (400 mL) and washing with 33% ethyl acetate in hexane (150 mL then 75 mL). The stirred solution was very carefully adjusted to pH=4.0 using a calibrated pH meter and the slow dropwise addition of 5 M hydrochloric acid (over-acidification could result in removal of the BOC group). The mixture was extracted with ethyl acetate (2×200 mL). The combined organic layers were washed with brine (200 mL) and dried over anhydrous sodium sulphate before stripping to an oil (19.3 g). The oil was crystallised from 5% ethyl acetate in hexane (170 mL) while stirring at 0° C. for one hour. The product was filtered and washed with a small amount of cold hexane before drying under vacuum at 30° C. overnight to give a cream coloured powder (15.5 g). TLC (elute 50% toluene, 40% ethyl acetate, 10% formic acid solution) indicated the hydrolysed product at $R_f$=0.60 compared to the methylated ester intermediate at $R_f$=0.75.

3-[N-(tert-Butoxycarbonyl)-N-methyl-amino]phenyl isocyanate (7)

Triethylamine (7.05 g, 69.7 mmol) was added to a solution of compound 6 (15.2 g, 60.5 mmol) in acetone (120 mL) under a nitrogen atmosphere and the resulting solution cooled to 0-5° C. A solution of ethyl chloroformate (8.19 g, 75.5 mmol) in acetone (20 mL) was added dropwise while maintaining the temperature at 0-5° C. The mixture was stirred at this temperature for 30 min during which time a precipitate formed. A solution of sodium azide (5.9 g, 90.6 mmol) in water (20 mL) was added dropwise while maintaining the temperature at 0-5° C. The mixture was stirred at that temperature for 1 h. TLC (elute 50% toluene, 40% ethyl acetate, 10% formic acid solution) indicated that all of compound 16 ($R_f$=0.60) had been converted to the intermediate organic azide ($R_f$=0.75). The solution was poured into a stirred mixture of toluene (150 mL) and water (300 mL). The toluene layer was removed and washed with brine before drying over anhydrous sodium sulphate. Care was taken to not allow the solution to evaporate, resulting in a higher concentration, because organic azides can be violently thermally unstable. The dry toluene solution was heated to reflux (about 105° C.) under a nitrogen atmosphere for 2 h. Gas evolution was noted from a temperature of about 70° C. TLC indicated that all of the intermediate organic azide had been consumed. The solution was stripped to a yellow oil (13.8 g, GC purity=96.9% A) under high vacuum. This moisture sensitive material was stored under nitrogen at 4° C. until used.

$^1$H NMR (400 MHz, CDCl$_3$) δ 7.27-7.17 (under CHCl$_3$ peak, m); 7.08 (1H, d); 7.02 (1H, s); 6.89 (1H, m); 3.24 (3H, s); 1.46 (9H, s) ppm.

2-(Benzotriazol-1-yl)-2-(benzyloxycarbonylamino)-acetic acid (8)

A mixture of benzyl carbamate (82.1 g, 0.54 mol), glyoxylic acid monohydrate (50 g, 0.54 mol) and benzotriazole (64.7 g, 0.54 mol) in toluene (2.5 L) was heated at reflux with Dean and Stark water removal for 2 hours. A total of 23 mL of water was collected during the first hour before water evolution ceased. The mixture was allowed to cool to room temperature and the resulting solid filtered and washed with diethyl ether (200 mL). The damp filter cake was dried at 40° C./50 mmHg overnight to give a cream coloured powder (134.9 g).

Benzyl-(benzotriazol-1-yl-[2-(pyridine-2-carbonyl)-phenylcarbamoyl]-methyl)-carbamate (9)

A mixture of compound 4 (16.39 g, 82.7 mmol) and compound 8 (35.97 g, 110.2 mmol) in dichloromethane (300 mL) was cooled to 0° C. under a nitrogen atmosphere. 4-Dimethylaminopyridine (1.2 g, 9.8 mmol) followed by 1-(3-dimethylaminopropyl)-3-ethylcarbodiimide hydrochloride (23 g, 120.0 mmoles) was added to the mixture. The mixture was stirred for 10 min at 0° C. and then warmed to room temperature and stirred for a further 10 min. TLC (elute 50% ethyl acetate in hexane) indicated that all compound 4 ($R_f$=0.60) had been consumed and a new product ($R_f$=0.20) had formed. The mixture was stripped of solvent under vacuum and then partitioned between ethyl acetate (300 mL) and saturated sodium bicarbonate solution (300 mL). The organic layer was washed with brine (100 mL) and dried over anhydrous sodium sulphate before stripping to an oil (65 g). This crude material was used directly in the next step.

3-(Benzyloxycarbonyl)amino-2,3-dihydro-5-(2-pyridyl)-1H-1,4-benzodiazepin-2-one (10)

Crude compound 9 (65 g) was dissolved in ammonia saturated methanol (710 mL) and stirred at room temperature for 1 h. TLC (elute 50% ethyl acetate in hexane) indicated that compound 9 ($R_f$=0.20) had been consumed and the required product ($R_f$=0.15) had formed along with a by-product ($R_f$=0.5). The solution was stripped of solvent (and ammonia) under vacuum and dissolved in acetic acid (450 mL). This solution was stirred at room temperature for 4 h. The mixture was stripped under vacuum to remove most of the acetic acid and then partitioned between chloroform (300 mL) and 1 M sodium hydroxide solution (200 mL). The organic layer was washed with brine (200 mL) before drying over anhydrous sodium sulphate and stripping under vacuum to give an oil. The crude oil was dissolved in ethyl acetate (100 mL) and allowed to crystallise overnight. The mixture was filtered and washed with a small amount of ice cold ethyl acetate and the hexane (100 mL). The product was vacuum dried at 40° C. overnight to give a tan solid (15.9 g).

$^1$H NMR (400 MHz, CDCl$_3$) δ 8.67 (1H, br s); 8.61 (1H, d, J=4.1 Hz); 8.10 (1H, d, J=7.5 Hz); 7.84 (1H, dt, J=7.5 Hz and 1.4 Hz), 7.5-7.25 (8H, m); 7.20 (1H, t, J=7.5 Hz); 6.99

(1H, d, J=7.5 Hz); 6.65 (1H, d, J=8.2 Hz); 5.37 (1H, d, J=8.2 Hz); 5.16 (2H, d, J=2.7 Hz) ppm.

3-(Benzyloxycarbonyl)amino-1-[4-(tert-Butyl-dimethyl-silanyloxy)-3,3-dimethyl-2-oxo-butyl]-2,3-dihydro-5-(2-pyridyl)-1H-1,4-benzodiazepin-2-one (11)

Compound 10 (14.6 g, 37.8 mmol) was dissolved in dry N,N-dimethylformamide (150 mL) and cooled to 0° C. under a nitrogen atmosphere. Sodium hydride (60% dispersion in oil; 1.96 g, 49.0 mmol) was added in portion while maintaining the temperature at 0-5° C. The mixture was then allowed to warm to room temperature and stirred for one hour. A suspension formed during that period. The mixture was re-cooled to 0-5° C. and compound 3 (33.9 g, 109.6 mmol) added slowly while maintaining a temperature below 10° C. The mixture was then allowed to warm to room temperature and stirred for 1 h. A near-clear solution formed. TLC of a small quench sample (elute 50% ethyl acetate in hexane) indicated that compound 10 ($R_f$=0.15) had been consumed to form a new compound ($R_f$=0.55). The mixture was poured into saturated sodium bicarbonate solution (100 mL) and then stripped under high vacuum to remove most of the dimethylformamide (and water). The residue was dissolved in dichloromethane (150 mL) and washed with saturated sodium bicarbonate solution (5×150 mL). The organic layer was dried over anhydrous sodium sulphate and stripped to an oil. Chromatography through silica gel (500 g), slurry-packed with 1% triethylamine in hexane, using 20% rising to 50% ethyl acetate in hexane as eluent provided the product. Good fractions were stripped of solvent under vacuum to give a pale yellow solid. The product was triturated in hexane, filtered and dried to give a powder (19.2 g).

$^1$H NMR (400 MHz, CDCl$_3$) δ 8.62 (1H, d, J=4.8 Hz); 8.15 (1H, d, J=8.2 Hz); 7.81 (1H, t, J=7.5 Hz); 7.47 (1H, t, J=7.5 Hz); 7.42-7.27 (6H, m); 7.24 (partly under CHCl$_3$, m); 7.10 (1H, d, J=8.2 Hz); 6.73 (1H, d, J=8.2 Hz); 5.49 (1H, d, J=8.2 Hz); 5.20-5.10 (3H, m); 4.46 (1H, d, J=17.7 Hz); 3.67 (2H, s); 1.24 (2H, s); 1.19 (3H, s); 0.90 (9H, s); 0.08 (3H, s); 0.05 (3H, s) ppm.

3-Amino-1-(4-hydroxy-3,3-dimethyl-2-oxo-butyl)-2,3-dihydro-5-(2-pyridyl)-1H-1,4-benzodiazepin-2-one (12)

Compound 11 (19.0 g, 30.90 mmol) was dissolved in dry dichloromethane and cooled to −10° C. under a nitrogen atmosphere. The solution was slowly saturated with hydrogen bromide gas while maintaining the temperature between −10° C. and 0° C. The mixture rapidly oils out and sticks to the sides of the flask. The mixture was then stirred at 0° C. for 2 h. TLC (elute 10% methanol in dichloromethane) indicated that compound 11 ($R_f$=0.9) had been consumed and a new component ($R_f$=0.40) had formed. Water was added to the mixture and stirred for 5 min before allowing the layers to separate. The aqueous layer was removed and basified to pH=8 with saturated sodium bicarbonate solution. The solution was saturated with sodium chloride and then extracted with chloroform (3×750 mL). The combined chloroform extracts were dried over anhydrous sodium sulphate and stripped to an oil. Under high vacuum the oil formed a glass-like foam solid (11.6 g).

$^1$H NMR (400 MHz, CDCl$_3$) δ 8.62 (1H, d, J=4.1 Hz); 8.14 (1H, d, J=8.2 Hz); 7.72 (1H, t, J=7.5 Hz); 7.54 (1H, t, J=7.8 Hz); 7.37 (2H, m); 7.3-7.15 (partly under CHCl$_3$, m); 5.03 (1H, d, J=17.7 Hz); 4.71 (1H, s); 4.45 (1H, d, J=17.7 Hz); 3.64 (2H, q, J=12 Hz); 2.85 (3H, br s); 1.24 (3H, s); 1.23 (3H, s) ppm.

$^{13}$C NMR (100 MHz, CDCl$_3$) δ 209.1 (q), 169.7 (q), 155.6 (q), 148.9 (CH), 142.3 (q), 136.8 (CH), 132.1 (CH), 130.5 (CH), 128.7 (q), 124.7 (CH×2), 124.3 (CH), 122.0 (CH), 70.6 (CH$_2$), 70.2 (CH), 56.0 (CH$_2$), 49.5 (q), 21.0 (CH$_3$), 20.7 (CH$_3$) ppm.

Mass spectrum by positive ion electrospray M+H=367.1764 m/z (theory: 367.1765 m/z for composition C$_{20}$H$_{23}$N$_4$O$_3$)

1-[1-(4-Hydroxy-3,3-dimethyl-2-oxo-butyl)-2-oxo-5-pyridin-2-yl-2,3-dihydro-1H-1,4-benzodiazepin-3-yl]-3-(3-methylamino-phenyl)-urea (TR1)

A solution of compound 12 (3.41 g, 9.31 mmol) in dichloromethane (28 mL) was cooled to −10° C. under a nitrogen atmosphere. A solution of compound 7 (1.74 g, 7.01 mmol, only 0.75 molar equivalents due to the low purity of compound 12) in dichloromethane (10 mL) was slowly added while maintaining the temperature between −5 and −10° C., and the mixture stirred for 20 min. The mixture was warmed to 0° C. and stirred for a further 20 min before further warming to 20° C. and stirring for a final 30 min. TLC (elute 10% methanol in dichloromethane) indicated that compound 12 ($R_f$=0.40) and compound 7 ($R_f$=0.8) had been consumed and compound 13 ($R_f$=0.55) had formed. Other smaller TLC components could be seen at $R_f$=0.60 and 0.90. The mixture was stripped of solvent under reduced pressure at 25° C. and then re-dissolved in ethyl acetate (35 mL). The mixture was cooled to 0° C. and water (20 mL) followed by hydrochloric acid (32%; 17 mL) slowly added while maintaining the temperature below 5° C. The mixture was slowly warmed to 20° C. and stirred at this temperature for 3 h. TLC (elute 10% methanol in dichloromethane) indicated that compound 18 ($R_f$=0.55) had been consumed and compound 19 ($R_f$=0.50) had formed. Other smaller TLC components could be seen at $R_f$=0.60 and 0.90. The ethyl acetate layer was removed and the aqueous layer washed with more ethyl acetate (20 mL). Dichloromethane (100 mL) was added to the aqueous layer and the pH was adjusted to 10 with 20% sodium hydroxide solution while maintaining the temperature at 0-5° C. The dichloromethane layer was washed with brine (30 mL) and dried over anhydrous sodium sulphate before removing solvent under vacuum to give a foamy glass like solid (4.90 g). The crude product was purified by flash chromatography through silica gel (100 g) eluted with 2% methanol in dichloromethane until the TLC $R_f$=0.6 component was removed and then with 5% methanol in dichloromethane. Good fractions were combined and stripped to a yellow foam/solid (3.56 g). The solid was dissolved in hot isopropanol (20 mL) and allowed to crystallise slowly as it cooled to room temperature. The mixture was filtered and washed with a small amount of cold isopropanol. The product was vacuum dried at 35° C./0.1 mmHg for 3 days in a drying pistol to give white solid 1.68 g. The solid was blended with the product from a smaller trial reaction to give 2.03 g of white powder.

$^1$H NMR (400 MHz, CD$_3$CN) δ 8.57 (1H, dd, J=4.4 and 2.4 Hz); 8.08 (1H, d, J=8.2 Hz); 7.89 (1H, dt, J=7.4 and 2.0 Hz); 7.59 (1H, dt, J=8.2 and 1.4 Hz); 7.47-7.42 (3H, m);

7.32-7.25 (2H, m); 7.00 (1H, t, J=8.2 Hz); 6.79 (1H, t, J=2.0 Hz); 6.67 (1H, d, J=7.5 Hz); 6.57 (1H, dd, J=8.2 and 2.0 Hz); 6.24 (1H, dd, J=8.2 and 2.0 Hz); 5.45 (1H, d, J=8.2 Hz); 4.87, 4.97 (2H, AB system, $J_{AB}$=18.1 Hz); 4.34 (1H, br s); 3.57 (2H, d, J=6.1 Hz); 3.18 (1H, t, J=5.8 Hz); 2.70 (3H, s); 1.14 (3H, s); 1.13 (3H, s) ppm.

Exact mass by positive ion electrospray mass spectroscopy M+H=515.2418 m/z (theory: 515.2407 m/z for composition $C_{28}H_{30}N_6O_4$).

Separation of Racemic Mixture (TR1) by Chiral HPLC Chromatography to Give the Pure Enantiomers (TR2) and (TR3)

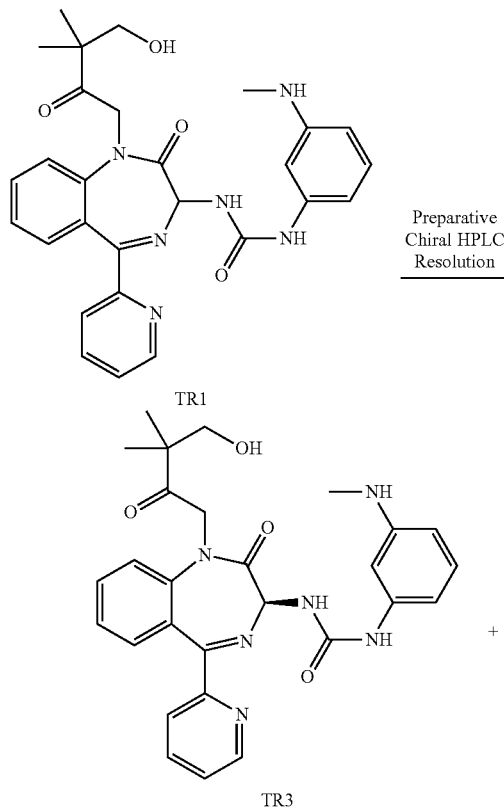

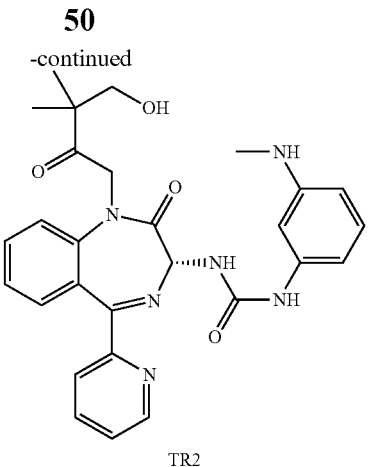

Column: Chiralcel OD 250 mm×20 mm, 5 μm
Mode: super critical fluid (SFC)
Eluent: Methanol 40%, no modifier
Flow: 50 mL/min
Run time: 4 min
Retention time for TR2: 2.2 min
Retention time for TR3: 2.8 min The absolute configuration of (TR2) and (TR3) (shown above) was determined by visual circular dichroism (VCD) with a confidence level of 100%.

X-ray powder diffraction (XRPD) of (TR2) confirmed that the compound is amorphous.

Example 2

Chiral Synthesis of TR2 and TR2-A (TR2) and (TR2-A) were synthesised according to Scheme 5 below. It will be appreciated that this scheme can be applied generally to the synthesis of compounds of the invention as described herein by variation of the starting materials 7 and 10, as appropriate. Compounds 7 and 10 were synthesized as described in Example 1.

Scheme 5

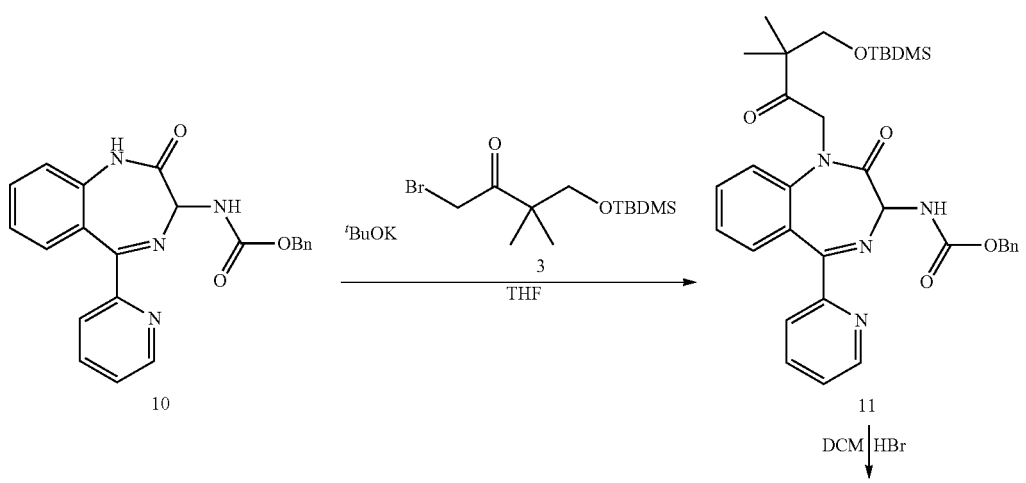

-continued
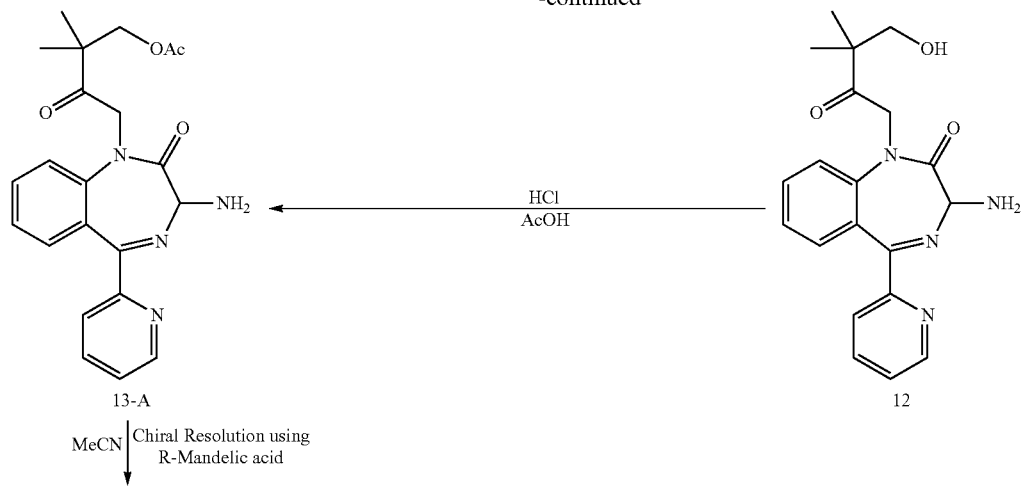
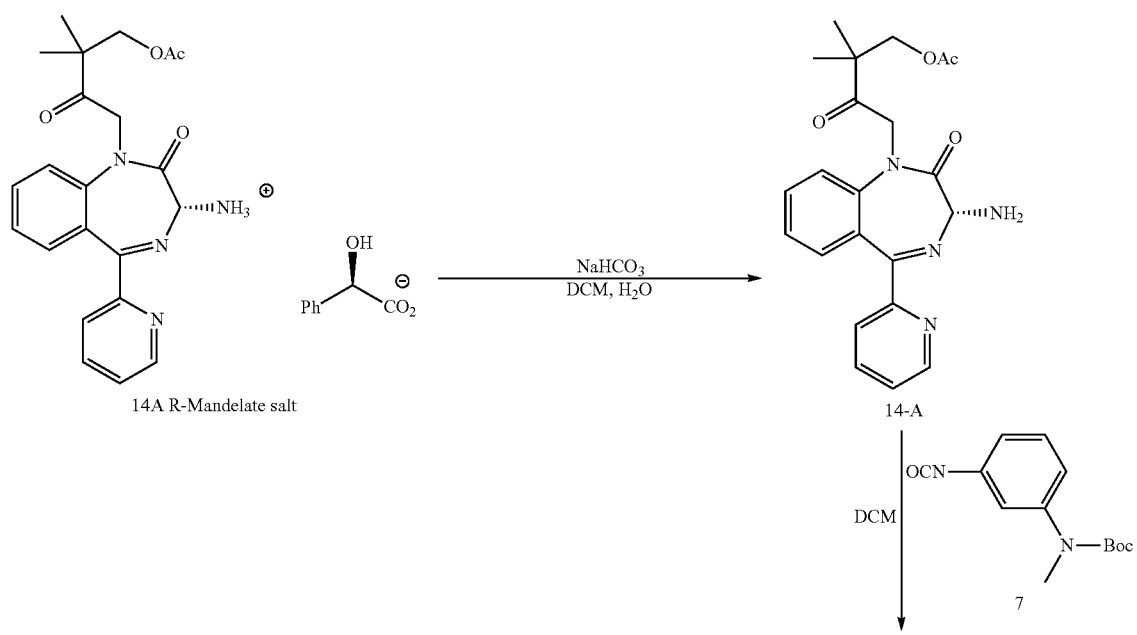
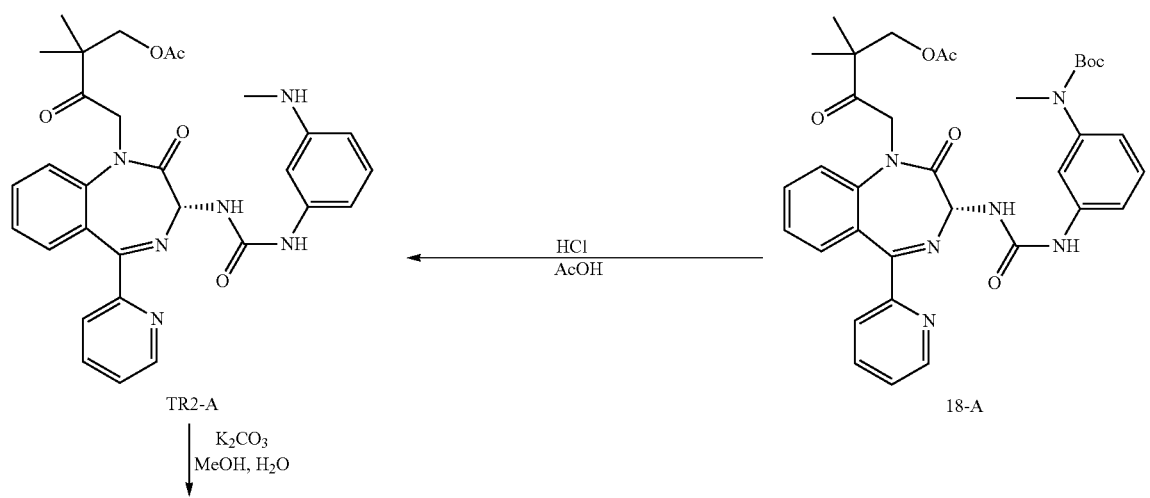

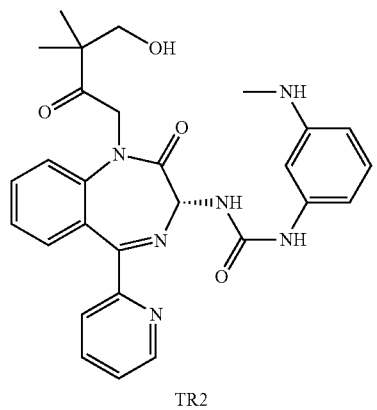

TR2

Benzyl (1-[4-(tert-Butyl-dimethyl-silanyloxy)-3,3-dimethyl-2-oxo-butyl]-2-oxo-5-pyridin-2-yl-2,3-dihydro-1H-benzo[e][1,4]diazepin-3-yl)-carbamate (11)

Compound 10 (300 g, 776 mmol) was slurried in tetrahydrofuran (3.0 L) under a nitrogen atmosphere at 0-5° C. Potassium tert-butoxide (113.3 g) was added in small portions while maintaining the temperature at 0-5° C. A clear solution formed briefly before another solid formed. The mixture was warmed to about 20° C. for one hour and then re-cooled to 0-5° C. Compound 3 (600.4 g, 1.94 mol) was slowly added while maintaining the temperature at 0-5° C. The mixture was warmed to about 20° C. and stirred for a further two hours. TLC (elute 50% ethyl acetate in hexane) indicated that some compound 10 remained. The mixture was warmed to 30° C. and stirred for a further hour. TLC indicated that the reaction was complete. The mixture was poured into water (8 L) and extracted with ethyl acetate (8 L and then 3 L). The combined organic extracts were washed with 5% brine (5 L) and then dried over anhydrous sodium sulfate. The solution was evaporated to give a viscous orange oil (895 g). The oil was slowly poured into stirred hexane (3 L). The resulting mixture was stirred for 2 hours to form a fine slurry. The mixture was filtered and washed with hexane (2×1 L). The product was air dried at about 25° C. overnight to give a tan solid (448 g, 94% yield).

$^1$H NMR (400 MHz, CDCl$_3$) δ 8.63 (1H, d, J=4.8 Hz), 8.15 (1H, d, J=8.2 Hz), 7.81 (1H, t, J=7.5 Hz), 7.47 (1H, t, J=7.5 Hz), 7.42-7.28 (6H, m), 7.23 (1H, t, J=7.5 Hz), 7.10 (1H, d, J=8.2 Hz), 6.73 (1H, d, J=8.2 Hz), 5.49 (1H, d, J=8.2 Hz), 5.20-5.10 (3H, m), 4.45 (1H, d, J=17.7 Hz), 3.67 (2H, s), 1.24 (3H, s), 1.19 (3H, s), 0.90 (9H, s), 0.08 (3H, s), 0.05 (3H, s).

3-Amino-1-(3,3-dimethyl-2-oxo-butyl)-5-pyridin-2-yl-1,3-dihydrobenzo[e][1,4]diazepin-2-one (12)

Compound 11 (448 g, 729 mmol) was dissolved in dichloromethane (15 L) and cooled to −10 to −5° C. under a nitrogen atmosphere. Hydrogen bromide gas was bubbled through the mixture until it was saturated. The solution clouded then an oil formed. The mixture was stirred at 0° C. for 2 hours. TLC (elute 10% methanol in dichloromethane) indicated that the reaction was complete. Water (4 L) was added and the mixture stirred for five minutes. The dichloromethane layer was removed and the aqueous layer washed with more dichloromethane (500 mL). The aqueous layer was adjusted to pH=8 with solid sodium bicarbonate and then saturated with sodium chloride before extracting with dichloromethane (3×2 L). The combined dichloromethane layers were dried over anhydrous sodium sulfate and then partially evaporated under vacuum to give a thick slurry. The slurry was filtered and washed with diethyl ether (300 mL). Air dried at room temperature to give white solid (220 g, 82% yield). HPLC purity 97.7%.

3-Amino-1-(4-acetoxy-3,3-dimethyl-2-oxo-butyl)-5-pyridin-2-yl-1,3-dihydro-benzo[e][1,4]diazepin-2-one (13-A)

Compound 12 (50 g, 136.5 mmol) was dissolved in a saturated (about 1.5 molar) solution of hydrogen chloride in acetic acid (500 mL) and stirred at about 20° C. for 2 hours. TLC (elute 10% methanol in dichloromethane) indicated that the reaction was complete. The solution was evaporated under vacuum to give an amber oil. The oil was dissolved in water (500 mL) and adjusted to pH=8 with solid sodium bicarbonate. The mixture was extracted with dichloromethane (2×300 mL). The combined dichloromethane layers were washed with water and then dried over anhydrous sodium sulfate. The solution was evaporated under vacuum to give an amber foamed-up glass (57 g). The glass was dissolved in hot ethyl acetate (250 mL). Crystallisation occurred during cooling. The mixture was filtered and the filter cake washed with a little ice cold ethyl acetate (50 mL). The product was vacuum dried at 30° C. to give an off white solid (48.7 g, 87% yield).

(R)-3-Amino-1-(4-acetoxy-3,3-dimethyl-2-oxo-butyl)-5-pyridin-2-yl-1,3-dihydro-benzo[e][1,4]diazepin-2-one (R)-mandelate salt (14-A R-mandelate salt)

Compound 13-A (28 g, 68.7 mmol) was slurried in acetonitrile (178 mL) at 20° C. Rmandelic acid (6.27 g, 41.1 mmol) was added and the mixture stirred until a clear solution formed. Diethyl ether (59 mL) was added before slowly cooling the mixture down to −5° C. The mixture was filtered and washed with ice cold 30% diethyl ether in acetonitrile (40 mL). The product was vacuum dried at 40° C. to give a near white solid (20.3 g, 43% ee R-isomer by chiral HPLC). The crude product was dissolved in acetonitrile (89 mL) at about 45° C. and allowed to slowly cool to 20° C. while standing over a 2 hour period. Fibre-like crystals slowly formed. The mixture was filtered and washed with cold (−18° C.) acetonitrile (20 mL) followed by diethyl ether (40 mL). The product vacuum dried at 35° C. to give a white solid (8.2 g, 21% yield, 98.8% ee R-isomer by chiral HPLC).

(R)-3-Amino-1-(4-acetoxy-3,3-dimethyl-2-oxo-butyl)-5-pyridin-2-yl-1,3-dihydro-benzo[e][1,4]diazepin-2-one (14A)

Compound 14-A R-mandelate salt (8.2 g, 14.63 mmol) was dissolved in dichloromethane (100 mL) and washed with saturated sodium bicarbonate solution (2×75 mL). The organic layer was dried over anhydrous sodium sulfate and evaporated under vacuum to give a foamed-up glass (5.3 g, 89% yield).

(R)-1-[1-(4-Acetoxy-3,3-dimethyl-2-oxo-butyl)-2-oxo-5-pyridin-2-yl-2,3-dihydro-1H-benzo[e][1,4]diazepin-3-yl]-3-(3-tert- butoxycarbonyl-methyl-amino-phenyl)-urea (18A)

Compound 14-A (6.83 g, 16.72 mmol) was dissolved in dichloromethane (50 mL) and cooled to −5 to −10° C. under a nitrogen atmosphere. Compound 7 (5.46 g crude, 22.0 mmol) in dichloromethane (10 mL) was slowly added over a 20-minute period while maintaining the temperature at −5 to −10° C. The mixture was warmed to 0° C. and stirred for 20 minutes before further warming to 20° C. for another 30 minutes. TLC (elute 10% methanol in dichloromethane) indicated that only a small amount of 14-A remained. The mixture was evaporated under vacuum at 30° C. to give a glass like foam. The crude product was purified by chromatography through silica gel (250 g) eluting 1% rising to 3% methanol in dichloromethane. Good product fraction were evaporated under vacuum to give a foamed-up glass (6.42 g, 58% yield, 96.8% HPLC purity, 98.9% ee R-isomer chiral HPLC purity).
$^1$H NMR (400 MHz, CDCl$_3$) δ 8.60 (1H, d, J=4.1 Hz), 8.15 (1H, d, J=7.5 Hz), 7.79 (1H, dt, J=8.0, 2.0 Hz), 7.51 (1H, dt, J=8.0, 1.3 Hz), 7.41-7.32 (3H, m), 7.26 (t, part under CHCl$_3$ peak), 7.18 (1H, t, J=7.5 Hz), 7.11 (1H, d, J=8.2 Hz), 7.06 (1H, d, J=8.2 Hz), 6.93 (1H, d, J=8.2 Hz), 6.81-6.75 (1H, m), 5.70 (1H, d, J=7.5 Hz), 5.02 (1H, d, J=18.0 Hz), 4.52 (1H, d, J=18.0 Hz), 4.16 (2H, q, J=8.0 Hz), 3.21 (3H, s), 2.06 (3H, s), 1.45 (9H, s), 1.29 (3H, s), 1.25 (3H, s) ppm.

(R)-1-[1-(4-Acetoxy-3,3-dimethyl-2-oxo-butyl)-2-oxo-5-pyridin-2-yl-2,3-dihydro-1H-benzo[e][1,4]diazepin-3-yl]-3-(3-methylamino- phenyl)-urea (TR2-A)

Compound 18-A (5.18 g, 7.89 mmol) was dissolved in a saturated (about 1.5 molar) solution of hydrogen chloride in acetic acid (50 mL) and stirred at about 20° C. for 3 hours. TLC (elute 10% methanol in dichloromethane) indicated that the reaction was complete. The solution was evaporated under vacuum to remove most of the acetic acid. The oil was dissolved in water (50 mL) and adjusted to pH=8 with solid sodium bicarbonate. The mixture was extracted with dichloromethane (2×50 mL). The combined dichloromethane layers were washed with water and then dried over anhydrous sodium sulfate. The solution was evaporated under vacuum to give an amber foamed-up glass (3.79 g, 86% crude yield). Part of crude product (1.78 g) was purified by chromatography through silica gel (100 g) eluting 1% rising to 3% methanol in dichloromethane. Good product fractions were evaporated under vacuum to give a foamed-up glass (1.39 g, 78% recovery). 96.2% HPLC purity, 98.3% ee R-isomer chiral HPLC purity. Exact mass by positive ion electrospray mass spectroscopy.

M+H=557.2510 m/z (theory 557.2512 for composition C$_{30}$H$_{32}$O$_6$N$_5$).
$^1$H NMR (400 MHz, CDCl$_3$) δ 8.60 (1H, d, J=4.8 Hz), 8.15 (1H, d, J=8.2 Hz), 7.78 (1H, dt, J=8.0, 2.0 Hz), 7.50 (1H, dt, J=8.0, 2.0 Hz), 7.40-7.31 (2H, m), 7.25 (t, part under CHCl$_3$ peak), 7.10 (1H, d, J=7.5 Hz), 7.03 (1H, t, J=8.2 Hz), 6.91 (1H, d, J=8.2 Hz), 6.84 (1H, s), 6.76 (1H, t, J=2.0 Hz), 6.53 (1H, dd, J=8.2, 2.0 Hz), 6.29 (1H, dd, J=8.2, 2.0 Hz), 5.72 (1H, d, J=8.2 Hz), 4.98 (1H, d, J=17.7 Hz), 4.50 (1H, d, J=17.7 Hz), 4.14 (2H, q, J=8.0 Hz), 3.75 (1H, br s), 2.78 (3H, s), 2.05 (3H, s), 1.28 (3H, s), 1.24 (3H, s) ppm.

(R)-1-[1-(4-Hydroxy-3,3-dimethyl-2-oxo-butyl)-2-oxo-5-pyridin-2-yl-2,3-dihydro-1H-benzo[e][1,4] diazepin-3-yl]-3-(3-methylamino- phenyl)-urea (TR2)

A solution of TR2-A (2.01 g, 3.61 mmol) in methanol (26 mL) was added to a solution of potassium carbonate (1.0 g, 7.23 mmol) in water (12 mL) and stirred at 20° C. for 2 hours. TLC (elute 10% methanol in dichloromethane) indicated that the hydrolysis was complete. Most of the methanol was evaporated under reduced pressure. The residue was diluted with more water (20 mL) and then extracted into dichloromethane (2×40 mL). The combined extracts were evaporated to give a glass like foam (1.82 g). The crude product was purified by chromatography through silica gel (100 g) eluting 1% rising to 3% methanol in dichloromethane. Good product fractions were evaporated under vacuum to give a pale yellow foamed-up glass (1.45 g, 78% yield). 97.1% HPLC purity, 95.0% ee R-isomer chiral HPLC purity). Exact mass by positive ion electrospray mass spectroscopy
M+H=515.2398 m/z (theory 515.2407 for composition C$_{28}$H$_{30}$O$_6$N$_4$).
$^1$H NMR (400 MHz, CDCl$_3$) δ 8.60 (1H, d, J=4.8 Hz), 8.12 (1H, d, J=7.5 Hz), 7.78 (1H, dt, J=7.5, 2.0 Hz), 7.52 (1H, dt, J=7.5, 1.4 Hz), 7.39-7.32 (2H, m), 7.26 (t, part under CHCl$_3$ peak), 7.20 (1H, d, J=8.2 Hz), 7.04 (1H, t, J=8.0 Hz), 6.94-6.85 (2H, m), 6.76 (1H, t, J=1.4 Hz), 6.55 (1H, dd, J=8.2, 2.0 Hz), 6.30 (1H, dd, J=8.2, 2.0 Hz), 5.70 (1H, d, J=8.2 Hz), 4.90 (1H, d, J=17.7 Hz), 4.49 (1H, d, J=17.7 Hz), 3.58 (2H, q, J=8.2 Hz), 3.16 (1H, br s), 2.78 (3H, s), 1.21 (3H, s), 1.20 (3H, s) ppm.

Example 3

Alternative Synthesis of (TR2-A) Via Tert-Butyl (3-aminophenyl)methylaminocarbamate (N4)

(TR2) and (TR2-A) may be synthesised according to the Scheme 6 below.

Scheme 6

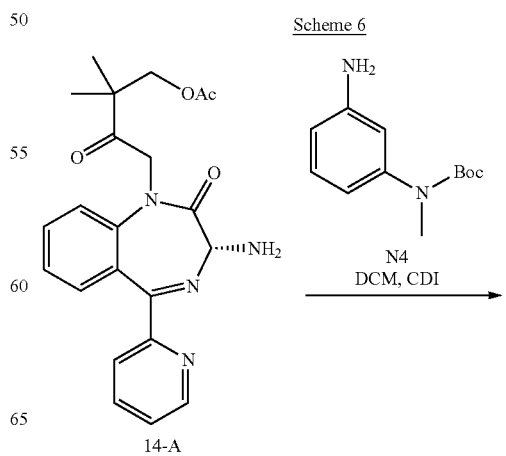

14-A

57
-continued
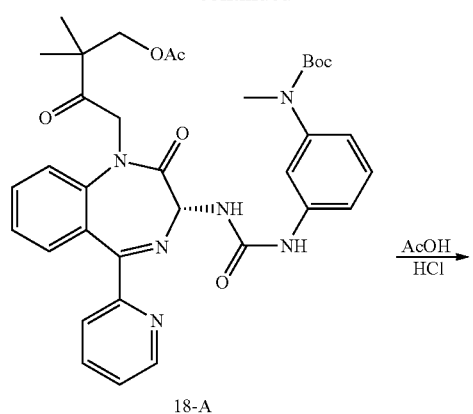
18-A
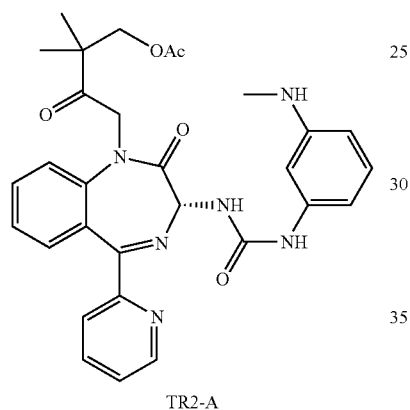
TR2-A
K₂CO₃ | MeOH, H₂O
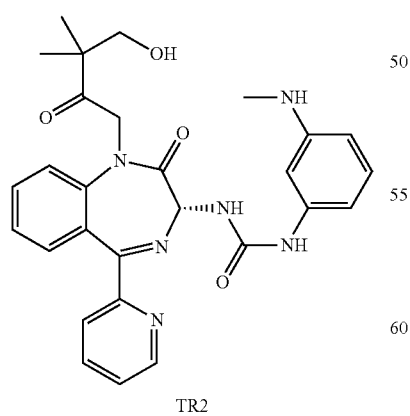
TR2
Compound 14-A was synthesised according to Scheme 7 below:
58
Scheme 7
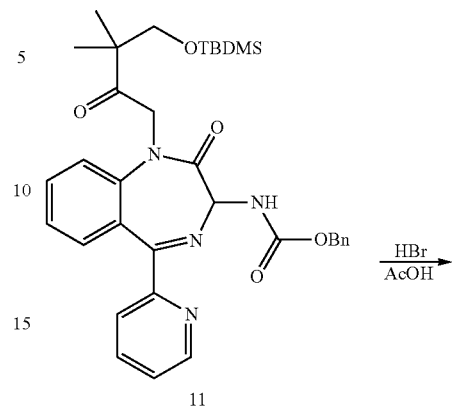
11
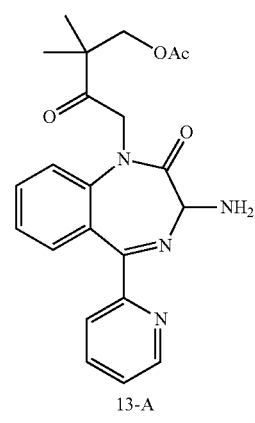
13-A
Chiral resolution using R-Mandelic acid | MeCN
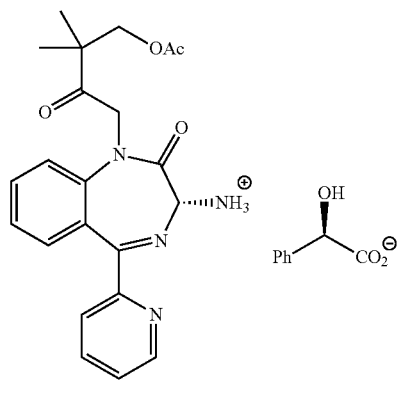
14-A-R-Mandelate salt
DCM, H₂O | NaHCO₃

-continued
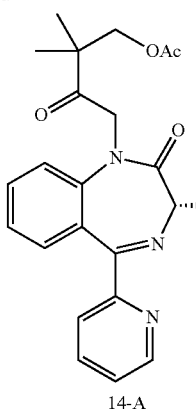
14-A
Compound 11 was synthesised according to Scheme 8 below:
Scheme 8
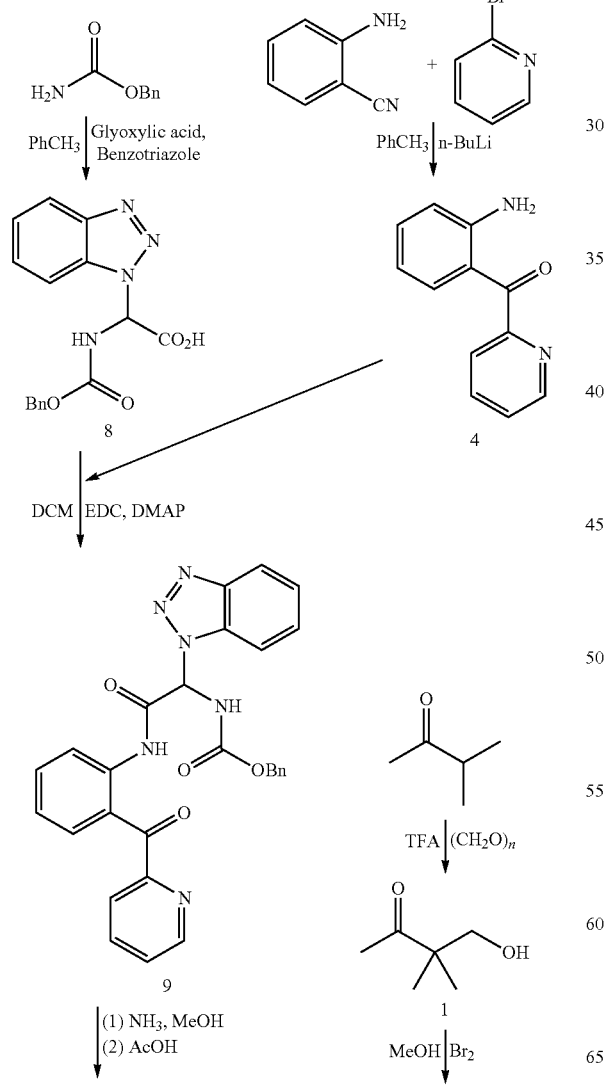
-continued
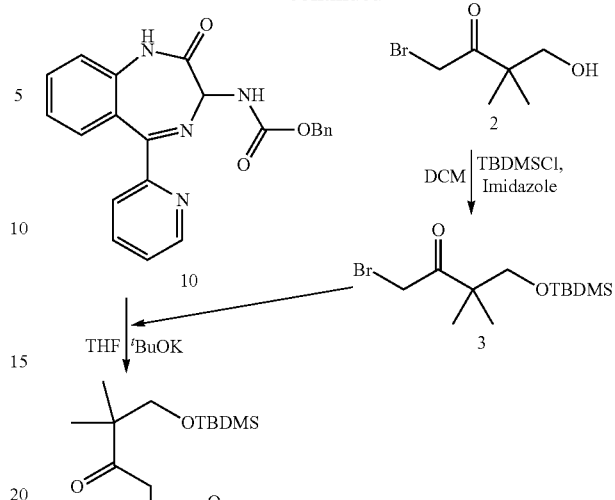
Compound N4 was synthesised according to Scheme 9 below:
Scheme 9
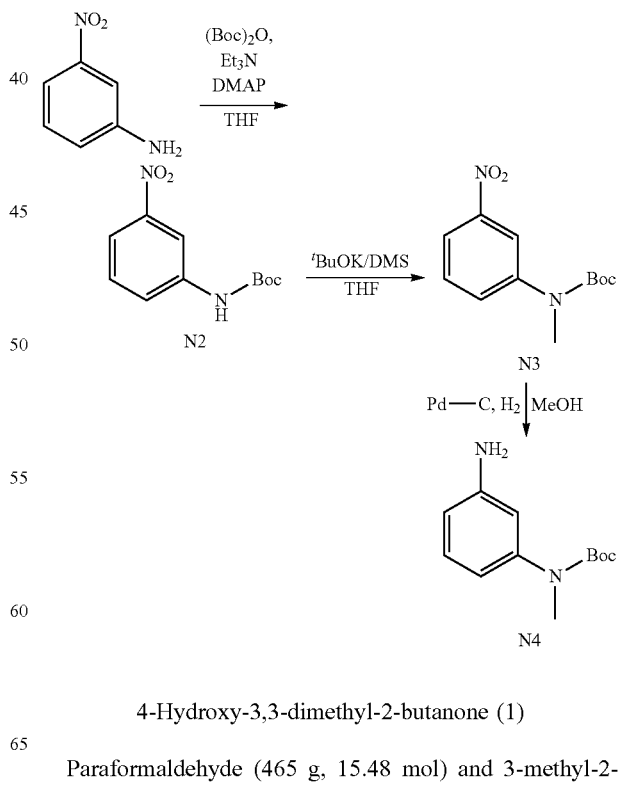
4-Hydroxy-3,3-dimethyl-2-butanone (1)
Paraformaldehyde (465 g, 15.48 mol) and 3-methyl-2-butanone (1111 g, 12.90 mol) were added to trifluoroacetic acid (6.0 L) and the mixture slowly warmed to 90° C. in an oil bath over a one hour period. All the paraformaldehyde dissolved at about 50° C. The oil bath was cooled to 75° C. (cardice addition to the oil). Once the flask content temperature reduced to 85° C. a further charge of paraformaldehyde (465 g, 15.48 mol) and 3-methyl-2-butanone (1111 g, 12.90 mol) was added. The mixture slowly exothermed to about 92° C. (the oil bath was still at 75° C.). Once the flask content temperature had reduced to 85° C. the final charge of paraformaldehyde (465 g, 15.48 mol) and 3-methyl-2-butanone (1111 g, 12.90 mol) was added. After the exotherm was over, the mixture was stirred at 90° C. for a further 8 hours before cooling back to room temperature overnight. GC (of a small sample added to water and adjusted to pH=14 with sodium hydroxide then extracted into DCM) indicated about 2% 3-methyl-2-butanone and 86% product. The product solution was poured into a stirred mixture of ice (16 kg; extra cold from freezer) and solid sodium hydroxide (3 kg). A further charge of sodium hydroxide (about 260 g) was added to just bring the pH to 14. GC indicated hydrolysis was complete. The aqueous solution was saturated with sodium chloride (about 3 kg added) then without delay extracted with DCM (3×8 L). The combined DCM layers were washed with saturated brine (3 L) and dried over anhydrous sodium sulfate. The solution was evaporated under vacuum to give a light brown liquid (about 3.7 kg). The crude product was distilled through a 20 cm Vigreux distillation column at about 95° C./45 mmHg (A fore cut was removed and some residue remained after distillation) to give a near colourless product (2.85 kg, 63% yield, GC purity=98%).

1-Bromo-4-hydroxy-3,3-dimethyl-2-butanone (2)

Compound 1 (2566 g, 22.09 mol) was dissolved in methanol (13 L) and stirred at 20° C. The reaction flask was covered to protect it from light. Bromine (200 g, 1.25 mol) was added over 15 minutes. After a short induction period the reaction decolourised and a slight exotherm occurred. Once the mixture had decolourised it was cooled to 0° to 5° C. Bromine (3300 g, 20.65 mol) was slowly added over a two hour period while maintaining the temperature at 0°-5° C. (decolourisation was now fast). GC indicated about 94% product and <1% starting material. Several small after-peaks could also be seen by GC. Without delay the mixture was poured into saturated brine solution (20 L) and ice (4 kg) then extracted with DCM (4×8 L). The combined DCM extracts were washed with saturated brine (2×5 L) and then dried over anhydrous sodium sulfate. The solution was evaporated under vacuum at 40° C. to give a light yellow/brown liquid (4191 g, 97% yield, GC purity 91%).

1-Bromo-4-(tert-butyl-dimethyl-silanyloxy)-3,3-dimethyl-2-butanone (3)

Imidazole (645 g, 9.47 mol) was added to DCM (8.5 L) and cooled to −15° C. to −20° C. under a nitrogen atmosphere. Compound 2 (1650 g, 8.46 mol) was added to give a clear solution at −15° C. to −20° C. tert-Butyl-dimethylsilyl chloride (1365 g, 9.06 mol) was slowly added while maintaining the temperature at −15° C. to −20° C. The mixture was stirred for a further 3 hours at that temperature. GC indicated 78% product, less than 1% starter and 14% residual tert-butyl-dimethylsilyl chloride. The reaction mixture was poured into cold water (7.5 L). The aqueous layer was removed and re-extracted with more DCM (2 L). The combined DCM layers were washed with water (2×2 L) then with saturated brine (2×3 L) before drying over anhydrous sodium sulfate. The solution was evaporated under vacuum at 40° C. to give a yellow oil (2559 g, 97% yield, GC purity about 75%).

$^1$H NMR (400 MHz, CDCl$_3$) δ 4.24 (s, 2H); 3.55 (s, 2H); 1.17 (s, 6H); 0.86 (s, 9H); 0.02 (s, 6H).

2-(2-Aminobenzoyl)pyridine (4)

2-bromopyridine (1075 g, 6.80 mol) in toluene (4.2 L) was cooled to <−65° C. while stirring under a nitrogen atmosphere. n-Butyl lithium (1.6 M in hexane; 4160 mL, 6.66 mol) was added over a one hour period while maintaining the temperature <−60° C. The mixture was stirred at <−60° C. for 30 minutes before checking for the absence of 2-bromopyridine by GC. A solution of 2-aminobenzonitrile (350 g, 2.96 mol) in toluene (2.3 L) (may need warming slightly to dissolve) was slowly added over a 30-minute period while maintaining the temperature at <−60° C. The mixture was allowed to warm slowly to room temperature while stirring overnight. The mixture was carefully poured into cold hydrochloric acid solution (1.96 L 32% hydrochloric acid, 3 L water and 2 kg ice) while stirring. The mixture was stirred for a further hour before allowing the layers to separate. The lower aqueous layer was removed and the upper organic layer was extracted with hydrochloric acid solution (350 mL of 32% hydrochloric acid and 3 L of water). Ice (4 kg) was added to the combined acidic aqueous layers before adjusting to pH=10 with 35% ammonia solution (about 6.5 L). Add more ice as required to achieve a final temperature of 0-5° C. The slurry was stirred at 0-5° C. for a further 30 minutes. The slurry was filtered and washed with water until free of ammonia. The product was dried in a circulated air oven at 50° C. (until a constant weight was achieved) to give a yellow/orange solid (558 g, 95% yield, 87% GC purity).

2-(Benzotriazol-1-yl)-2-(benzyloxycarbonylamino)-acetic acid (8)

A vigorously stirred mixture of benzotriazole (512 g, 4.30 mol), benzyl carbamate (650 g, 4.30 mol) and glyoxylic acid monohydrate (396 g, 4.30 mol) in toluene (12 L) was heated to reflux and water removed using a Dean and Stark apparatus. Heating rate was adjusted to keep foaming down. Water evolution ceased after about 150 mL had been collected. A solid also formed in the stirred mixture. The mixture was heated at reflux for a further hour before slowly allowing to cool overnight. The solid was filtered off and pulled down hard for 30 minutes before washing with MTBE (2×1 L). The product was air dried at 40° C. (until constant weight was achieved) to give a near white solid (1330 g, 95% yield, single spot by TLC).

Benzyl-(benzotriazol-1-yl-[2-(pyridine-2-carbonyl)-phenylcarbamoyl]-methyl)-carbamate (9)

A mixture of crude compound 4 (2000 g, 10.09 mol) and compound 8 (3620 g, 11.09 mol) in DCM (36 L) was cooled to 0-5° C. in a 60 L reaction vessel. 4-Dimethylaminopyridine (148 g, 1.21 mol) was added in one lot. 1-(3-Dimethylaminopropyl)-3-ethylcarbodiimide hydrochloride (2417 g, 12.61 mol) was added in small portions over a 30-minute period while maintaining the temperature at 0-5° C. The mixture was stirred for a further hour at 0-5° C. to give a clear dark brown solution. TLC (elute 50% ethyl acetate in hexane) indicated that all compound 4 (Rf=0.7 yellow spot)

had been consumed and compound 9 (Rf=0.35) had formed. Saturated sodium bicarbonate solution (20 L) was added and the mixture stirred for 5 minutes. The aqueous layer was removed and the organic layer dried over anhydrous sodium sulfate before evaporating under vacuum to give thick oil (about 7150 g, 140% crude yield).

Benzyl (2-oxo-5-pyridin-2-yl-2,3-dihydro-1H-benzo[e][1,4]diazepin-3-yl)-carbamate (10)

Crude compound 9 (about 7.15 kg) was dissolved in methanol (10 L) and stirred at room temperature. A solution of methanol saturated with ammonia (10 L) was added in one portion. The mixture was stirred for one hour at room temperature. TLC (elute 50% ethyl acetate in hexane) indicated that compound 9 (Rf=0.35) had eliminated benzotriazol (Rf=0.5) to give an un-cyclised intermediate (Rf=0.1). The mixture was initially warmed to about 30° C. and then allowed to stir overnight while cooling to room temperature. A solid formed in the stirred mixture. TLC (elute 50% ethyl acetate in hexane) indicated that the un-cyclised intermediate (Rf=0.1) had cyclised to form compound 10 (Rf=0.15). The slurry was filtered and the filter cake washed with cold methanol (1 L) followed by ethyl acetate (3 L) and finally hexane (2 L). The filtrate was stripped to about half its original volume and allowed to stand for two days. A second crop was filtered off (if formed) and washed with cold methanol, ethyl acetate and hexane. The combined good crops were air dried at 40-50° C. in a circulating air cabinet to give an off white solid (1785 g). The material can be slurried in two volumes of DCM, filtered and re-dried to improve purity if required.

A total of 27.6 kg (92% HPLC purity) of crude compound 10 was made from 114.4 kg of crude compound 9 using the above method. A DCM slurry reduced the yield to 25.9 kg (98% HPLC purity; 42% yield over two steps from compound 4).

1H NMR (400 MHz, CDCl$_3$) δ 8.67 (1H, s), 8.61 (1H, d, J=4.1 Hz), 8.10 (1H, d, J=7.5 Hz), 7.84 (1H, dt J=1.4, 7.5 Hz), 7.50-7.28 (8H, m), 7.20 (1H, t, J=7.5 Hz), 6.99 (1H, d, J=7.5 Hz), 6.65 (1H, d, J=8.2 Hz), 5.37 (1H, d, J=8.2 Hz), 5.15 (2H, d, J=2.7 Hz).

Benzyl (1-[4-(tert-Butyl-dimethyl-silanyloxy)-3,3-dimethyl-2-oxo-butyl]-2-oxo-5-pyridin-2-yl-2,3-dihydro-1H-benzo[e][1,4]diazepin-3-yl)-carbamate (11)

Compound 10 (1040 g, 2.69 moles) was slurried in tetrahydrofuran (10.4 L) under a nitrogen atmosphere at 0-5° C. Potassium tert-Butoxide (423 g, 3.77 mol) was added in a single portion resulting in a 10° C. exotherm. A near clear solution formed briefly before another solid formed. The mixture was re-cooled to 0-5° C. Crude compound 3 (2080 g, 6.72 mol crude with 5.04 mol active content) was slowly added over a 30-minute period while maintaining the temperature at 0-5° C. Stirred for a further 30 minutes. The mixture was warmed to 20-25° C. and stirred for a further hour. TLC (elute 50% ethyl acetate in hexane) indicated that compound 12 (Rf=0.55) had formed but some compound 10 (Rf=0.15) remained. A silyl by-product spot (Rf=0.8) could also be seen. A further charge of potassium tert-butoxide (78 g, 0.70 mol) was added in one lot and the mixture stirred for 20 minutes. TLC check occasionally indicated that all of compound 10 had been consumed. If some compound 10 remains by TLC add extra crude compound 3 (200 g, 0.65 mol) stir for 10 minutes. Charge extra potassium tert-butoxide (78 g, 0.70 mol) and stir for 20 minutes. The reaction should now be complete but this step can be repeated until compound 10 is consumed. The mixture was stirred for a further hour and then allowed to stand overnight at room temperature. The reaction mixture was poured into 5% brine solution (20 L) and extracted with ethyl acetate (10 L and then 5 L). The combined organic extracts were washed with 5% brine solution (5 L) and then dried over anhydrous sodium sulfate. The solution was evaporated under vacuum to give viscous oil (sometimes containing some crystals). The oil was slowly poured into hexane (15 L) allowing time a solid to form. The resulting slurry was stirred for 2 hours to form a fine slurry. The mixture was filtered and washed with hexane (2×3 L). The filter cake was air dried at 20-30° C. in a circulating air cabinet to give a tan solid (1291 g, 78% yield, 97.6% HPLC purity).

$^1$H NMR (400 MHz, CDCl$_3$) δ 8.63 (1H, d, J=4.8 Hz), 8.15 (1H, d, J=8.2 Hz), 7.81 (1H, t, J=7.5 Hz), 7.47 (1H, t, J=7.5 Hz), 7.42-7.28 (6H, m), 7.23 (1H, t, J=7.5 Hz), 7.10 (1H, d, J=8.2 Hz), 6.73 (1H, d, J=8.2 Hz), 5.49 (1H, d, J=8.2 Hz), 5.20-5.10 (3H, m), 4.45 (1H, d, J=17.7 Hz), 3.67 (2H, s), 1.24 (3H, s), 1.19 (3H, s), 0.90 (9H, s), 0.08 (3H, s), 0.05 (3H, s).

tert-Butyl (3-nitrophenyl)-carbamate (N2)

Triethylamine (915 g, 9.04 mol) and 4-(dimethylamino)-pyridine (30 g, 0.25 mol) was added to a solution of 3-nitroaniline (833 g, 6.03 mol) in tetrahydrofuran (6.1 L) at room temperature. The mixture was heated to reflux then external heating turned off. A solution of di-tert-butyldicarbonate (1448 g, 6.63 mol) in tetrahydrofuran (2.2 L) was added at such a rate to maintain reflux. The mixture was heated at reflux with external heating for a further 2 hours. TLC (elute 33% ethyl acetate in hexane) indicated that all the 3-nitroaniline (Rf=0.6) had been consumed and compound N2 (Rf=0.85) had formed. The mixture was allowed to cool to room temperature overnight. Solvent was evaporated under vacuum and the residue dissolved in DCM (15 L). The mixture was washed with water (2×8 L) then dried over anhydrous sodium sulfate. The DCM solution was passed through a silica gel plug (1 kg) and washed through with more DCM (5 L) to remove residual 4-(dimethylamino)-pyridine. The solution was evaporated under vacuum to give a thick slurry. Hexane (4 L) was added and the mixture allowed cool overnight. The mixture was filtered and washed with hexane (3 L). The filter cake was dried in a circulating air cabinet overnight to give a tan solid (1205 g, 84% yield, single spot by TLC).

tert-Butyl methyl-(3-nitrophenyl)-carbamate (N3)

A solution of tert-butyl-(3-nitrophenyl)-carbamate (904 g, 3.79 mol) in tetrahydrofuran (11.25 L) was cooled to 0-5° C. under a nitrogen atmosphere. Potassium tert-butoxide (555 g, 4.95 mol) was added in small portions over a one hour period while maintaining the temperature at <10° C. The mixture was then stirred at about 10° C. for 90 minutes before re-cooling back to 0-5° C. Dimethyl sulfate (622 g, 4.93 moles) was slowly added over a one hour period while maintaining the temperature at <10° C. The mixture was allowed to warm to room temperature while stirring overnight. TLC (elute 10% ethyl acetate in hexane) indicated that all N2 (Rf=0.35) had been consumed and N3 (Rf=0.45) had formed. The mixture was carefully poured into dilute ammonia solution (3 L of 33% w/w ammonia solution and 10 L of water) and stirred for one hour. The mixture was extracted into DCM (3×5 L). The combined organic extracts were washed with water (5 L) and then brine (5 L) before drying over anhydrous sodium sulfate. The mixture was evaporated under vacuum to give red/brown oil (943 g, 98% yield, 98.5% GC purity).

$^1$H NMR (400 MHz, CDCl$_3$) δ 8.14 (1H, t, J=2.1 Hz), 7.98 (1H, dd, J=8.1, 2.0 Hz), 7.61 (1H, d, J=8.1 Hz), 7.47 (1H, t, J=8.1 Hz), 3.31 (3H, s), 1.46 (9H, s).

tert-Butyl (3-aminophenyl)-methyl-carbamate (N4)

Triethylamine (30 mL) was added to a solution of tert-butyl methyl-(3-nitrophenyl)-carbamate (500 g, 1.98 mol) in methanol (2.5 L). Palladium on carbon (5% w/w; Johnson Matthey type 87 L paste, 50% water; 50 g) was carefully added under a nitrogen atmosphere and the mixture hydrogenated using a Parr shaker at 50 psi hydrogen pressure. Hydrogen uptake was rapid and the mixture exothermed from 20° C. to 75° C. Hydrogenation was continued for one hour after the exotherm had ended. TLC (elute 89% chloroform, 10% methanol and 1% ammonia solution) indicated that N3 (Rf=0.75) had been consumed and N4 (Rf=0.55) had formed. The mixture was carefully filtered through a bed of celite on top of a GF-F fibre pad. The filtrate was evaporated under vacuum to dryness. The resulting solid residue was slurried in hexane (1000 mL) for one hour. The mixture was filtered and washed with hexane (500 mL). The product was dried in a vacuum oven at 40° C. to give a tan solid (429 g, 97% yield). 98.6% GC purity, melting range=100-102° C. (This hydrogenation has also been carried out at atmospheric pressure).

$^1$H NMR (400 MHz, CDCl$_3$) δ 7.09 (1H, t, J=7.9 Hz), 6.65-6.56 (2H, m), 6.5 (1H, dd, J=8.1, 2.0 Hz), 3.65 (2H, br s), 3.22 (3H, s), 1.45 (9H, s).

3-Amino-1-(4-acetoxy-3,3-dimethyl-2-oxo-butyl)-5-pyridin-2-yl-1,3-dihydrobenzo[e][1,4]diazepin-2-one (13-A)

A 45% w/v solution of hydrogen bromide in acetic acid (2080 mL, 11.6 mol) was diluted with more acetic acid (11 L) and stirred at room temperature. Compound 11 (2230 g, 3.63 mol) was added in one lot (with a 4° C. exotherm). The mixture was warmed to 35-40° C. for 2 hours. TLC (of a small sample neutralised with saturated sodium bicarbonate and extracted into dichloromethane, elute 5% methanol in dichloromethane) indicated that all of compound 11 (Rf=0.95) had been consumed and that only a small trace of Cbz protected intermediate (Rf=0.45) remained. The mixture was evaporated under vacuum (75° C./<100 mbar) to remove most of the acetic acid. The thick residue was dissolved in cold water (20 L) at <10° C. and washed with dichloromethane (2×8 L) to remove benzyl bromide and silyl by-products. Each dichloromethane wash was back extracted with water (3 L). Fresh dichloromethane (10 L) was added to the aqueous solution. Solid sodium bicarbonate was added to the stirred mixture until effervescence stopped and pH=8. The dichloromethane layer was removed and the aqueous layer extracted with more dichloromethane (5 L). The combined dichloromethane layers were dried over anhydrous sodium sulfate and evaporated under vacuum to give a thick oil. Ethyl acetate (5 L) was added to the oil while still in the rotating Rotavap flask. The oil dissolved and a solid crystallised out. The slurry was cooled to room temperature and filtered. The filter cake was washed well with cold ethyl acetate. The mother liquor was evaporated to produce a further crop. The product was dried at 35° C. in a circulating air cabinet to give an off white powder (1250 g, 84% yield, 98.6% HPLC purity).

$^1$H NMR (400 MHz, CDCl$_3$) δ 8.62 (1H, d, J=3.9 Hz), 8.17 (1H, d, 7.8 Hz), 7.81 (1H, dt, J=2.0, 7.8 Hz), 7.49 (1H, dt, J=2.0, 7.8 Hz), 7.42-7.33 (2H, m), 7.23 (1H, dt, J=1.0, 7.8 Hz), 7.09 (1H, d, J=8.3 Hz), 5.10 (1H, d, J=18.0 Hz), 4.67 (1H, s), 4.43 (1H, d, J=18.0 Hz), 4.18 (2H, q, J=10 Hz), 3.65 (2H, br s), 2.47 (1H, br s), 2.08 (3H, s), 1.32 (3H, s), 1.28 (3H, s).

(R)-3-Amino-1-(4-acetoxy-3,3-dimethyl-2-oxo-butyl)-5-pyridin-2-yl-1,3-dihydrobenzo[e][1,4]diazepin-2-one (R)-mandelic acid salt (14-A R-mandelate salt)

Compound 13-A (1266 g, 3.10 mol) was slurried in acetonitrile (8050 mL) at 20° C. About half the solid seemed to dissolve. R-Mandelic acid (283 g, 1.86 mol, 0.6 molar equiv.) was added to the stirred mixture. The remaining solid slowly dissolved to form a clear yellow solution. Diethyl ether (2660 mL) was added. The solution remained clear at 20° C. The mixture was slowly cooled to −5° C. over a 30-minute period. As the temperature dropped below 5° C., the solution may be seeded with previously made R-mandelate salt (>99% ee by chiral HPLC). A very thick suspension forms (almost solidified) that slowly thinned out while stirring for a further 2 hours. The mixture was filtered (slow) and washed with cold (−18° C.) 50% acetonitrile in diethyl ether (1.5 L) and then with just diethyl ether (2.5 L). The product was dried at 35° C. in a circulating air cabinet overnight to give a near-white solid (1022 g slightly damp). The solid can be slightly gummy if any acetonitrile remains during air drying. Chiral HPLC indicated that the salt was composed of about 69% R-isomer and 32% S-isomer. The crude product (1022 g) was dissolved in acetonitrile (4.1 L) at about 45° C. Heated until just in solution and then allow to cool naturally immediately with only occasional mixing. Prolonged heating or overheating seemed to results in product decomposition. Once the temperature had dropped below 35° C. the solution may be seeded with previously made R-mandelate salt. The mixture was slowly cooled to about 20° C. over a 4-hour period with occasional stirring. The thick mixture was filtered and washed with cold (about −10° C.) acetonitrile (1 L) followed by diethyl ether (2 L). The product was dried at 35° C. in a circulating air cabinet overnight to give a white crystalline solid (461 g, 99.5% ee R-isomer by chiral HPLC, 26.5% yield). Seeding with R-mandelate salt made by a procedure corresponding to that above or in Example 2 can be used to expedite crystallisation, but is not essential.

(R)-3-Amino-1-(4-acetoxy-3,3-dimethyl-2-oxo-butyl)-5-pyridin-2-yl-1,3-dihydrobenzo[e][1,4]diazepin-2-one (14-A)

Compound 14-A R-mandelate salt (4474 g, 7.98 mol) was dissolved in a stirred mixture of saturated sodium bicarbonate (25 L) and dichloromethane (25 L) and stirred for 10 minutes. The aqueous layer was removed and back extracted with dichloromethane (5 L). The combined dichloromethane layers were washed with more saturated sodium bicarbonate solution (10 L).

The new aqueous layer was back extracted with dichloromethane (5 L) again. The combined dichloromethane extracts were dried over anhydrous sodium sulfate. The free base solution was evaporated down to a volume of 15 L. This solution was assumed to contain 3260 g (7.98 mol) of compound 14-A. The solution was used directly in the next step. 99.6% HPLC purity, 99.3% ee R-isomer chiral HPLC purity.

$^1$H NMR (400 MHz, CDCl$_3$) δ 8.62 (1H, d, J=4.1 Hz), 8.17 (1H, d, J=7.5 Hz), 7.82 (1H, dt, J=1.3, 8.1 Hz), 7.50 (1H, dt, J=2.0, 7.8 Hz), 7.42-7.33 (2H, m), 7.23 (1H, t, J=6.8 Hz), 7.09 (1H, d, J=8.2 Hz), 5.10 (1H, d, J=18.0 Hz), 4.67 (1H, s), 4.43 (1H, d, J=18.0 Hz), 4.18 (2H, q, J=10 Hz), 2.48 (1H, br s), 2.08 (3H, s), 1.56 (2H, br s), 1.32 (3H, s), 1.28 (3H, s).

(R)-1-[1-(4-Acetoxy-3,3-dimethyl-2-oxo-butyl)-2-oxo-5-pyridin-2-yl-2,3-dihydro-1H-benzo[e][1,4]diazepin-3-yl]-3-(3-tert-butoxycarbonyl-methyl-amino-phenyl)-urea (18-A)

A slurry of 1,1'-carbonyldiimidazole (421 g, 2.60 mol) in DCM (3260 mL) was cooled to 0-5° C. while stirring under a nitrogen atmosphere. A solution of compound N4 (577 g, 2.60 mol) in DCM (1630 mL) was slowly added over a 30-minute period while maintaining the temperature at 0-5° C. The 1,1'-carbonyldiimidazole slowly dissolved to form a light orange solution during the addition. The solution was stirred at 0-5° C. for a further hour before warming to 15-20° C. and stirring for a further hour. A 21.73% w/v solution of compound 14A (3751 mL, containing 815 g, 2.00 mol) in DCM was slowly added over a 30-minute period while maintaining the temperature at 15-20° C. The mixture was stirred at this temperature for a further 2 hours. TLC (Small sample quenched into saturated sodium bicarbonate solution. Elute ethyl acetate) indicated that all of compound 14A (Rf=0.1) had been consumed and compound 18A (Rf=0.35) had formed. The mixture was washed with saturated sodium bicarbonate solution (2×6 L). Each wash was back extracted with DCM (2 L). The combined DCM layers were dried over anhydrous sodium sulfate and evaporated under vacuum to give a thick oil (2020 g, still a little solvent-wet). Ethyl acetate (5 L) was added and evaporation continued to remove residual DCM from the mixture. The mixture was made-up to a volume of 7.25 L with ethyl acetate (a crude concentration of about 25% w/v). 85.8% HPLC purity with two earlier running components (6.9% and 0.8%) and two later running components (3.9% and 0.6%).

Purification of Compound 18-A

A chromatography column was wet packed with 3 kg of silica gel in 79% ethyl acetate, 20% hexane and 1% triethylamine (the triethylamine is used only during column packing). About 1000 mL of compound 18A solution (containing about 250 g of crude product) was diluted to 2000 mL with ethyl acetate and then hexane (500 mL) slowly added while stirring. This clear solution was charged onto the column. The column was eluted with 20% hexane in ethyl acetate (about 35 L required) until the less polar impurity was removed and then with ethyl acetate (about 35 L required) until compound 18A is removed. Good fractions were evaporated under vacuum to remove solvent. Evaporation was stopped while the product oil was still mobile and before a thick tar/glass formed. HPLC purity 96.8%.

$^1$H NMR (400 MHz, CDCl$_3$) δ 8.61 (1H, d, J=4.1 Hz), 8.15 (1H, d, J=7.5 Hz), 7.79 (1H, dt, J=2.0, 7.5 Hz), 7.51 (1H, t, J=7.9 Hz), 7.42-7.30 (3H, m), 7.26 (1H, t, J=7.5 Hz), 7.19 (1H, t, J=8.1 Hz), 7.13-7.05 (2H, m), 6.93 (1H, d, J=7.5 Hz), 6.86 (1H, br s), 6.75 (1H, d, J=8.1 Hz), 5.70 (1H, d, J=7.5 Hz), 5.03 (1H, d, J=18.4 Hz), 4.52 (1H, d, J=18.4 Hz), 4.16 (2H, q, J=11.0, 6.0 Hz), 3.21 (3H, s), 2.07 (3H, s), 1.45 (9H, s), 1.29 (3H, s), 1.26 (3H, s).

(R)-1-[1-(4-Acetoxy-3,3-dimethyl-2-oxo-butyl)-2-oxo-5-pyridin-2-yl-2,3-dihydro-1H-benzo[e][1,4]diazepin-3-yl]-3-(3-methylamino-phenyl)-urea (TR2-A)

Compound 18-A (1046 g) was dissolved in acetic acid saturated (about 1.5 molar) with hydrogen chloride (11 L) to give a light orange solution. The mixture exothermed from 15° C. to 23° C. The mixture was stirred at room temperature for 3 hours. TLC (small sample neutralised with sodium bicarbonate and extracted into DCM; elute:ethyl acetate) indicated that all of 18-A (Rf=0.35) had been converted into TR2-A (Rf=0.20). Nitrogen was bubbled through the solution for one hour to reduce hydrogen chloride content. Most of the acetic acid was removed under vacuum (65° C./<60 mmHg) to give a thick amber oil. The product was dissolved in DCM (10 L) and poured into a stirred saturated solution of sodium bicarbonate (15 L). More solid sodium bicarbonate was added until effervescence stopped and pH=8. (Do not use a stronger base than bicarbonate. Even carbonate will remove the acetate group). The DCM layer was removed and the aqueous layer re-extracted with DCM (2×2 L). The combined DCM extracts were dried over anhydrous sodium sulfate and filtered through a bed of celite. The DCM solution was evaporated under vacuum to give a foamed-up oil. Ethyl acetate (5.5 L) was added to the material while still in the rotating rotary evaporator flask with the vacuum off. The oil dissolved and a solid slowly formed. The mixture was allowed to cool to room temperature while standing overnight. The mixture was filtered and washed with ethyl acetate (4 L). The filter cake was pulled down hard and then dried in a vacuum oven at 35° C. overnight. The solid was broken-up and passed through a sieve before drying further in a vacuum at 35° C. for 2 days (no weight change between second and third day of drying) to give an off-white powder (740 g). TR2-A may be recrystallized from ethyl acetate, if required. A total of 3711 g (84% yield, 98.2% HPLC purity, 99.9% ee R-isomer chiral HPLC purity) of compound TR2-A was made from about 5234 g of compound 18-A using the above method. $^1$H NMR (500 MHz, CDCl$_3$) δ 8.60 (1H, d, J=4.9 Hz), 8.15 (1H, d, J=7.9 Hz), 7.77 (1H, dt, J=1.8, 7.9 Hz), 7.49 (1H, dt, J=1.8, 7.9 Hz), 7.38 (1H, dd, J=1.8, 7.9 Hz), 7.33 (1H, ddd, J=1.2, 4.9, 7.3 Hz), 7.25 (with CHCl$_3$ peak, t, J=7.3 Hz), 7.10 (1H, d, J=7.3 Hz), 7.03-6.93 (3H, m), 6.75 (1H, t, J=2.1 Hz), 6.52 (1H, dd, J=1.8, 7.3 Hz), 6.28 (1H, dd, J=1.8, 7.9 Hz), 5.72 (1H, d, J=7.9 Hz), 4.96 (1H, d, J=18.0 Hz), 4.50 (1H, d, J=18.0 Hz), 4.14 (2H, q, J=10.6 Hz), 3.73 (1H, br s), 2.77 (3H, s), 2.05 (3H, s), 1.26 (3H, s), 1.23 (3H, s).

Example 4

Solubility Study

A solubility study confirmed that (TR1) and (TR2-A) are more soluble in aqueous solution than YF476; and (TR2-A) is more soluble in aqueous solution than (TR1). The test compound (2.5 mg of solid; n=1) was weighed in a clear glass vial and Britton-Robinson's buffer (0.5 mL) was added (pH 2.01, pH 3.06, pH 4.06, pH 5.08, pH 5.99, pH 6.98, and pH 8.16). The solution was agitated at ambient temperature overnight using a vial roller system, and then filtered (0.45 μm pore size; without pre-saturation). Two aliquots (50 μL) were sampled from the filtrate and diluted with one volume of 0.1 N hydrochloric acid and methanol (1:1 v/v) before analysis by HPLC-UV. A standard was prepared in DMSO at 10 mg/mL (n=1) which was then diluted 10-fold in 0.1 N hydrochloric acid and methanol (1:1 v/v) to give a 1 mg/mL solution. The concentration of test compound in the filtrate was quantified relative to the concentration standard.

Analysis was done using a gradient HPLC-UV system with a total cycle time of 6 min. The UV detection between 220 nm and 300 nm was done using a photodiode array detector.

| pH | Aqueous solubility | | | Solubility advantage | | |
|---|---|---|---|---|---|---|
| | YF476 (µg/mL) | (TR1) (µg/mL) | (TR2-A) (µg/mL) | ((TR1)/ YF476) | ((TR2-A)/ YF476) | ((TR2-A)/ TR1) |
| 2.01 | 2650 | 5000 | 4190 | 1.9 | 1.6 | 0.8 |
| 3.06 | 99.7 | 645 | 730 | 6.5 | 7.3 | 1.1 |
| 4.06 | 5.9 | 58.2 | 218 | 9.9 | 36.9 | 3.7 |
| 5.08 | 1.4 | 9.8 | 56 | 7 | 40.0 | 5.7 |
| 5.99 | 1.3 | 11.6 | 47.2 | 8.9 | 36.3 | 4.1 |
| 6.98 | 1.4 | 5.84 | 51 | 4.2 | 36.4 | 8.7 |
| 8.16 | 1.5 | 7.81 | 45.4 | 5.2 | 30.3 | 5.8 |

The solubility advantage of (TR1) and (TR2-A) over YF476 is especially pronounced at pH 4-6, which is the pH range of the part of the small intestine—duodenum to terminal jejunum or mid ilium—where most drug absorption takes place. This enhanced solubility is an indicator that (TR1), (TR2), (TR3) and (TR2-A) are likely to be more bioavailable, and therefore better drug candidates than YF476.

The values given in the table above are for crystalline YF476 and (TR2-A) and amorphous (TR1).

Crystalline (TR2-A) had almost the same solubility profile as amorphous (TR2-A), and is therefore likely to have comparable oral bioavailability. This is surprising because crystalline YF476 is poorly bioavailable and had to be converted to an amorphous form (spray-dried dispersion) to increase solubility and oral bioavailability. This should not be necessary with (TR2-A).

| pH | Aqueous solubility | |
|---|---|---|
| | (TR2-A) amorphous (µg/mL) | (TR2-A) crystalline (µg/mL) |
| 2.01 | 5000 | 4190 |
| 3.06 | 683 | 730 |
| 4.06 | 282 | 218 |
| 5.08 | 128 | 56 |
| 5.99 | 53.4 | 47.2 |
| 6.98 | 43 | 51 |
| 8.16 | 40.2 | 45.4 |

Example 5

Morphology Studies

In contrast to YF476, studies indicate that (TR1) and the pure enantiomers (TR2) and (TR3) prefer an amorphous state over a crystalline state.

Initial attempts to crystallise (TR2) and (TR3) were unsuccessful, indicating preference for an amorphous state. Indeed, XRPD analysis of (TR2) confirmed an amorphous state. This is indicative of an advantage over YF476 in terms of the formulation of a suitable pharmaceutical composition. YF476 is crystalline, which contributes to poor solubility and bioavailability. Amorphous YF476 can be used to increase bioavailability, but requires stabilization, which can be achieved as a solid dispersion on hydroxypropyl methyl cellulose by spray-drying. Formulation of (TR) (in racemic, non-racemic or enantiomerically pure form), which prefers an amorphous state, would avoid the need for this stabilization.

Example 6

CCK Receptor Antagonism (TR2) and (TR3) were compared with YF476 and YM022 in $CCK_1$ and $CCK_2$ receptor functional assays with the following assay criteria.

| Receptor assay (antagonist effect) | Source | Stimulus | Incubation | Measured component | Detection method |
|---|---|---|---|---|---|
| $CCK_1$ (human) | Human recombinant (CHO cells) | CCK-8s (300 nM) | 10 min 37° C. | cAMP | HTRF |
| $CCK_2$ (human) | Human recombinant (CHO cells) | CCK-8s (10 nM) | 10 min 37° C. | cAMP | HTRF |

HTRF: Homogeneous time-resolved fluorescence
cAMP: cyclic adenosine monophosphate
CHO: Chinese hamster ovary The results of the assays are shown in the table below:

| | $CCK_1$ | | $CCK_2$ | | Selectivity | $K_B$ |
|---|---|---|---|---|---|---|
| Antagonist | $IC_{50}$ (nM) | $K_B$ (µM) | $IC_{50}$ (nM) | $K_B$ (nM) | $IC_{50}$ $(CCK_1)$/ $IC_{50}$ $(CCK_2)$ | $(CCK_1)$/ $K_B$ $(CCK_2)$ |
| YF476 | 160 | 24 | 0.52 | 0.064 | 308 | 375 |
| TR2 | 1000 | 150 | 2.5 | 0.31 | 400 | 484 |
| TR3 | 8500 | 1300 | 99.0 | 12.0 | 86 | 108 |
| YM022 | — | — | 0.55 | 0.68 | — | — |

(TR2) and (TR3) were potent $CCK_2$ receptor antagonists and less potent $CCK_1$ receptor antagonists. In the $CCK_2$ assay, (TR2) compared favourably to YF476 and YM022: (TR2) was only about 5-fold less potent than YF476 and YM022; and although affinity of (TR2) for the $CCK_2$ receptor was about 5-fold lower than that of YF476, it was twice that of YM022. Furthermore, the selectivity of (TR2) for the $CCK_2$ receptor over the $CCK_1$ receptor was 30% higher than the selectivity of YF476. The potency of the antagonists is expressed as $IC_{50}$, the concentration of antagonist that causes a half-maximum inhibition of the control agonist response. The affinity of the antagonist for the receptor is expressed as $K_B$, the concentration of antagonist, which would occupy 50% of the receptors at equilibrium.

Example 7

Receptor Binding Screen

The potential of (TR2) and (TR3) to bind to other cellular and nuclear receptors was tested in a panel of 80 receptors. The assay used radiolabelled receptor ligands (agonist or antagonist, depending on the receptor), and the ability of the test compounds to inhibit ligand binding was measured by scintillation counting. No significant receptor binding (other than $CCK_2$ and $CCK_1$) was found.

Example 8

Pre-Clinical Studies: Proliferation of Cells In Vitro

The potency of (TR2) and (TR3) was tested in a sulphorhodamine-B (SRB) proliferation assay in a human gastric adenocarcinoma cell line stably transfected with the human gastrin/$CCK_2$ receptor gene ($AGS_{GR}$). SRB is a fluorescent dye that binds to proteins, so cells with a high rate of protein synthesis (proliferative cells) will show high levels of fluorescence in the SRB assay. The gastrin fragment G17 has an anti-proliferative effect on $AGS_{GR}$ cells. So, when treated with G17, the cells show lower levels of fluorescence in the SRB assay. (TR2) and (TR3) were compared with the positive controls YF476 and YM022. (TR2), YF476 and YM022, at a concentration of 100 nM, all completely inhibited the anti-proliferative effects of G17 (10 nM). (TR3), at a concentration of 500 nM, had the same effect. None of the compounds tested affected $AGS_{GR}$ cell proliferation in the absence of G17.

Example 9

Pre-Clinical Studies: Rats with a Gastric Fistula

The effect of subcutaneous injections of YF476, (TR2) and (TR3) on pentagastrin-stimulated gastric acid secretion was tested in conscious rats with a chronic gastric fistula. All treatments dose-dependently inhibited the acid secretion response. $ED_{50}$ values for YF476, (TR2), and (TR3) were 0.012, 0.03 and 0.3 µmol/kg, respectively.

Example 10

Pharmacokinetics in Healthy Subjects

In an initial study, healthy volunteers took a single oral dose of 100 mg (TR2) as an active pharmaceutical ingredient (API) in a capsule. Plasma concentrations were measured. The area under the curve of plasma concentrations of (TR2) after a single oral dose of 100 mg of active pharmaceutical ingredient (AUC=439.1) was about twice that observed for a similar formulation of a single oral dose of YF476 100 mg (AUC=198.5). Thus, (TR2) was observed to be more bioavailable than YF476.

In further clinical studies, healthy volunteers (n=8) took single oral doses of 5, 15, 50 and 100 mg (TR2) as an active pharmaceutical ingredient (API) in a capsule. (Capsule formulation TR2 powder (API) in a hard gelatin capsule, no excipients, no processing). Plasma concentrations were measured. The mean area under the curve (AUC) of plasma concentrations of (TR2) after a single oral dose of 100 mg of API ($AUC_{0-24\,h}$ (ng·h/mL)=241.5) was about three times that observed for a similar formulation (YF476 powder (crystalline) in hard gelatin capsule, with no excipient, no processing of the API) of a single oral dose of YF476 100 mg ($AUC_{0-24\,h}$=81.3; n=10). Thus, (TR2) was observed to have better oral bioavailability than YF476 in the healthy subjects.

Healthy volunteers (n=8) took single oral doses of 5, 15, 25 and 50 mg (TR2-A) as API in a capsule (TR2-A (crystalline) in hard gelatin capsule with no excipient, no processing of the API). Plasma concentrations of (TR2) and (TR2-A) were measured. The area under the curve of plasma concentrations of (TR2) after a single oral dose of 50 mg of (TR2-A) API ($AUC_{0-24\,h}$=212.5) was about the same as that observed for a similar formulation of a single oral dose of (TR2) 100 mg ($AUC_{0-24\,h}$=241.5). Thus, (TR2-A) was observed to have better oral bioavailability than (TR2) in the healthy subjects. Moreover, the plasma concentrations of (TR2-A) were low ($AUC_{0-24\,h}$<10), indicating that (TR2-A) is acting as a prodrug for (TR2).

Example 11

Clinical Studies: Pharmacodynamic Effect in the Healthy Subject

Pentagastrin induces gastric acid secretion, and thereby increases $H^+$ concentration in the gastric juice. In an initial study, in a healthy volunteer, single oral doses of 5, 25 and 100 mg of (TR2) administered in conjunction with pentagastrin infusion were observed to cause similar dose-dependent inhibition of the increase in $H^+$ concentration of gastric aspirate induced by the intravenous infusion of pentagastrin as observed for corresponding dosing of YF476 with pentagastrin infusion. Thus, the potency of (TR2) as a $CCK_2$ receptor antagonist was similar to that of YF476 in the healthy subject.

In further clinical studies, in healthy volunteers, single oral doses of 5, 15, 50 and 100 mg of (TR2) or 5, 15, 25 and 50 mg (TR2-A) were administered in conjunction with pentagastrin infusion (i.v. dose 0.6 µg/kg/h for 2 h). A plot of the mean of $H^+$ concentrations after (TR2-A) doses is shown in FIG. 1.

Both (TR2) and (TR2-A) were observed to cause similar dose-dependent inhibition of the increase in $H^+$ concentration of gastric aspirate induced by the intravenous infusion of pentagastrin as observed for dosing of YF476 with pentagastrin infusion. 100 mg of (TR2) and 50 mg (TR2-A) caused similar inhibition of the increase in $H^+$ concentration of gastric aspirate induced by the intravenous infusion of pentagastrin as observed for dosing of 100 mg YF476. Thus, the potency of (TR2) as a $CCK_2$ receptor antagonist was similar to that of YF476 in healthy subjects, and the potency of (TR2-A) is greater than that of both (TR2) and YF476.

The observed results showed that (TR2) supresses the effect of pentagastrin in a dose-dependent manner, and that a lower dose of (TR2-A) than (TR2) was required for full suppression.

Embodiments of the invention have been described by way of example and these embodiments are to be considered as illustrative rather than restrictive. It will be appreciated that variations in form and detail can be made without departing from the true scope of the invention, which is to be defined by the appended claims.

The invention claimed is:

1. A method of treating a disorder selected from a gastric acid-related disorder, pain, gastric and duodenal ulcers, NSAID induced gastric ulceration, dyspepsia, gastroesophageal reflux disease (GORD), Barrett's oesophagus, Zollinger Ellison syndrome (ZES), hypergastrinaemia, gastritis, neuroendocrine tumours, parietal cell hyperplasia, fundic gland polyps, gastric cancer, colorectal cancer, medullary thyroid cancer, pancreatic cancer or nociception in a subject in need thereof, the method comprising administering to the subject a therapeutically effective amount of a compound of formula (A):

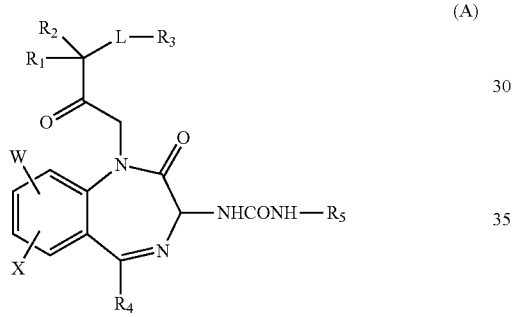

(A)

or a pharmaceutically acceptable salt thereof,
wherein,
$R_1$ and $R_2$ are each, independently, H, $C_{1-3}$ aliphatic, halo, or $C_{1-3}$ haloaliphatic, or wherein $R_1$ and $R_2$ together with the intervening carbon atom to which they are bonded, form a $C_{3-6}$ carbocyclic moiety;
L is a bond or $C_{1-3}$ alkylene;
$R_3$ is —$OR_6$ or —$SR_6$;
W and X are, independently, hydrogen, halo, $C_{1-8}$ alkyl or $C_{1-8}$ alkoxy;
$R_4$ and $R_5$ are both, independently, a monocyclic aryl or heteroaryl, optionally substituted with one or more substituents independently selected from halo, hydroxy, amino, nitro, carboxyl, carboxamido, cyano, —$SO_3H$, and optionally substituted $C_{1-8}$ alkyl, $C_{1-8}$ alkoxy, $C_{1-8}$ alkylamino or alkyl)amino;
$R_6$ is hydrogen, C(O)R, alkyl, P(O)(OH)$_2$, —P(O)(O($C_{1-6}$)alkyl)$_2$, an alkylcarbonyloxyalkyl, ($C_{1-6}$)alkoxycarbonylaminomethyl, succinoyl, or an α-aminoalkylcarbonyl; and
R is an optionally substituted aliphatic, heteroaliphatic, aromatic, or heteroaromatic moiety.

2. The method of claim 1, wherein at least one of $R_4$ and $R_5$ is unsubstituted or substituted phenyl or pyridyl.

3. The method of claim 1, wherein the compound of formula (A) is a compound of formula (B):

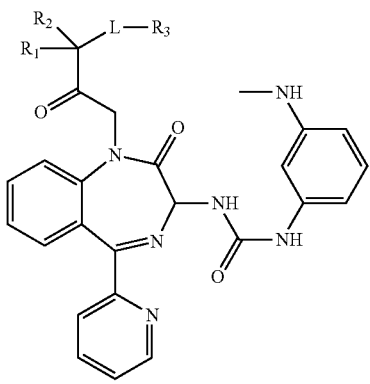

(B)

or a pharmaceutically acceptable salt thereof.

4. The method of claim 1, wherein the compound of formula (A) is selected from:

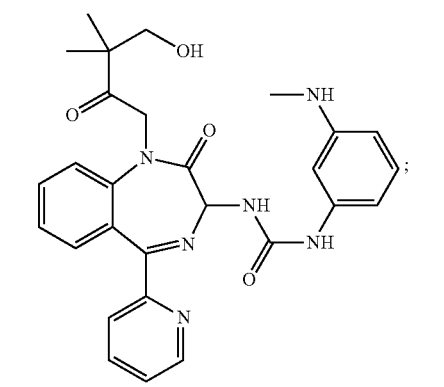

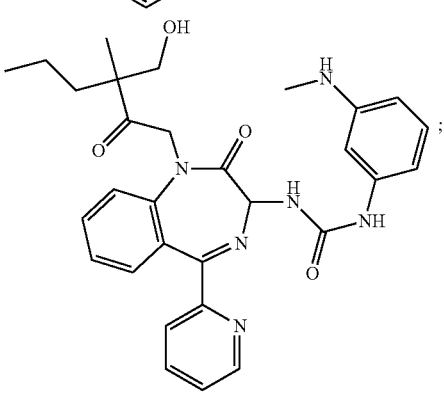

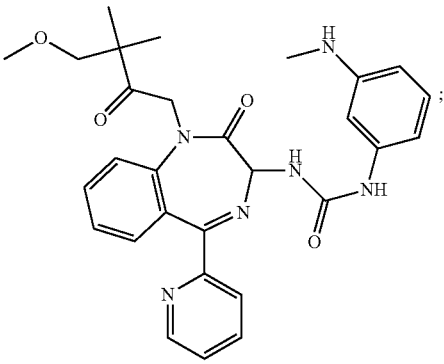

75
-continued
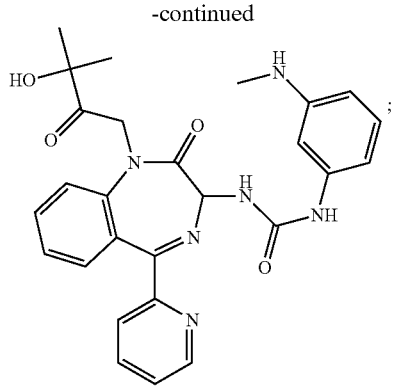
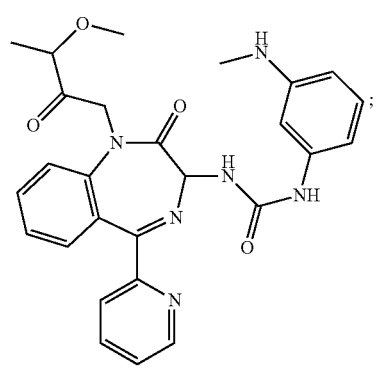
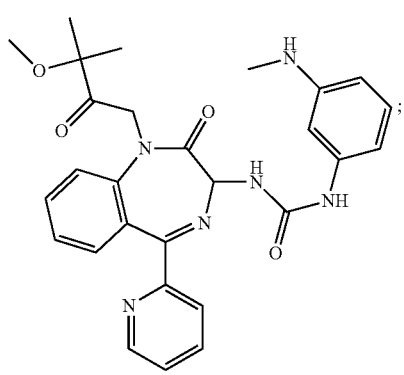
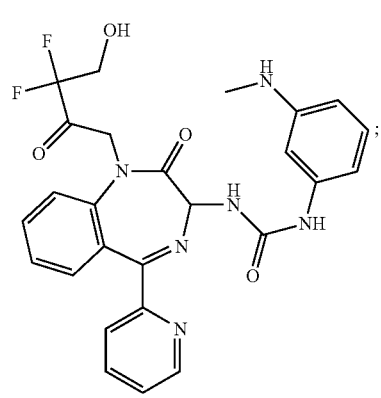
76
-continued
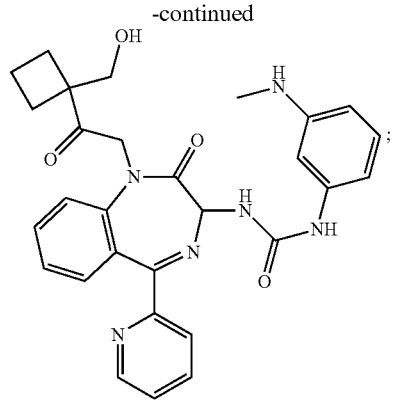
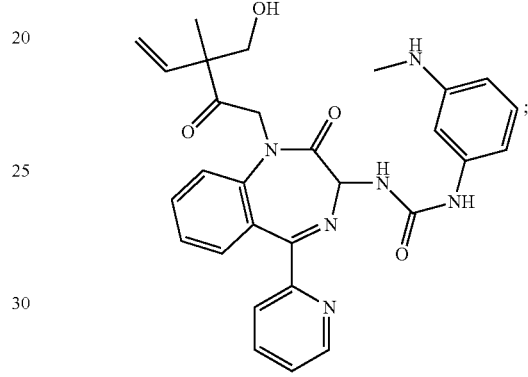
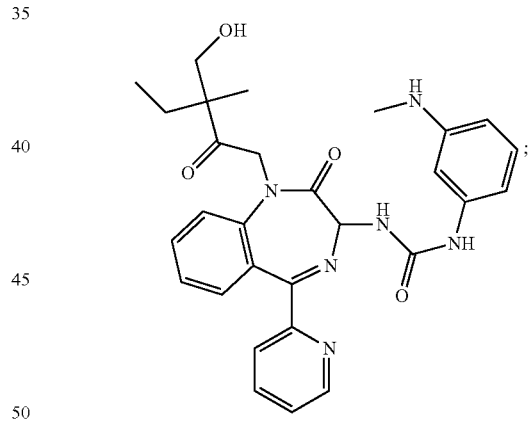
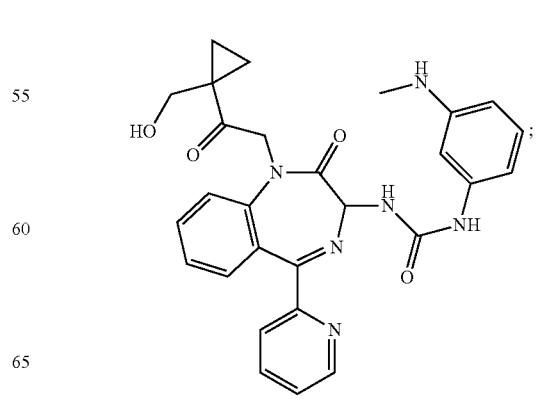

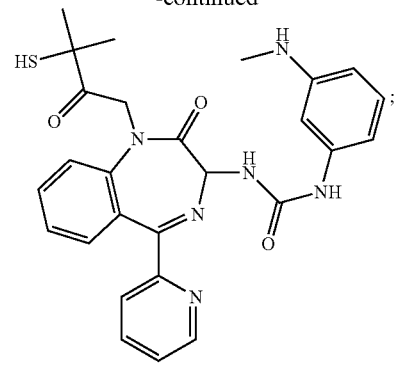

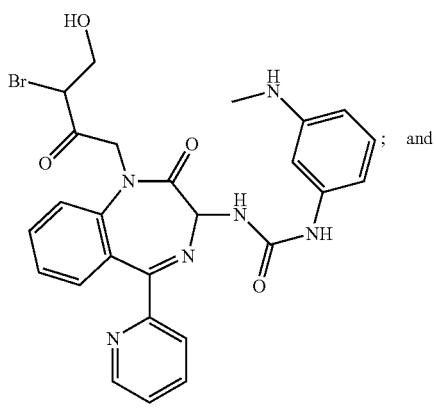

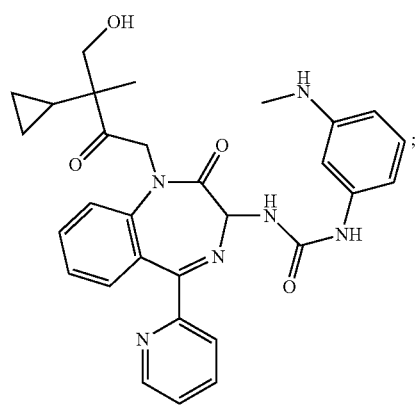

or a pharmaceutically acceptable salt, ester, thioester, salt of an ester or thioester, or prodrug thereof;

wherein an ester is a compound in which the H of —OH is replaced by a moiety —C(O)R, wherein R is an optionally substituted aliphatic, heteroaliphatic, aromatic or heteroaromatic moiety;

wherein a thioester is a compound in which the H of —SH is replaced by a moiety —C(O)R, wherein R is an optionally substituted aliphatic, heteroaliphatic, aromatic or heteroaromatic moiety; and wherein a prodrug is a compound in which the H of —OH or H of —SH is replaced by —P(O)(OH)$_2$, —P(O)(O(C$_{1-6}$)alkyl)$_2$, an alkylcarbonyloxyalkyl, (C$_{1-6}$)alkoxycarbonylaminomethyl, succinoyl, or a α-aminoalkylcarbonyl.

5. The method of claim 1, wherein the compound is a compound (TR):

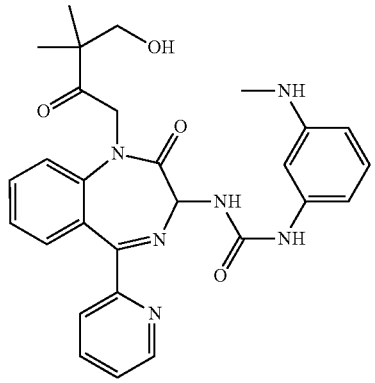

or a pharmaceutically acceptable salt, ester, salt of an ester, or prodrug thereof;

wherein an ester is a compound in which the H of —OH is replaced by a moiety —C(O)R, wherein R is an optionally substituted aliphatic, heteroaliphatic, aromatic or heteroaromatic moiety; and wherein a prodrug is a compound in which the H of —OH is replaced by —P(O)(OH)$_2$, —P(O)(O(C$_{1-6}$)alkyl)$_2$, an alkylcarbonyloxyalkyl, (C$_{1-6}$)alkoxycarbonylaminomethyl, succinoyl, or a α-aminoalkylcarbonyl.

6. The method of claim 5, wherein (TR) is provided as a racemic mixture of enantiomers (TR2) and (TR3), a non-racemic mixture of enantiomers (TR2) and (TR3), or as a single enantiomer (TR2) or (TR3) in optically pure form

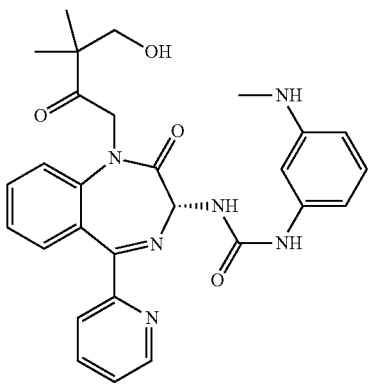

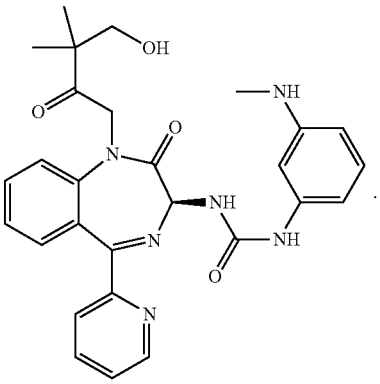

7. The method of claim 6, wherein the compound (TR) is a compound (TR2)

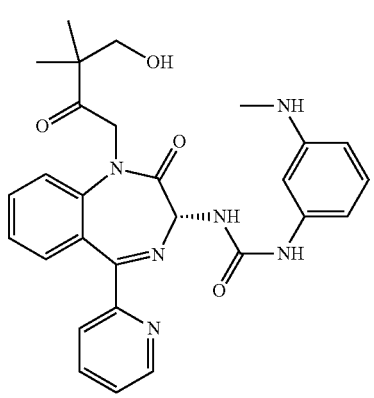

(TR2)

or a pharmaceutically acceptable salt thereof.

8. The method of claim 1, wherein the compound is a compound of formula (C)

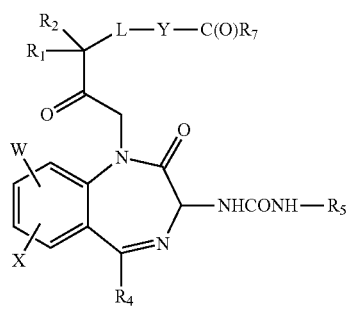

(C)

or a pharmaceutically acceptable salt thereof, wherein,

Y is —O— or —S—; and $R_7$ is an optionally substituted aliphatic, heteroaliphatic, aromatic or heteroaromatic moiety.

9. The method of claim 8, wherein the compound of formula (C) is a compound (TR-A):

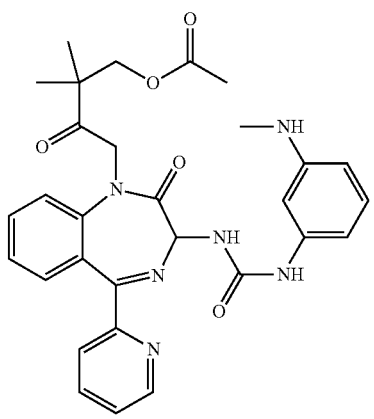

(TR-A)

or a pharmaceutically acceptable salt thereof.

10. The method of claim 9, wherein the compound (TR-A) is a compound (TR2-A)

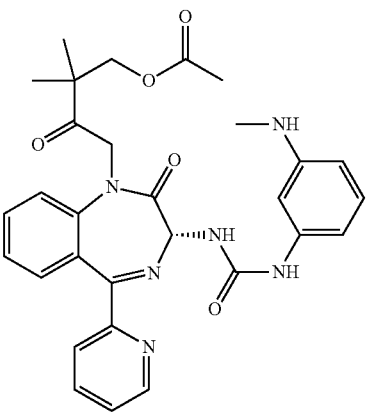

(TR2-A)

or a pharmaceutically acceptable salt thereof.

11. The method of claim 1, wherein the compound of formula (A) is administered as an oral, sublingual, or parenteral dosage form.

12. The method of claim 1, further comprising administering to the subject a therapeutically effective amount of an additional active agent.

13. The method of claim 12, wherein the additional active agent is a histamine $H_2$-receptor antagonist, a PPI, a potassium-competitive acid inhibitor or any other gastric acid suppressant, a cytotoxic agent, a tumour-specific antibody or an analgesic.

14. The method of claim 8, wherein the compound of formula (C) is a compound of formula (D):

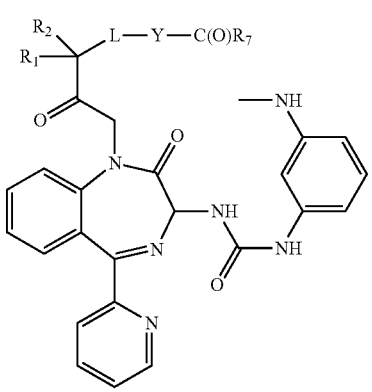

(D)

or a pharmaceutically acceptable salt thereof.

15. The method of claim 14, wherein the compound of formula (D) is a compound of formula (E):

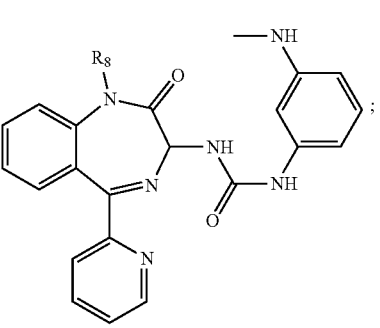

(E)

or a pharmaceutically acceptable salt thereof, wherein $R_8$ is selected from

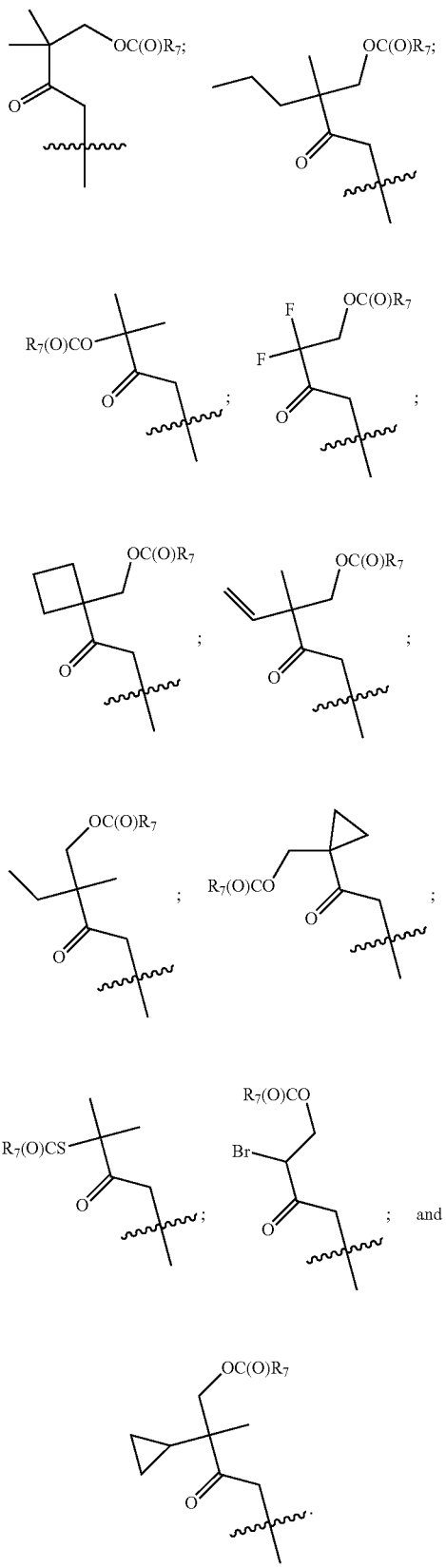

16. The method of claim 15, wherein the compound is a compound of formula (F):

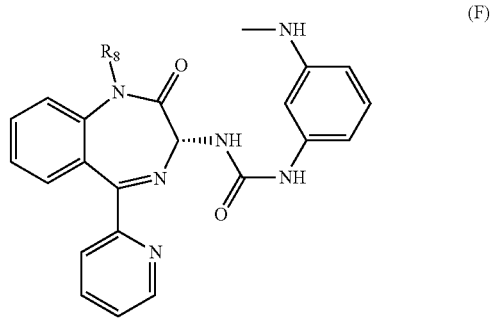

or a pharmaceutically acceptable salt thereof.

17. The method of claim 16, wherein $R_7$ is substituted or unsubstituted $C_{1-6}$ aliphatic.

18. The method of claim 17, wherein the compound is a compound (TR2-A):

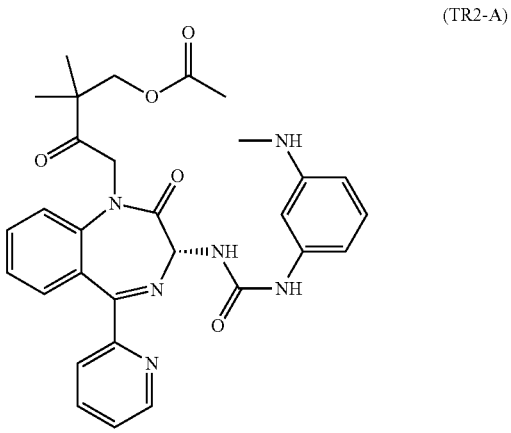 [SMILES: CNc1cccc(NC(=O)N[C@@H]2N=C(c3ccccn3)c3ccccc3N(CC(=O)C(C)(C)COC(C)=O)C2=O)c1]

or a pharmaceutically acceptable salt thereof.

19. The method of claim 1, wherein the disorder is selected from the group consisting of gastric and duodenal ulcers, NSAID-induced gastric ulceration, dyspepsia, GORD, Barrett's oesophagus, ZES, hypergastrinaemia induced by a PPI or other acid-suppressant, gastritis, neuroendocrine tumours, parietal cell hyperplasia, fundic gland polyps, gastric cancer, colorectal cancer, medullary thyroid cancer, and pancreatic cancer.

20. The method of claim 1, wherein the disorder is selected from the group consisting of nociception and pain.

21. The method of claim 1, wherein the disorder is selected from the group consisting of a tumour of the pancreas, stomach, colon, or medullary thyroid, and wherein the method further comprises administering to the subject a therapeutically effective amount of a cytotoxic therapy or tumour-specific antibody.

22. The method of claim 12, wherein the additional active agent is an analgesic.

23. The method of claim 1, wherein the compound is:

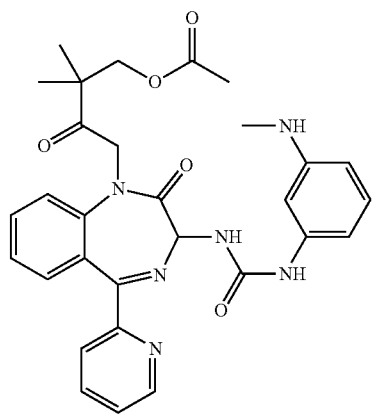

(TR-A)

or a pharmaceutically acceptable salt thereof.

24. The method of claim 1, wherein the compound is:

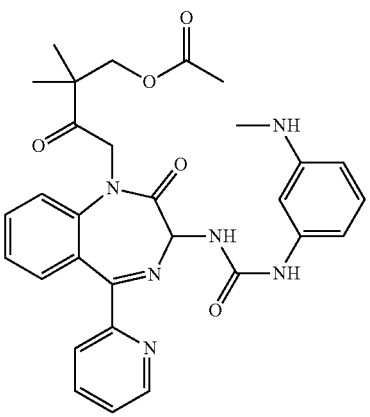

(TR-A)

or a pharmaceutically acceptable salt thereof; and the disorder is hypergastrinaemia.

25. The method of claim 1, wherein the disorder is hypergastrinaemia.

* * * * *

UNITED STATES PATENT AND TRADEMARK OFFICE
CERTIFICATE OF CORRECTION

PATENT NO. : 10,906,884 B2
APPLICATION NO. : 16/382737
DATED : February 2, 2021
INVENTOR(S) : Malcolm James Boyce et al.

Page 1 of 1

It is certified that error appears in the above-identified patent and that said Letters Patent is hereby corrected as shown below:

In the Claims

Claim 1, Column 73, Line 56, should read:
alkoxy, C1– 8 alkylamino or di(C1– 8 alkyl)amino;

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*